United States Patent
Youngblood et al.

(10) Patent No.: US 11,013,883 B2
(45) Date of Patent: *May 25, 2021

(54) STRESS REDUCTION AND SLEEP PROMOTION SYSTEM

(71) Applicant: Youngblood IP Holdings, LLC, Mooresville, NC (US)

(72) Inventors: Todd Youngblood, Mooresville, NC (US); Tara Youngblood, Mooresville, NC (US)

(73) Assignee: KRYO, INC., Mooresville, NC (US)

( * ) Notice: Subject to any disclaimer, the term of this patent is extended or adjusted under 35 U.S.C. 154(b) by 657 days.

This patent is subject to a terminal disclaimer.

(21) Appl. No.: 15/848,816

(22) Filed: Dec. 20, 2017

(65) Prior Publication Data

US 2018/0110960 A1 Apr. 26, 2018

Related U.S. Application Data

(63) Continuation-in-part of application No. 15/705,829, filed on Sep. 15, 2017, now Pat. No. 10,986,933.
(Continued)

(51) Int. Cl.
*A61M 21/02* (2006.01)
*A61B 5/0205* (2006.01)
(Continued)

(52) U.S. Cl.
CPC .......... *A61M 21/02* (2013.01); *A47C 21/003* (2013.01); *A47C 21/044* (2013.01);
(Continued)

(58) Field of Classification Search
CPC .......... A47C 7/74; A47C 7/742; A47C 7/744; A47C 7/748; A47C 21/04; A47C 21/042;
(Continued)

(56) References Cited

U.S. PATENT DOCUMENTS 2,753,435 A 7/1956 Ivar
3,230,556 A 1/1966 Wiusor
(Continued)

FOREIGN PATENT DOCUMENTS

KR 20110102637 A 9/2011
WO 2014145436 A1 9/2014

OTHER PUBLICATIONS

Buysse, D.J., Reynolds, C.F., Monk, T.H., Berman, S.R., & Kupfer, D.J. (1989). The Pittsburgh Sleep Quality Index (PSQI): A new instrument for psychiatric research and practice. Psychiatry Research, 28(2), 193-213.
(Continued)

*Primary Examiner* — Nicholas F Polito
(74) *Attorney, Agent, or Firm* — Neo IP

(57) ABSTRACT

The present invention provides systems, methods, and articles for stress reduction and sleep promotion. A stress reduction and sleep promotion system includes at least one remote device and an article for temperature conditioning a surface. The stress reduction and sleep promotion system includes at least one body sensor, at least one remote server, and/or a pulsed electromagnetic frequency device in other embodiments.

20 Claims, 53 Drawing Sheets

Related U.S. Application Data which is a continuation-in-part of application No. 14/777,050, filed as application No. PCT/US2014/030202 on Mar. 17, 2014, now Pat. No. 10,278,511.

(60) Provisional application No. 62/398,257, filed on Sep. 22, 2016, provisional application No. 61/800,768, filed on Mar. 15, 2013.

(51) Int. Cl.
| | | |
|---|---|---|
| *A47C 27/08* | (2006.01) | |
| *A47C 21/04* | (2006.01) | |
| *A47C 21/00* | (2006.01) | |
| *A47C 31/00* | (2006.01) | |
| *A61B 5/00* | (2006.01) | |
| *A61B 5/11* | (2006.01) | |
| *A61B 5/024* | (2006.01) | |
| *A61M 21/00* | (2006.01) | |

(52) U.S. Cl.
CPC .......... *A47C 21/046* (2013.01); *A47C 21/048* (2013.01); *A47C 27/085* (2013.01); *A47C 31/008* (2013.01); *A61B 5/0031* (2013.01); *A61B 5/0205* (2013.01); *A61B 5/11* (2013.01); *A61B 5/1103* (2013.01); *A61B 5/4815* (2013.01); *A61B 5/024* (2013.01); *A61B 5/1106* (2013.01); *A61B 5/1113* (2013.01); *A61B 5/4809* (2013.01); *A61B 5/4818* (2013.01); *A61B 5/4821* (2013.01); *A61B 5/4884* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2205/17* (2013.01); *A61M 2230/04* (2013.01); *A61M 2230/08* (2013.01); *A61M 2230/30* (2013.01); *A61M 2230/40* (2013.01); *A61M 2230/50* (2013.01); *A61M 2230/60* (2013.01); *A61M 2230/62* (2013.01); *A61M 2230/63* (2013.01)

(58) Field of Classification Search
CPC ... A47C 21/044; A47C 21/048; A47C 27/085; A47C 27/144; A47C 31/008; A47C 21/003; A47C 21/046; A61B 5/0205; A61F 2007/0054; A61F 2007/0056; A61M 21/02
See application file for complete search history.

(56) References Cited

U.S. PATENT DOCUMENTS

| | | | |
|---|---|---|---|
| 4,132,262 | A | 1/1979 | Wibell |
| 4,459,468 | A | 7/1984 | Bailey |
| 4,777,802 | A | 10/1988 | Feher |
| 4,858,609 | A | 8/1989 | Cole |
| 5,033,136 | A | 7/1991 | Elkins |
| 5,304,112 | A | 4/1994 | Mrklas et al. |
| 5,329,096 | A | 7/1994 | Suematsu |
| 5,448,788 | A | 9/1995 | Wu |
| 5,894,615 | A | 4/1999 | Alexander |
| 5,948,303 | A | 9/1999 | Larson |
| 6,163,907 | A | 12/2000 | Larson |
| 6,273,810 | B1 | 8/2001 | Rhodes, Jr. et al. |
| 6,371,976 | B1 | 4/2002 | Vrzalik et al. |
| 6,484,062 | B1 | 11/2002 | Kim |
| 6,581,224 | B2 | 6/2003 | Yoon |
| 6,826,792 | B2 | 12/2004 | Lin |
| 7,041,049 | B1 | 5/2006 | Raniere |
| 7,238,289 | B2 | 7/2007 | Suddath |
| 7,248,915 | B2 | 7/2007 | Rönnholm |
| 7,306,567 | B2 | 12/2007 | Loree |
| 7,460,899 | B2 | 12/2008 | Almen |
| 7,524,279 | B2 | 4/2009 | Auphan |
| 7,608,041 | B2 | 10/2009 | Sutton |
| 7,699,785 | B2 | 4/2010 | Nemoto |
| 7,868,757 | B2 | 1/2011 | Radivojevic et al. |
| 8,096,960 | B2 | 1/2012 | Loree et al. |
| 8,179,270 | B2 | 5/2012 | Rai et al. |
| 8,191,187 | B2 | 6/2012 | Brykalski et al. |
| 8,290,596 | B2 | 10/2012 | Wei et al. |
| 8,348,840 | B2 | 1/2013 | Heit et al. |
| 8,418,285 | B2 | 4/2013 | Frias |
| 8,529,457 | B2 | 9/2013 | Devot et al. |
| 8,617,044 | B2 | 12/2013 | Pelgrim et al. |
| 8,768,520 | B2 | 7/2014 | Oexman et al. |
| 9,196,479 | B1 | 11/2015 | Cheng et al. |
| 9,402,763 | B2 | 8/2016 | Bledsoe |
| 10,391,009 | B2 * | 8/2019 | Bhai ...................... A61G 7/018 |
| 10,923,226 | B2 * | 2/2021 | Macary ................. A61M 21/02 |
| 2002/0014951 | A1 | 2/2002 | Kramer et al. |
| 2002/0080035 | A1 | 6/2002 | Youdenko |
| 2002/0124574 | A1 | 9/2002 | Guttman et al. |
| 2004/0049132 | A1 | 3/2004 | Barron et al. |
| 2005/0143617 | A1 | 6/2005 | Auphan |
| 2006/0137099 | A1 | 6/2006 | Feher |
| 2006/0293602 | A1 | 12/2006 | Clark |
| 2006/0293608 | A1 | 12/2006 | Rothman et al. |
| 2008/0234785 | A1 | 9/2008 | Nakayama et al. |
| 2009/0288800 | A1 | 11/2009 | Kang et al. |
| 2010/0011502 | A1 | 1/2010 | Brykalski et al. |
| 2010/0100004 | A1 | 4/2010 | Someren |
| 2010/0174198 | A1 | 7/2010 | Young et al. |
| 2010/0199687 | A1 | 8/2010 | Woods et al. |
| 2011/0015495 | A1 | 1/2011 | Dothie et al. |
| 2011/0073292 | A1 | 3/2011 | Datta et al. |
| 2011/0107514 | A1 | 5/2011 | Brykalski et al. |
| 2011/0230790 | A1 | 9/2011 | Kozlov |
| 2011/0247139 | A1 | 10/2011 | Tallent et al. |
| 2011/0267196 | A1 | 11/2011 | Hu et al. |
| 2013/0019611 | A1 | 1/2013 | Sims et al. |
| 2013/0060306 | A1 | 3/2013 | Colbauch |
| 2013/0234823 | A1 | 9/2013 | Kahn et al. |
| 2014/0316495 | A1 | 10/2014 | Augustine et al. |
| 2015/0093101 | A1 | 4/2015 | Lee |
| 2015/0289666 | A1 | 10/2015 | Chandler et al. |
| 2015/0351982 | A1 * | 12/2015 | Krenik ................... A61G 7/018 5/616 |
| 2016/0015315 | A1 | 1/2016 | Auphan et al. |
| 2016/0029808 | A1 | 2/2016 | Youngblood et al. |
| 2016/0151603 | A1 | 6/2016 | Shouldice et al. |
| 2016/0235610 | A1 | 8/2016 | Drake |
| 2016/0239624 | A1 * | 8/2016 | Short ...................... G16H 20/00 |
| 2017/0053068 | A1 * | 2/2017 | Pillai ...................... G16H 10/60 |

OTHER PUBLICATIONS

Quan, S.F. et. al; "Healthy Sleep the Characteristics of Sleep" (Sep. 21, 2016) pp. 1-4, retrieved from http://healthysleep.med.harvard.edu/healthy/science/what/characteristics.

Tobaldini, E. et. al; "Heart rate variability in normal and pathological sleep", Frontiers in Physiology, (Oct. 16, 2013), p. 1-11, vol. 4, Article 294, doi: 10.3389/fphys.2013.00294.

U.S. Appl. No. 61/800,768 Youngblood,Thermo electric heating and cooling device, filed Mar. 15, 2013, Drawings and Specification.

U.S. Appl. No. 62/398,257, Youngblood,Bed Pad With Custom Modulated Temperature Adjustment , filed Sep. 22, 2016, Drawings and Specification.

* cited by examiner

| Frequency | Tissue |
|---|---|
| 2 Hz | Nerve regeneration |
| 7 Hz | Bone growth |
| 10 Hz | Ligament healing |
| 15 Hz | Decreased skin necrosis |
| 15 Hz | Capillary formation |
| 15 Hz | Fibroblast proliferation |
| 20 Hz | Decreased skin necrosis |
| 20 Hz | Capillary formation |
| 20 Hz | Fibroblast proliferation |

Pravin ⌄
Today

⏻

Weekdays     10 PM     06 AM
Mon, Tue, Wed, Thu, Fri     Sleep time     Wake up time

Weekends     10 PM     06 AM
Sat, Sun     Sleep time     Wake up time

[ Add Sleep Profile → ]

| | | |
|---|---|---|
| Weekdays<br>Mon, Tue, Wed, Thu, Fri | 01 PM<br>Sleep time | 03 PM<br>Wake up time |
| | 11 PM<br>Sleep time | 05 AM<br>Wake up time |
| Weekends<br>Sat, Sun | 01 PM<br>Sleep time | 03 PM<br>Wake up time |
| | 02 AM<br>Sleep time | 09 AM<br>Wake up time |
Add Sleep Profile →
FIG. 46

  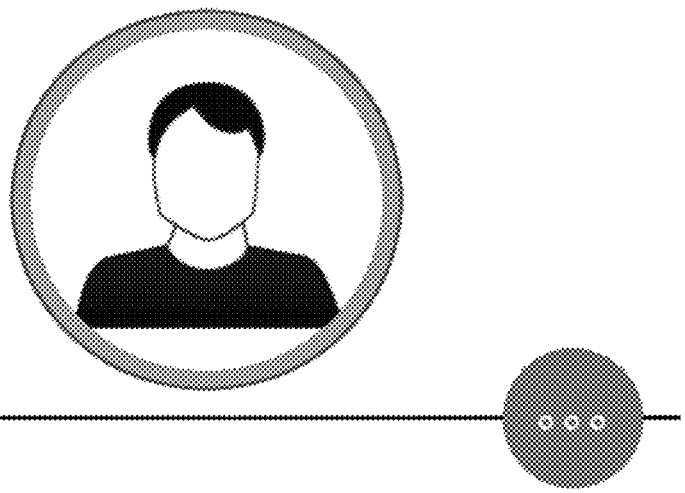 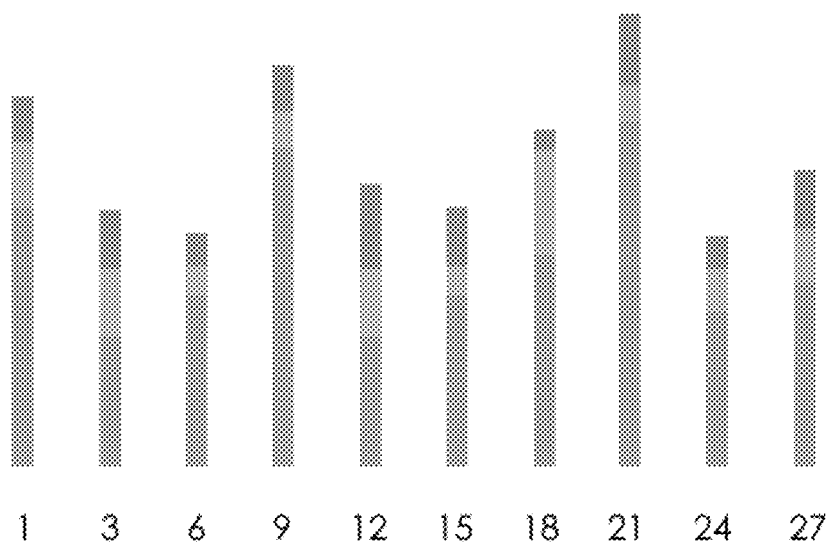
FIG. 48

STRESS REDUCTION AND SLEEP PROMOTION SYSTEM

CROSS REFERENCE TO RELATED APPLICATIONS

This application is related to and claims priority from the following U.S. patents and patent applications: this application is a continuation-in-part of U.S. application Ser. No. 15/705,829, filed Sep. 15, 2017, which is a continuation-in-part of U.S. application Ser. No. 14/777,050, filed Sep. 15, 2015, which is the National Stage of International Application No. PCT/US2014/030202, filed Mar. 17, 2014, which claims the benefit of U.S. Provisional Application No. 61/800,768, filed Mar. 15, 2013. U.S. application Ser. No. 15/705,829 also claims the benefit of U.S. Provisional Application No. 62/398,257, filed Sep. 22, 2016. Each of the above applications is incorporated herein by reference in its entirety.

BACKGROUND OF THE INVENTION

1. Field of the Invention

This invention relates broadly and generally to articles, methods, and systems for stress reduction and sleep promotion.

2. Description of the Prior Art

Several studies show that stress can negatively impact health by causing diseases or exacerbating existing conditions. Stress impacts the individual on a physiological and psychological level. Further, stress may lead individuals to adopt health damaging behaviors (e.g., smoking, drinking, poor nutrition, lack of physical activity). These physiological changes and health damaging behaviors can cause illnesses, such as sleep disturbances, impaired wound healing, increased infections, heart disease, diabetes, ulcers, pain, depression, and obesity or weight gain.

Therefore, it is important to manage and treat stress to maintain health. However, many individuals are under increased pressure due to a modern lifestyle, which leaves less time for relaxation and sleep. This lack of stress relief and sleep results in an increase in both mental and physical stress.

Various methods of stress relief are known, including exercise, biofeedback, and meditation. These systems often include a physical device that stimulates the body and/or senses. These systems may also shield the user from outside interferences.

Prior art patent documents include the following:

U.S. Pat. No. 4,858,609 for bright light mask by inventor Cole, filed Dec. 4, 1987 and issued Aug. 22, 1989, is directed to a bright light mask system for shining a high intensity light into a subject's eyes at preselected time periods to modify circadian rhythms. The system includes a mask adapted to be worn by the subject for covering the subject's eyes regardless of body position. The mask includes at least one light admitting aperture that is transparent to light energy. A light source is coupled to the aperture for generating and directing light into the subject's eyes. A light intensity of at least 2000 LUX of light having a wavelength in the range of 500 to 600 nanometers is delivered to each of the subject's eyes. A controller dictates the intensity of the light generated and the timing during which the light is on.

U.S. Pat. No. 5,304,112 for stress reduction system and method by inventors Mrklas et al., filed Oct. 16, 1991 and issued Apr. 19, 1994, is directed to an integrated stress reduction system that detects the stress level of a subject and displays a light pattern reflecting the relationship between the subject's stress level and a target level. At the same time, the system provides relaxing visual, sound, tactile, environmental, and other effects to aid the subject in reducing his or her stress level to the target level. In one preferred embodiment, the intensity, type, and duration of the relaxing effects are controlled by a computer program in response to the measured stress level. The light pattern stress level display uses a laser which is deflected on one axis by a measured stress level signal and on a second axis perpendicular to the first by a target signal representing the target stress level. The pattern produced is more complex when the two signals do not coincide, and becomes a less complex geometric figure as the subject's stress level approaches the target.

U.S. Publication No. 20020080035 for system for awaking a user by inventor Youdenko, filed Jun. 20, 2001 and published Jun. 27, 2002, is directed to an invention relating to an alarm clock system. The system according to the invention comprises sensor means for measuring ambient parameters. In particular, a user's body parameters are monitored so as to determine in which stage of sleep he is. Properties of the wake-up stimulus, such as sound volume of the stimulus or moment of generation of the stimulus, are adjusted in dependence on the inferred stage of sleep.

U.S. Pat. No. 6,484,062 for computer system for stress relaxation and operating method of the same by inventor Kim, filed Nov. 30, 1999 and issued Nov. 19, 2002, is directed to a computer system provided to relax stresses such as fatigue, VDT syndrome, occupational diseases or psychogenic possibly gained from long hours of computer usage. This new computer system is able to divert the negative effects of conventional computer to affirmative effects by introducing the aroma therapy. The new computer system provides not only the data programs of establishing, playing execution and controlling, but also the stress relief program comprising acoustic therapy, color therapy, fragrance therapy and tactual therapy and a stress perception program. The stress relief program is operated by an emission device through a converter. The equipment of the stress relief is installed on a peripheral device of computer such as a speaker, keyboard or monitor. The new concept of computer system for stress relaxation originates a combination of the computer system and the natural therapies applied the human senses like sight, hearing, feeling and smelling senses. With this new computer system, the computer user has a merit of stress relief during the computer operating.

U.S. Publication No. 20040049132 for device for body activity detection and processing by inventors Barron et al., filed Dec. 9, 2002 and published Mar. 11, 2004, is directed to a method and device for monitoring a body activity. The device has an actimetry sensor for measuring the activity and storage means for receiving data from the actimetry sensor. The data are analysed according to a method using summation algorithm, where a plurality of parameters relating to the activity are summed to provide advisory information relating to that activity. The analysis may include pre-programmed biasing constants or user supplied biasing constants.

U.S. Pat. No. 7,041,049 for sleep guidance system and related methods by inventor Raniere, filed Nov. 21, 2003 and issued May 9, 2006, is directed to a sleep efficiency monitor and methods for pacing and leading a sleeper through an optimal sleep pattern. Embodiments of the present invention include a physiological characteristic monitor for monitoring the sleep stages of a sleeper, a sensory stimulus generator for generating stimulus to affect the sleep stages of a sleeper, and a processor for determining what sleep stage the sleeper is in and what sensory stimulus is needed to cause the sleeper to move to another sleep stage. A personalized sleep profile may also be established for the sleeper and sleep guided in accordance with the profile parameters to optimize a sleep session. By providing sensory stimulus to a sleeper, the sleeper may be guided through the various sleep stages in an optimal pattern so that the sleeper awakens refreshed even if sleep is disrupted during the night or the sleeper's allotted sleep period is different than usual. Embodiments of the invention also involve calibration of the sleep guidance system to a particular sleeper.

U.S. Publication No. 20060293602 for sleep management device by inventor Clark, filed Apr. 8, 2004 and published Dec. 28, 2006, is directed to a short sleep/nap management apparatus and method. The apparatus has sensor means to detect one or more physiological parameters associated with a transition in sleep stages from wakefulness, processing means to process the parameters to determine when the transition is reached and start the timer to run for a predetermined period, and alarm means to actuate at the end of said predetermined period to awaken the user.

U.S. Publication No. 20060293608 for device for and method of predicting a user's sleep state by inventors Rothman et al., filed Feb. 28, 2005 and published Dec. 28, 2006, is directed to a device and a method for waking a user in a desired sleep state. The device may predict an occurrence when the user will be in the desired sleep state, such as light sleep, and wake the user during that predicted occurrence. In one embodiment, a user may set a wake-up time representing the latest possible time that the user would like to be awakened. The occurrence closest to the wake-up time when the user will be in light sleep may be predicted, thereby allowing the user to sleep as long as possible, while awakening in light sleep. To predict when the user will be in the desired sleep state, the user's sleep state may be monitored during the night or sleep experience and the monitored information may be used in predicting when the user will be in the desired sleep state.

U.S. Pat. No. 7,248,915 for natural alarm clock by inventor Rönnholm, filed Feb. 26, 2004 and issued Jul. 24, 2007, is directed to a mobile terminal having capability to determine when a user should be stimulated toward an awake state. The terminal includes a receiver for receiving a sleep descriptor signal indicative of at least one sleep characteristic of the user, and also includes a signal processing module for processing the sleep descriptor signal. The signal processing module is arranged to provide, at least partly in response to the sleep descriptor signal, a stimulation signal indicative that the user should be stimulated. The mobile terminal is also usable for communication by the user in the awake state. This invention further includes a method, system, and monitor to be used with the mobile terminal in order to stimulate the user toward an awake state.

U.S. Pat. No. 7,306,567 for easy wake wrist watch by inventor Loree, filed Jan. 10, 2005 and issued Dec. 11, 2007, is directed to a device that monitors a user's sleep cycles and operates to sound an alarm to awaken the user at an optimal point within a sleep cycle. Once an alarm time is set and the alarm is activated, the device begins to monitor a wearer's sleep cycles by identifying the points in time at which the wearer moves his or her body limbs. As the alarm time is approached, the device can trigger the alarm earlier if the wearer is at an optimal point in the sleep cycle or, even retard the triggering of the alarm if the optimal point in the sleep cycle is expected to occur shortly.

U.S. Publication No. 20080234785 for sleep controlling apparatus and method, and computer program product thereof by inventors Nakayama et al., filed Sep. 13, 2007 and published Sep. 25, 2008, is directed to a sleep controlling apparatus that includes a measuring unit that measures biological information of a subject; a first detecting unit that detects a sleeping state of the subject selected from the group consisting of a falling asleep state, a REM sleep state, a light non-REM sleep state and a deep non-REM sleep state, based on the biological information measured by the measuring unit; a first stimulating unit that applies a first stimulus of an intensity lower than a predetermined threshold value to the subject when the light non-REM sleep state is detected by the first detecting unit; and a second stimulating unit that applies a second stimulus of an intensity higher than the first stimulus after the first stimulus is applied to the subject.

U.S. Pat. No. 7,460,899 for apparatus and method for monitoring heart rate variability by inventor Almen, filed Feb. 25, 2005 and issued Dec. 2, 2008, is directed to a wrist-worn or arm band worn heart rate variability monitor. Heart rate variability ("HRV") refers to the variability of the time interval between heartbeats and is a reflection of an individual's current health status. Over time, an individual may use the results of HRV tests to monitor either improvement or deterioration of specific health issues. Thus, one use of the HRV test is as a medical motivator. When an individual has a poor HRV result, it is an indicator that they should consult their physician and make appropriate changes where applicable to improve their health. If an individual's HRV results deviate significantly from their normal HRV, they may be motivated to consult their physician. In addition, the inventive monitor is capable of monitoring the stages of sleep by changes in the heart rate variability and can record the sleep (or rest) sessions with the resulting data accessible by the user or other interested parties. Alternate embodiments of the invention allow assistance in the diagnosis and monitoring of various cardiovascular and sleep breathing disorders and/or conditions. Other embodiments allow communication with internal devices such as defibrillators or drug delivery mechanisms. Still other embodiments analyze HRV data to assist the user in avoiding sleep.

U.S. Pat. No. 7,524,279 for sleep and environment control method and system by inventor Auphan, filed Dec. 29, 2004 and issued Apr. 28, 2009, is directed to a sleep system that includes sensors capable of gathering sleep data from a person and environmental data during a sleep by the person. A processor executes instructions that analyze this data and control the sleep of the person and the environment surrounding the person. Typically, the instructions are loaded in a memory where they execute to generate an objective measure of sleep quality from the sleep data from the person and gather environmental data during the sleep by the person. Upon execution, the instructions receive a subjective measure of sleep quality from the person after the sleep, create a sleep quality index from the objective measure of sleep quality and subjective measure of sleep quality, correlate the sleep quality index and a current sleep system settings with a historical sleep quality index and corresponding historical sleep system settings. The instructions then may modify the current set of sleep system settings depending on the correlation between the sleep quality index and the historic sleep quality index. These sleep system settings control and potentially change one or more different elements of an environment associated with the sleep system.

U.S. Pat. No. 7,608,041 for monitoring and control of sleep cycles by inventor Sutton, filed Apr. 20, 2007 and issued Oct. 27, 2009, is directed to a system including: a monitor for monitoring a user's sleep cycles; a processor which counts the sleep cycles to provide a sleep cycle count and which selects an awakening time according to a decision algorithm including the sleep cycle count as an input; and an alarm for awakening the user at the awakening time. Use of the sleep cycle count as an input to the decision algorithm advantageously enables a user to more fully control and optimize his or her personal sleeping behavior.

U.S. Pat. No. 7,699,785 for method for determining sleep stages by inventor Nemoto, filed Feb. 23, 2005 and issued Apr. 20, 2010, is directed to a method for determining sleep stages of an examinee, including detecting signals of the examinee with a biosignal detector, calculating a signal strength deviation value that indicates deviation of a signal strength of the detected signals, and determining a sleep stage by using the signal strength deviation value or a value of a plurality of values based on the signal strength deviation value as an indicator value.

U.S. Publication No. 20100100004 for skin temperature measurement in monitoring and control of sleep and alertness by inventor van Someren, filed Dec. 15, 2008 and published Apr. 22, 2010, is directed to a method of an arrangement for monitoring sleep in a subject by measuring within a prescribed interval skin temperature of a predetermined region of the subject's body and a motion sensor for sensing motion of the subject, comparing the measured skin temperature of the predetermined region with a predetermined temperature threshold, and classifying the subject as being asleep or awake based on whether the skin temperature of the predetermined region is above or below the temperature threshold and on the motion data. In alternative aspects the invention relates to methods of and arrangements for manipulating sleep, as well as monitoring or manipulating alertness.

U.S. Pat. No. 7,868,757 for method for the monitoring of sleep using an electronic device by inventors Radivojevic et al., filed Dec. 29, 2006 and issued Jan. 11, 2011, is directed to a method where sleep sensor signals are obtained to a mobile communication device from sensor devices. The mobile communication device checks the sleep sensor signals for a sleep state transition, determines the type of the sleep state transition, forms control signals based on the type of the sleep state transition and sends the control signals to at least one electronic device.

U.S. Publication No. 20110015495 for method and system for managing a user's sleep by inventors Dothie et al., filed Jul. 16, 2010 and published Jan. 20, 2011, is directed to a sleep management method and system for improving the quality of sleep of a user which monitors one or more objective parameters relevant to sleep quality of the user when in bed and receives from the user in waking hours via a portable device such as a mobile phone feedback from objective test data on cognitive and/or psychomotor performance.

U.S. Publication No. 20110230790 for method and system for sleep monitoring, regulation and planning by inventor Kozlov, filed Mar. 27, 2010 and published Sep. 22, 2011, is directed to a method for operating a sleep phase actigraphy synchronized alarm clock that communicates with a remote sleep database, such as an internet server database, and compares user physiological parameters, sleep settings, and actigraphy data with a large database that may include data collected from a large number of other users with similar physiological parameters, sleep settings, and actigraphy data. The remote server may use "black box" analysis approach by running supervised learning algorithms to analyze the database, producing sleep phase correction data which can be uploaded to the alarm clock, and be used by the alarm clock to further improve its REM sleep phase prediction accuracy.

U.S. Publication No. 20110267196 for system and method for providing sleep quality feedback by inventors Hu et al., filed May 3, 2011 and published Nov. 3, 2011, is directed to a system and method for providing sleep quality feedback that includes receiving alarm input on a base device from a user; the base device communicating an alarm setting based on the alarm input to an individual sleep device; the individual sleep device collecting sleep data based on activity input of a user; the individual sleep device communicating sleep data to the base device; the base device calculating sleep quality feedback from the sleep data; communicating sleep quality feedback to a user; and the individual sleep device activating an alarm, wherein activating the alarm includes generating tactile feedback to the user according to the alarm setting.

U.S. Pat. No. 8,096,960 for easy wake device by inventors Loree et al., filed Oct. 29, 2007 and issued Jan. 17, 2012, is directed to a device that monitors a user's sleep cycles and operates to sound an alarm to awaken the user at an optimal point within a sleep cycle. Once an alarm time is set and the alarm is activated, the device begins to monitor a wearer's sleep cycles by identifying the points in time at which the wearer moves his or her body limbs. As the alarm time is approached, the device can trigger the alarm earlier if the wearer is at an optimal point in the sleep cycle or, even retard the triggering of the alarm if the optimal point in the sleep cycle is expected to occur shortly. The device can be used to assist children in waking up to prevent bed wetting, or in a patient for obtaining light therapy.

U.S. Pat. No. 8,179,270 for methods and systems for providing sleep conditions by inventors Rai et al., filed Jul. 21, 2009 and issued May 15, 2012, is directed to a method for monitoring a sleep condition with a sleep scheduler wherein the method includes receiving a sleep parameter via an input receiver on the sleep scheduler. The method further includes associating the sleep parameter with an overall alertness and outputting a determined sleep condition based on the overall alertness. A system for providing a sleep condition is further disclosed therein the system comprising includes a display, an input receiver operable to receive a sleep parameter, and a processor in communication with the display. The processor may be operable to determine an overall alertness associated with the sleep parameter and wherein the processor is operable to output a determined sleep condition based on the overall alertness.

U.S. Pat. No. 8,290,596 for therapy program selection based on patient state by inventors Wei et al., filed Sep. 25, 2008 and issued Oct. 16, 2012, is directed to selecting a therapy program based on a patient state, where the patient state comprises at least one of a movement state, sleep state or speech state. In this way, therapy delivery is tailored to the patient state, which may include specific patient symptoms. The therapy program is selected from a plurality of stored therapy programs that comprise therapy programs associated with a respective one at least two of the movement, sleep, and speech states. Techniques for determining a patient state include receiving volitional patient input or detecting biosignals generated within the patient's brain. The biosignals are nonsymptomatic and may be incidental to the movement, sleep, and speech states or generated in response to volitional patient input.

U.S. Pat. No. 8,348,840 for device and method to monitor, assess and improve quality of sleep by inventors Heit et al., filed Feb. 4, 2010 and issued Jan. 8, 2013, is directed to a medical sleep disorder arrangement that integrates into current diagnosis and treatment procedures to enable a health care professional to diagnose and treat a plurality of subjects suffering from insomnia. The arrangement may include both environmental sensors and body-worn sensors that measure the environmental conditions and the condition of the individual patient. The data may be collected and processed to measure clinically relevant attributes of sleep quality automatically. These automatically determined measures, along with the original sensor data, may be aggregated and shared remotely with the health care professional. A communication apparatus enables the healthcare professional to remotely communicate with and further assess the patient and subsequently administer the treatment. Thus, a more accurate diagnosis and more effective treatment is provided while reducing the required clinician time per patient for treatment delivery.

U.S. Publication No. 20130060306 for efficient circadian and related system modulation with a sleep mask by inventor Colbauch, filed Apr. 25, 2011 and published Mar. 7, 2013, is directed to providing light therapy to a subject through a sleep mask. The sleep mask is configured to deliver electromagnetic radiation to the closed eyelids of the subject within a defined optimal wavelength band that is therapeutically impactful in modulating circadian and related systems of the subject.

U.S. Pat. No. 8,529,457 for system and kit for stress and relaxation management by inventors Devot et al., filed Aug. 20, 2010 and issued Sep. 10, 2013, is directed to a system and a kit for stress and relaxation management. A cardiac activity sensor is used for measuring the heart rate variability (HRV) signal of the user and a respiration sensor for measuring the respiratory signal of the user. The system contains a user interaction device having an input unit for receiving user specific data and an output unit for providing information output to the user. A processor is used to assess the stress level of the user by determining a user related stress index. The processor is also used to monitor the user during a relaxation exercise by means of determining a relaxation index based on the measured HRV and respiratory signals, the relaxation index being continuously adapted to the incoming measured signals and based thereon the processor instructs the output unit to provide the user with biofeedback and support messages. Finally, the processor uses the user specific data as an input in generating a first set of rules defining an improvement plan for self-management of stress and relaxation. The first set of rules is adapted to trigger commands instructing the output unit to provide the user with motivation related messages. Also, at least a portion of said user specific data is further used to define a second set of rules indicating the user's personal goals.

U.S. Publication No. 20130234823 for method and apparatus to provide an improved sleep experience by selecting an optimal next sleep state for a user by inventors Kahn et al., filed Feb. 28, 2013 and published Sep. 12, 2013, is directed to a sleep sensing system comprising a sensor to obtain real-time information about a user, a sleep state logic to determine the user's current sleep state based on the real-time information. The system further comprising a sleep stage selector to select an optimal next sleep state for the user, and a sound output system to output sounds to guide the user from the current sleep state to the optimal next sleep state.

U.S. Pat. No. 8,617,044 for stress reduction by inventors Pelgrim et al., filed Jun. 5, 2009 and issued Dec. 31, 2013, is directed to a method and system for reducing stress in a working environment. In a conditioning phase a positive association of a sensory stimulus, such as a scent, image and/or sound with a relaxed feeling is created. Following the creation of this positive association the "relaxing" stimulus will be used as a de-stressor in the usage phase. That is, when it is detected that the user is stressed, the "relaxing" stimulus is released to reduce stress.

U.S. Pat. No. 8,768,520 for systems and methods for controlling a bedroom environment and for providing sleep data by inventors Oexman et al., filed Nov. 14, 2008 and issued Jul. 1, 2014, is directed to a system for controlling a bedroom environment that includes an environmental data collector configured to collect environmental data relating to the bedroom environment; a sleep data collector configured to collect sleep data relating to a person's state of sleep; an analysis unit configured to analyze the collected environmental data and the collected sleep data and to determine an adjustment of the bedroom environment that promotes sleep of the person; and a controller configured to effect the adjustment of the bedroom environment. A method for controlling a bedroom environment includes collecting environmental data relating to the bedroom environment; collecting sleep data relating to a person's state of sleep; analyzing the collected environmental data and the collected sleep data; determining an adjustment to the bedroom environment that promotes sleep; and communicating the adjustment to a device that effects the bedroom environment.

U.S. Pat. No. 9,196,479 for methods and systems for gathering human biological signals and controlling a bed device by inventors Franceschetti et al., filed Jun. 5, 2015 and issued Nov. 17, 2015, is directed to methods and systems for an adjustable bed device configured to: gather biological signals associated with multiple users, such as heart rate, breathing rate, or temperature; analyze the gathered human biological signals; and heat or cool a bed based on the analysis.

U.S. Publication No. 20160151603 for methods and systems for sleep management by inventors Shouldice et al., filed Dec. 21, 2015 and published Jun. 2, 2016, is directed to a processing system including methods to promote sleep. The system may include a monitor such as a non-contact motion sensor from which sleep information may be determined. User sleep information, such as sleep stages, hypnograms, sleep scores, mind recharge scores and body scores, may be recorded, evaluated and/or displayed for a user. The system may further monitor ambient and/or environmental conditions corresponding to sleep sessions. Sleep advice may be generated based on the sleep information, user queries and/or environmental conditions from one or more sleep sessions. Communicated sleep advice may include content to promote good sleep habits and/or detect risky sleep conditions. In some versions of the system, any one or more of a bedside unit sensor module, a smart processing device, such as a smart phone or smart device, and network servers may be implemented to perform the methodologies of the system.

U.S. Publication No. 20170053068 for methods for enhancing wellness associated with habitable environments, filed Aug. 26, 2016 and published Feb. 23, 2017, is directed to controlling environmental characteristics of habitable environments (e.g., hotel or motel rooms, spas, resorts, cruise boat cabins, offices, hospitals and/or homes, apartments or residences) to eliminate, reduce or ameliorate adverse or harmful aspects and introduce, increase or enhance beneficial aspects in order to improve a "wellness" or sense of "wellbeing" provided via the environments. Control of intensity and wavelength distribution of passive and active illumination addresses various issues, symptoms or syndromes, for instance to maintain a circadian rhythm or cycle, adjust for "jet lag" or season affective disorder, etc. Air quality and attributes are controlled. Scent(s) may be dispersed. Noise is reduced and sounds (e.g., masking, music, natural) may be provided. Environmental and biometric feedback is provided. Experimentation and machine learning are used to improve health outcomes and wellness standards.

SUMMARY OF THE INVENTION

The present invention relates to articles, methods, and systems for stress reduction and sleep promotion.

In one embodiment, the present invention provides a stress reduction and sleep promotion system including at least one remote device and an article for adjusting a temperature of a surface, wherein the article further includes a first layer, wherein the first layer has an exterior surface and an interior surface, a second layer, wherein the second layer has an exterior surface and an interior surface, and wherein the second layer is permanently affixed to the first layer along a periphery of the article, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote device and the at least one control unit are in real-time or near-real-time two-way communication, wherein the at least one interior chamber is constructed and configured to retain the fluid without leaking, and wherein the interior surface of the first layer and the interior surface of the second layer are formed of at least one layer of a waterproof material.

In another embodiment, the present invention provides a stress reduction and sleep promotion system including at least one body sensor, at least one remote device, at least one remote server, and an article for adjusting a temperature of a surface, wherein the article further includes a first layer, wherein the first layer has an exterior surface and an interior surface, a second layer, wherein the second layer has an exterior surface and an interior surface, and wherein the second layer is permanently affixed to the first layer along a periphery of the article, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote server and the at least one remote device are in real-time or near-real-time two-way communication, wherein the at least one remote device and the at least one control unit are in real-time or near-real-time two-way communication, wherein the at least one remote server is operable to determine optimized parameters for the article based on data from the at least one body sensor, wherein the at least one remote server is operable to transmit the optimized parameters for the article to the at least one remote device, wherein the at least one remote device is operable to transmit the optimized parameters for the article to the at least one control unit, wherein the at least one interior chamber is constructed and configured to retain the fluid without leaking, and wherein the interior surface of the first layer and the interior surface of the second layer are comprised of at least one layer of a waterproof material.

In yet another embodiment, the present invention provides a stress reduction and sleep promotion system including at least one body sensor, at least one remote device, at least one remote server, a pulsed electromagnetic frequency device, wherein the pulsed electromagnetic frequency device further includes at least one inductor coil, a power supply coupled to a circuit that produces an alternating current (AC) or a direct current (DC) output that is transmitted to the at least one inductor coil, at least one antenna, and at least one processor, and an article for adjusting a temperature of a surface, wherein the article further includes a first layer, wherein the first layer has an exterior surface and an interior surface, a second layer, wherein the second layer has an exterior surface and an interior surface, and wherein the second layer is permanently affixed to the first layer along a periphery of the article, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote server and the at least one remote device are in real-time or near-real-time two-way communication, wherein the at least one remote device and the at least one control unit are in real-time or near-real-time two-way communication, wherein the at least one remote server is operable to determine optimized parameters for the article based on data from the at least one body sensor, wherein the at least one remote server is operable to transmit the optimized parameters for the article to the at least one remote device, wherein the at least one remote device is operable to transmit the optimized parameters for the article to the at least one control unit, wherein the at least one interior chamber is constructed and configured to retain the fluid without leaking, and wherein the interior surface of the first layer and the interior surface of the second layer are comprised of at least one layer of a waterproof material.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 25 shows a table of frequencies and the effects on tissues.

FIG. 46 illustrates a profile screen for one embodiment of a GUI for a mobile application allowing for segmented sleep.

FIG. 48 illustrates a treatment summary screen for one embodiment of a GUI for a mobile application.

DETAILED DESCRIPTION

Figure 1:
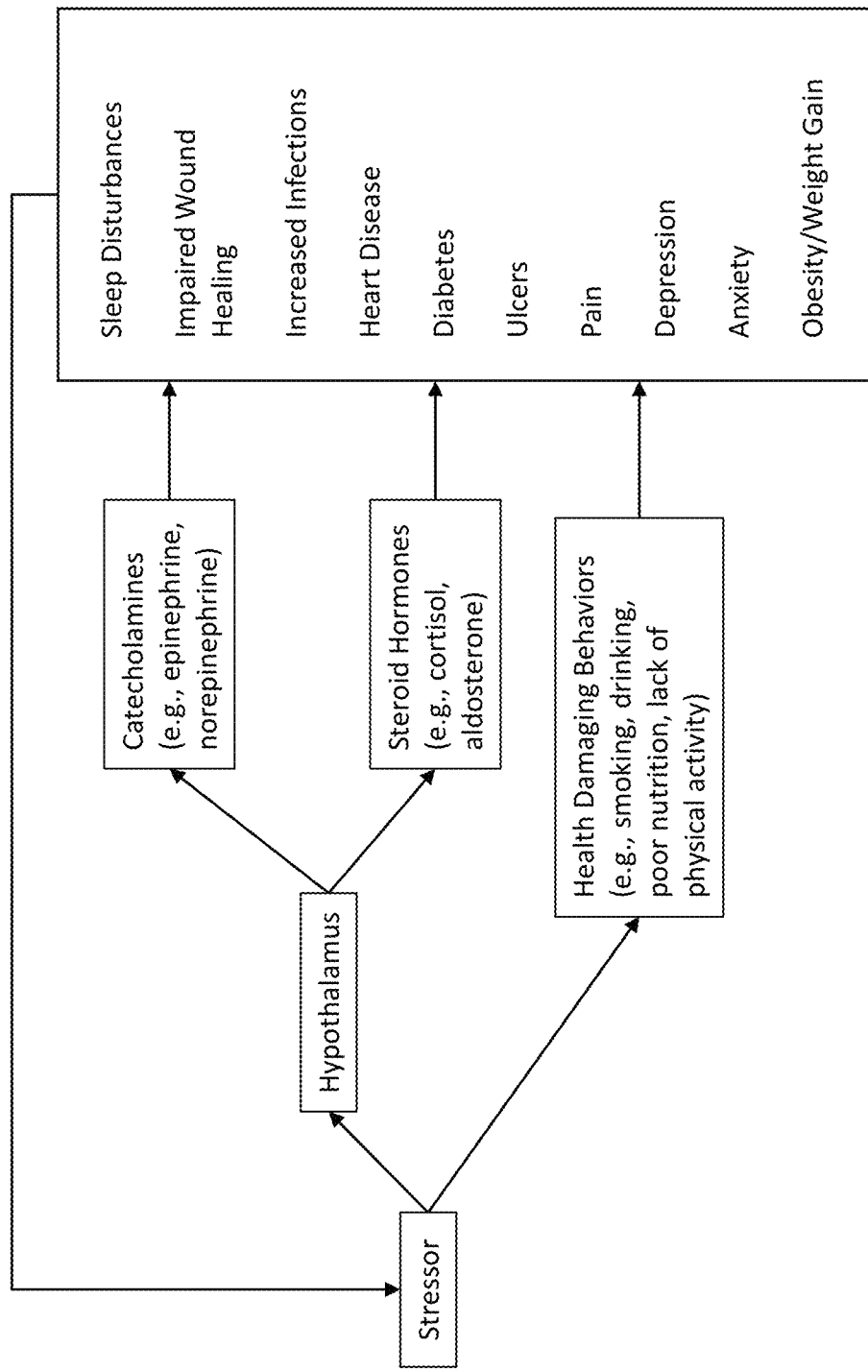
FIG. 1 illustrates the effects of a stressor on the body.

The present invention is generally directed to articles, methods, and systems for stress reduction and sleep promotion.

In one embodiment, the present invention provides a stress reduction and sleep promotion system including at least one remote device and an article for adjusting a temperature of a surface, wherein the article further includes a first layer, wherein the first layer has an exterior surface and an interior surface, a second layer, wherein the second layer has an exterior surface and an interior surface, and wherein the second layer is permanently affixed to the first layer along a periphery of the article, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote device and the at least one control unit are in real-time or near-real-time two-way communication, wherein the at least one interior chamber is constructed and configured to retain the fluid without leaking, and wherein the interior surface of the first layer and the interior surface of the second layer are formed of at least one layer of a waterproof material.

In another embodiment, the present invention provides a stress reduction and sleep promotion system including at least one body sensor, at least one remote device, at least one remote server, and an article for adjusting a temperature of a surface, wherein the article further includes a first layer, wherein the first layer has an exterior surface and an interior surface, a second layer, wherein the second layer has an exterior surface and an interior surface, and wherein the second layer is permanently affixed to the first layer along a periphery of the article, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote server and the at least one remote device are in real-time or near-real-time two-way communication, wherein the at least one remote device and the at least one control unit are in real-time or near-real-time two-way communication, wherein the at least one remote server is operable to determine optimized parameters for the article based on data from the at least one body sensor, wherein the at least one remote server is operable to transmit the optimized parameters for the article to the at least one remote device, wherein the at least one remote device is operable to transmit the optimized parameters for the article to the at least one control unit, wherein the at least one interior chamber is constructed and configured to retain the fluid without leaking, and wherein the interior surface of the first layer and the interior surface of the second layer are comprised of at least one layer of a waterproof material.

In yet another embodiment, the present invention provides a stress reduction and sleep promotion system including at least one body sensor, at least one remote device, at least one remote server, a pulsed electromagnetic frequency device, wherein the pulsed electromagnetic frequency device further includes at least one inductor coil, a power supply coupled to a circuit that produces an alternating current (AC) or a direct current (DC) output that is transmitted to the at least one inductor coil, at least one antenna, and at least one processor, and an article for adjusting a temperature of a surface, wherein the article further includes a first layer, wherein the first layer has an exterior surface and an interior surface, a second layer, wherein the second layer has an exterior surface and an interior surface, and wherein the second layer is permanently affixed to the first layer along a periphery of the article, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote server and the at least one remote device are in real-time or near-real-time two-way communication, wherein the at least one remote device and the at least one control unit are in real-time or near-real-time two-way communication, wherein the at least one remote server is operable to determine optimized parameters for the article based on data from the at least one body sensor, wherein the at least one remote server is operable to transmit the optimized parameters for the article to the at least one remote device, wherein the at least one remote device is operable to transmit the optimized parameters for the article to the at least one control unit, wherein the at least one interior chamber is constructed and configured to retain the fluid without leaking, and wherein the interior surface of the first layer and the interior surface of the second layer are comprised of at least one layer of a waterproof material.

None of the prior art discloses an article for adjusting the temperature of a surface formed from a first layer and a second layer, wherein the second layer is permanently affixed to the first layer along a periphery of the article, and wherein at least one interior chamber constructed and configured to retain a fluid without leaking is defined between an interior surface of the first layer and an interior surface of the second layer. Further, none of the prior art discloses using such an article in a stress reduction and sleep promotion system to programmatically control target temperatures over time, such as over the course of a night's sleep, using at least one remote device. Additionally, none of the prior art discloses using such an article in a stress reduction and sleep promotion system with at least one body sensor, wherein optimized parameters for the article are based on data from the at least one body sensor. Finally, none of the prior art discloses using such an article in a stress reduction and sleep promotion system with at least one body sensor and a pulsed electromagnetic frequency device.

Several studies show a link between stress and illness. Stress may cause physiological changes and lead individuals to adopt health damaging behaviors (e.g., smoking, drinking, poor nutrition, lack of physical activity). These physiological changes and health damaging behaviors can cause illnesses, such as sleep disturbances, impaired wound healing, increased infections, heart disease, diabetes, ulcers, pain, depression, and obesity or weight gain.

The body reacts to stress through two systems: the autonomic nervous system and the hypothalamic-pituitary-adrenal (HPA) axis. The autonomic nervous system, which consists of the sympathetic nervous system and the parasympathetic nervous system, is responsible for reacting to short term ("acute") stress. In response to short term stress, the sympathetic nervous system activates the "fight or flight response" through the sympathoadrenal medullary (SAM) axis. This causes the adrenal medulla to secrete catecholamines (e.g., epinephrine and norepinephrine), which causes blood glucose levels to rise, blood vessels to constrict, heart rate to increase, and blood pressure to rise. Blood is diverted from nonessential organs to the heart and skeletal muscles, which leads to decreased digestive system activity and reduced urine output. Additionally, the metabolic rate increases and bronchioles dilate. The parasympathetic nervous system then returns the body to homeostasis.

The HPA axis is responsible for reacting to long term ("chronic") stress. This causes the adrenal cortex to secrete steroid hormones (e.g., mineralocorticoids and glucocorticoids). Mineralocorticoids (e.g., aldosterone) cause retention of sodium and water by the kidneys, increased blood pressure, and increased blood volume. Glucocorticoids (e.g., cortisol) cause proteins and fats to be converted to glucose or broken down for energy, increased blood glucose, and suppression of the immune system.

Thus, stress impacts the body on a cellular level and is a precursor to many disease states. Therefore, it is important to manage and treat stress to maintain health. However, as a result of modern lifestyles, most people are busy, tired, and stressed out. Most people also lack the time and energy to obtain treatments for minor ailments or treatments to prevent disease. What is needed is a convenient treatment that reduces stress and inflammation and promotes healing.

Energy medicine (e.g., biofield therapies, bioelectromagnetic therapies, acupuncture, homeopathy) focuses on the principle that small changes repeated over time can change the dynamics of the body and stimulate healing. The present invention utilizes that principle to reduce stress, promote sleep, and stimulate healing. Further, the present invention reduces stress and stimulates healing while a user is resting or sleeping, which is convenient for the user and allows a focused time (e.g., 6-9 hours during a sleeping period) for the user to heal while at home.

Referring now to the drawings in general, the illustrations are for the purpose of describing a preferred embodiment of the invention and are not intended to limit the invention thereto.

FIG. 1 illustrates the effects of a stressor on the body. The body releases catecholamines or steroid hormones as a physiological response to the stressor. Stress may also lead individuals to adopt health damaging behaviors (e.g., smoking, drinking, poor nutrition, lack of physical activity). This may lead to illnesses, such as sleep disturbances, impaired wound healing, increased infections, heart disease, diabetes, ulcers, pain, depression, anxiety, and/or obesity or weight gain. These illnesses themselves may become a stressor, which triggers the cycle to continue and causes further physical and mental problems.

Figure 2:
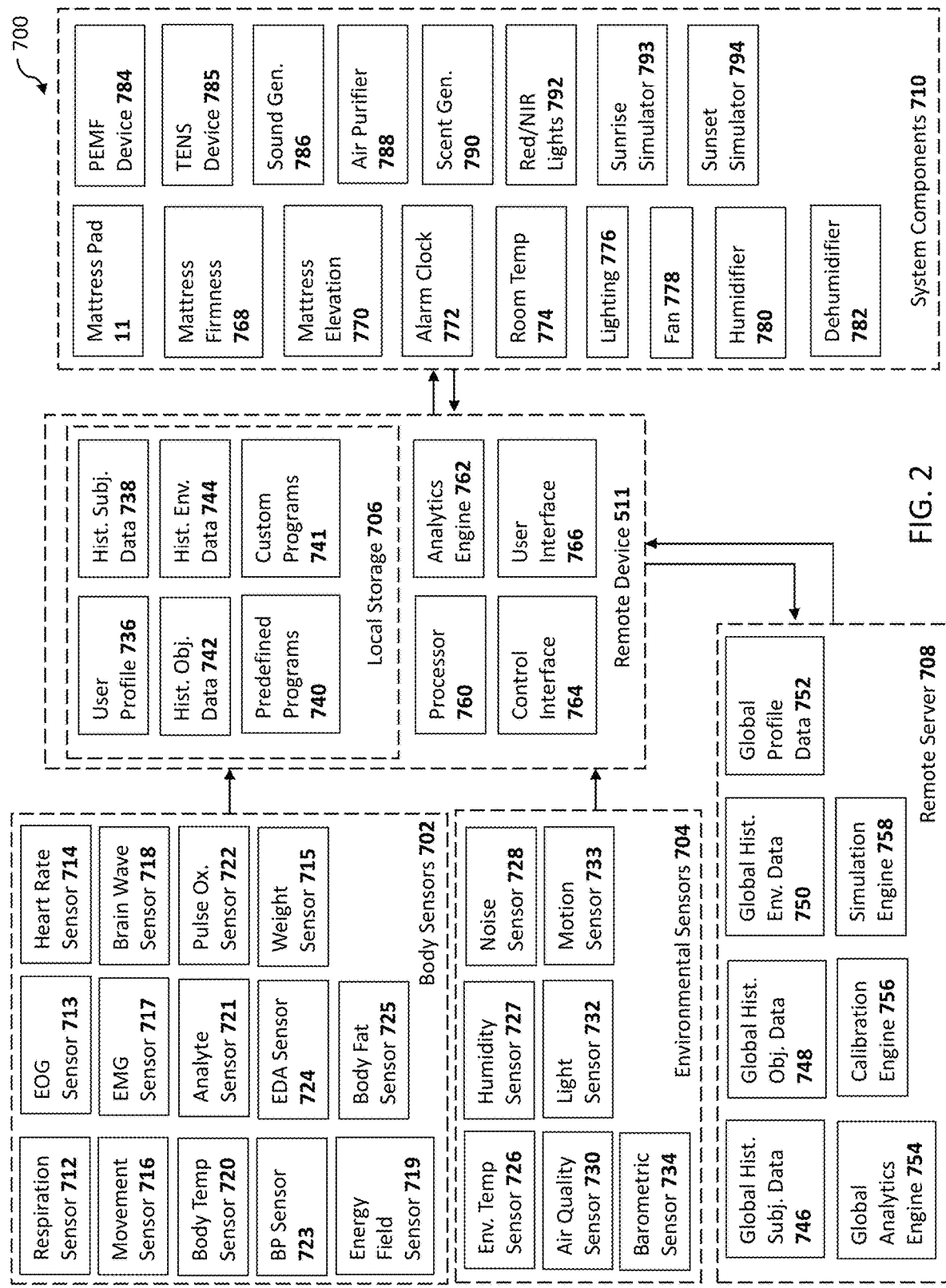
FIG. 2 is a block diagram of one embodiment of the stress reduction and sleep promotion system.

FIG. 2 is a block diagram of one embodiment of the stress reduction and sleep promotion system. The stress reduction and sleep promotion system 700 includes body sensors 702, environmental sensors 704, a remote device 511 with local storage 706, a remote server 708, and system components 710. The body sensors 702 include a respiration sensor 712, an electrooculography (EOG) sensor 713, a heart rate sensor 714, a body weight sensor 715, a movement sensor 716, an electromyography (EMG) sensor 717, a brain wave sensor 718, a body temperature sensor 720, an analyte sensor 721, a pulse oximeter sensor 722, a blood pressure (BP) sensor 723, an electrodermal activity (EDA) sensor 724, and/or a body fat sensor 725.

The respiration sensor 712 measures a respiratory rate. In one embodiment, the respiration sensor 712 is incorporated into a wearable device (e.g., a chest strap). In another embodiment, the respiration sensor 712 is incorporated into a patch or a bandage. Alternatively, the respiratory rate is estimated from an electrocardiogram, a photoplethysmogram (e.g., a pulse oximeter), and/or an accelerometer. In yet another embodiment, the respiratory sensor 712 uses a non-contact motion biomotion sensor to monitor respiration.

The electrooculography (EOG) sensor 713 measures the corneo-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position.

The heart rate sensor 714 is preferably incorporated into a wearable device (e.g., Fitbit®, Jawbone®). Alternatively, the heart rate sensor 714 is attached to the user with a chest strap. In another embodiment, the heart rate sensor 714 is incorporated into a patch or a bandage. In yet another embodiment, the heart rate sensor is incorporated into a sensor device on or under the mattress (e.g., Beddit®, Emfit® QS™). The heart rate is determined using electrocardiography, pulse oximetry, ballistocardiography, or seismocardiography. In one embodiment, the heart rate sensor 714 measures heart rate variability (HRV). HRV is a measurement of the variation in time intervals between heartbeats. A high HRV measurement is indicative of less stress, while a low HRV measurement is indicative of more stress. Studies have linked abnormalities in HRV to diseases where stress is a factor (e.g., diabetes, depression, congestive heart failure). In one embodiment, a Poincaré plot is generated to display HRV on a device such as a smartphone.

The body weight sensor 715 is preferably a smart scale (e.g., Fitbit® Aria®, Nokia® Body+, Garmin® Index™, Under Armour® Scale, Pivotal Living® Smart Scale, iHealth® Core). Alternatively, the body weight sensor 715 is at least one pressure sensor embedded in a mattress or a mattress topper. In one embodiment, the stress reduction and sleep promotion system 700 is also operable to determine a height of a user using the at least one pressure sensor embedded in a mattress or a mattress topper. In another embodiment, a body mass index (BMI) of the user is calculated using the body weight of the user and the height of the user as measured by the at least one pressure sensor.

The movement sensor 716 is an accelerometer and/or a gyroscope. In one embodiment, the accelerometer and/or the gyroscope are incorporated into a wearable device (e.g., Fitbit®, Jawbone®, actigraph). In another embodiment, the accelerometer and/or the gyroscope are incorporated into a smartphone. In alternative embodiment, the movement sensor 716 is a non-contact sensor. In one embodiment, the movement sensor 716 is at least one piezoelectric sensor. In another embodiment, the movement sensor 716 is a pyroelectric infrared sensor (i.e., a "passive" infrared sensor). In yet another embodiment, the movement sensor 716 is at least one pressure sensor embedded in a mattress or mattress topper. Alternatively, the movement sensor 716 is incorporated into a smart fabric.

The electromyography (EMG) sensor 717 records the electrical activity produced by skeletal muscles. Impulses are recorded by attaching electrodes to the skin surface over the muscle. In a preferred embodiment, three electrodes are placed on the chin. One in the front and center and the other two underneath and on the jawbone. These electrodes demonstrate muscle movement during sleep, which can be used to detect REM or NREM sleep. In another embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg can be used to detect movement of the legs during sleep, which may occur with Restless Leg Syndrome or Periodic Limb Movements of Sleep.

The brain wave sensor 718 is preferably an electroencephalogram (EEG) with at least one channel. In a preferred embodiment, the EEG has at least two channels. Multiple channels provide higher resolution data. The frequencies in EEG data indicate particular brain states. The brain wave sensor 718 is preferably operable to detect delta, theta, alpha, beta, and gamma frequencies. In another embodiment, the brain wave sensor 718 is operable to identify cognitive and emotion metrics, including focus, stress, excitement, relaxation, interest, and/or engagement. In yet another embodiment, the brain wave sensor 718 is operable to identify cognitive states that reflect the overall level of engagement, attention and focus and/or workload that reflects cognitive processes (e.g., working memory, problem solving, analytical reasoning).

The energy field sensor 719 measures an energy field of a user. In one embodiment, the energy field sensor 719 is a gas discharge visualization (GDV) device. Examples of a GDV device are disclosed in U.S. Pat. Nos. 7,869,636 and 8,321,010 and U.S. Publication No. 20100106424, each of which is incorporated herein by reference in its entirety. The GDV device utilizes the Kirlian effect to evaluate an energy field. In a preferred embodiment, the GDV device utilizes a high-intensity electric field (e.g., 1024 Hz, 10 kV, square pulses) input to an object (e.g., human fingertips) on an electrified glass plate. The high-intensity electric field produces a visible gas discharge glow around the object (e.g., fingertip). The visible gas discharge glow is detected by a charge-coupled detector and analyzed by software on a computer. The software characterizes the pattern of light emitted (e.g., brightness, total area, fractality, density). In a preferred embodiment, the software utilizes Mandel's Energy Emission Analysis and the Su-Jok system of acupuncture to create images and representations of body systems. The energy field sensor 719 is preferably operable to measure stress levels, energy levels, and/or a balance between the left and right sides of the body.

The body temperature sensor 720 measures core body temperature and/or skin temperature. The body temperature sensor 720 is a thermistor, an infrared sensor, or thermal flux sensor. In one embodiment, the body temperature sensor 720 is incorporated into an armband or a wristband. In another embodiment, the body temperature sensor 720 is incorporated into a patch or a bandage. In yet another embodiment, the body temperature sensor 720 is an ingestible core body temperature sensor (e.g., CorTemp®). The body temperature sensor 720 is preferably wireless.

The analyte sensor 721 monitors levels of an analyte in blood, sweat, or interstitial fluid. In one embodiment, the analyte is an electrolyte, a small molecule (molecular weight<900 Daltons), a protein (e.g., C-reactive protein), and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). The analyte sensor 721 is preferably non-invasive. Alternatively, the analyte sensor 721 is minimally invasive or implanted. In one embodiment, the analyte sensor 721 is incorporated into a wearable device. Alternatively, the analyte sensor 721 is incorporated into a patch or a bandage.

The pulse oximeter sensor 722 monitors oxygen saturation. In one embodiment, the pulse oximeter sensor 722 is worn on a finger, a toe, or an ear. In another embodiment, the pulse oximeter sensor 722 is incorporated into a patch or a bandage. The pulse oximeter sensor 722 is preferably wireless. Alternatively, the pulse oximeter sensor 722 is wired. In one embodiment, the pulse oximeter sensor 722 is connected by a wire to a wrist strap or a strap around a hand. In another embodiment, the pulse oximeter sensor 722 is combined with a heart rate sensor 714. In yet another embodiment, the pulse oximeter sensor 722 uses a camera lens on a smartphone or a tablet.

The blood pressure (BP) sensor 723 is a sphygmomanometer. The sphygmomanometer is preferably wireless. Alternatively, the blood pressure sensor 723 estimates the blood pressure without an inflatable cuff (e.g., Salu™ Pulse+). In one embodiment, the blood pressure sensor 723 is incorporated into a wearable device.

The electrodermal activity sensor 724 measures sympathetic nervous system activity. Electrodermal activity is more likely to have high frequency peak patterns (i.e., "storms") during deep sleep. In one embodiment, the electrodermal activity sensor 724 is incorporated into a wearable device. Alternatively, the electrodermal activity sensor 724 is incorporated into a patch or a bandage.

The body fat sensor 725 is preferably a bioelectrical impedance device. In one embodiment, the body fat sensor 725 is incorporated into a smart scale (e.g., Fitbit® Aria®, Nokia® Body+, Garmin® Index™, Under Armour® Scale, Pivotal Living® Smart Scale, iHealth® Core). Alternatively, the body fat sensor 725 is a handheld device.

The environmental sensors 704 include an environmental temperature sensor 726, a humidity sensor 727, a noise sensor 728, an air quality sensor 730, a light sensor 732, a motion sensor 733, and/or a barometric sensor 734. In one embodiment, the environmental temperature sensor 726, the humidity sensor 727, the noise sensor 728, the air quality sensor 730, the light sensor 732, the motion sensor 733, and/or the barometric sensor 734 are incorporated into a home automation system (e.g., Amazon® Alexa®, Apple® HomeKit™, Google® Home™ IF This Then That® (IFTTT®), Nest®). Alternatively, the environmental temperature sensor 726, the humidity sensor 727, the noise sensor 728, and/or the light sensor 732 are incorporated into a smartphone or tablet. In one embodiment, the noise sensor 728 is a microphone. In one embodiment, the air quality sensor 730 measures carbon monoxide, carbon dioxide, nitrogen dioxide, sulfur dioxide, particulates, and/or volatile organic compounds (VOCs).

The remote device 511 is preferably a smartphone or a tablet. Alternatively, the remote device 511 is a laptop or a desktop computer. The remote device 511 includes a processor 760, an analytics engine 762, a control interface 764, and a user interface 766. The remote device 511 accepts data input from the body sensors 702 and/or the environmental sensors 704. The remote device also accepts data input from the remote server 708. The remote device 511 stores data in a local storage 706.

The local storage 706 on the remote device 511 includes a user profile 736, historical subjective data 738, predefined programs 740, custom programs 741, historical objective data 742, and historical environmental data 744. The user profile 736 stores stress reduction and sleep promotion system preferences and information about the user, including but not limited to, age, weight, height, gender, medical history (e.g., sleep conditions, medications, diseases), fitness (e.g., fitness level, fitness activities), sleep goals, stress level, and/or occupational information (e.g., occupation, shift information). The medical history includes caffeine consumption, alcohol consumption, tobacco consumption, use of prescription sleep aids and/or other medications, blood pressure, restless leg syndrome, narcolepsy, headaches, heart disease, sleep apnea, depression, stroke, diabetes, insomnia, anxiety or post-traumatic stress disorder (PTSD), and/or neurological disorders.

In one embodiment, the medical history incorporates information gathered from the Epworth Sleepiness Scale (ESS), the Insomnia Severity Index (ISI), Generalized Anxiety Disorder 7-item (GAD-7) Scale, and/or Patient Heath Questionnaire-9 (PHQ-9) (assessment of depression). The ESS is described in Johns M W (1991). "*A new method for measuring daytime sleepiness: the Epworth sleepiness scale*", *Sleep,* 14 (6): 540-5 which is incorporated herein by reference in its entirety. The ISI is described in Morin et al. (2011). "The Insomnia Severity Index: Psychometric Indicators to Detect Insomnia Cases and Evaluate Treatment Response", *Sleep,* 34(5): 60E-608, which is incorporated herein by reference in its entirety. The GAD-7 described in Spitzer et al., "A brief measure for assessing generalized anxiety disorder: the GAD-7*", Arch Intern Med.,* 2006 May 22; 166(1):1092-7, which is incorporated herein by reference in its entirety. The PHQ-9 is described in Kroenke et al., "The PHQ-9: Validity of a Brief Depression Severity Measure", *J. Gen. Intern. Med.,* 2001 September; 16(9): 606-613, which is incorporated herein by reference in its entirety.

In one embodiment, the weight of the user is automatically uploaded to the local storage from a third-party application. In one embodiment, the third-party application obtains the information from a smart scale (e.g., Fitbit® Aria®, Nokia® Body+™ Garmin® Index™ Under Armour® Scale, Pivotal Living® Smart Scale, iHealth® Core). In another embodiment, the medical history includes information gathered from a Resting Breath Hold test.

The historical objective data 742 includes information gathered from the body sensors 702. This includes information from the respiration sensor 712, the electrooculography sensor 713, the heart rate sensor 714, the movement sensor 716, the electromyography sensor 717, the brain wave sensor 718, the energy field sensor 719, the body temperature sensor 720, the analyte sensor 721, the pulse oximeter sensor 722, the blood pressure sensor 723, and/or the electrodermal activity sensor 724. In another embodiment, the historical objective data 742 includes information gathered from the Maintenance of Wakefulness Test, the Digit Symbol Substitution Test, and/or the Psychomotor Vigilance Test. The Maintenance of Wakefulness Test is described in Doghramji, et al., "A normative study of the maintenance of wakefulness test (MWT)", *Electroencephalogr. Clin. Neurophysiol.,* 1997 November; 103(5): 554-562, which is incorporated herein by reference in its entirety. The Digit Symbol Substitution Test is described in Wechsler, D. (1997). Wechsler Adult Intelligence Scale—Third edition (WAIS-III). San Antonio, Tex.: Psychological Corporation and Wechsler, D. (1997). Wechsler Memory Scale—Third edition (WMS-III). San Antonio, Tex.: Psychological Corporation, each of which is incorporated herein by reference in its entirety. The Psychomotor Vigilance Test is described in Basner et al., "Maximizing sensitivity of the psychomotor vigilance test (PVT) to sleep loss", *Sleep,* 2011 May 1; 34(5): 581-91, which is incorporated herein by reference in its entirety.

The historical environmental data 744 includes information gathered from the environmental sensors 704. This includes information from the environmental temperature sensor 726, the humidity sensor 727, the noise sensor 728, the air quality sensor 730, the light sensor 732, and/or the barometric sensor 734.

The historical subjective data 738 includes information regarding sleep and/or stress. In one embodiment, the information regarding sleep is gathered from manual sleep logs (e.g., Pittsburgh Sleep Quality Index). The manual sleep logs include, but are not limited to, a time sleep is first attempted, a time to fall asleep, a time of waking up, hours of sleep, number of awakenings, times of awakenings, length of awakenings, perceived sleep quality, use of medications to assist with sleep, difficulty staying awake and/or concentrating during the day, difficulty with temperature regulation at night (e.g., too hot, too cold), trouble breathing at night (e.g., coughing, snoring), having bad dreams, waking up in the middle of the night or before a desired wake up time, twitching or jerking in the legs while asleep, restlessness while asleep, difficulty sleeping due to pain, and/or needing to use the bathroom in the middle of the night. The Pittsburgh Sleep Quality Index is described in Buysse, et al., "The Pittsburgh sleep quality index: A new instrument for psychiatric practice and research". *Psychiatry Research.* 28 (2): 193-213 (May 1989), which is incorporated herein by reference in its entirety.

In another embodiment, the historical subjective data 738 includes information gathered regarding sleepiness (e.g., Karolinska Sleepiness Scale, Stanford Sleepiness Scale, Epworth Sleepiness Scale). The Karolinska Sleepiness Scale is described in Åkerstedt, et al., "Subjective and objective sleepiness in the active individual", *Int J Neurosc.,* 1990; 52:29-37 and Baulk et al., "Driver sleepiness—evaluation of reaction time measurement as a secondary task", *Sleep,* 2001; 24(6):695-698, each of which is incorporated herein by reference in its entirety. The Stanford Sleepiness Scale is described in Hoddes E. (1972). "The development and use of the stanford sleepiness scale (SSS)". *Psychophysiology.* 9 (150) and Maclean, et al. (1992-03-01). "*Psychometric evaluation of the Stanford Sleepiness Scale". Journal of Sleep Research.* 1 (1): 35-39, each of which is incorporated herein by reference in its entirety.

In yet another embodiment, the historical subjective data 738 includes information regarding tension or anxiety, depression or dejection, anger or hostility, and/or fatigue or inertia gathered from the Profile of Mood States. The Profile of Mood States is described in the Profile of Mood States, 2$^{nd}$ Edition published by Multi-Health Systems (2012) and Curran et al., "Short Form of the Profile of Mood States (POMS-SF): Psychometric information", *Psychological Assessment.* 7 (1): 80-83 (1995), each of which is incorporated herein by reference in its entirety. In another embodiment, the historical subjective data 738 includes information gathered from the Ford Insomnia Response to Stress Test (FIRST), which asks how likely a respondent is to have difficulty sleeping in nine different situations. The FIRST is described in Drake et al., "Vulnerability to stress-related sleep disturbance and hyperarousal", *Sleep,* 2004; 27:285-91 and Drake et al., "Stress-related sleep disturbance and polysomnographic response to caffeine", *Sleep Med.,* 2006; 7:567-72, each of which is incorporated herein by reference in its entirety. In still another embodiment, the historical subjective data 738 includes information gathered from the Impact of Events, which assesses the psychological impact of stressful life events. A subscale score is calculated for intrusion, avoidance, and/or hyperarousal. The Impact of Events is described in Weiss, D. S., & Marmar, C. R. (1996). The Impact of Event Scale—Revised. In J. Wilson & T. M.

Keane (Eds.), Assessing psychological trauma and PTSD (pp. 399-411). New York: Guilford, which is incorporated herein by reference in its entirety. In one embodiment, the historical subjective data 738 includes information gathered from the Social Readjustment Rating Scale (SRRS). The SRRS lists 52 stressful life events and assigns a point value based on how traumatic the event was determined to be by a sample population. The SRRS is described in Holmes et al., "The Social Readjustment Rating Scale", *J. Psychosom. Res.* 11(2): 213-8 (1967), which is incorporated herein by reference in its entirety.

The predefined programs 740 are general sleep settings for various conditions and/or body types (e.g., weight loss, comfort, athletic recovery, hot flashes, bed sores, depression, multiple sclerosis, alternative sleep cycles). In one embodiment, a weight loss predefined program sets a surface temperature at a very cold setting (e.g., 15.56-18.89° C. (60-66° F.)) to increase a metabolic response, resulting in an increase in calories burned, which then leads to weight loss. Temperature settings are automatically adjusted to be as cold as tolerable by the user after the first sleep cycle starts to maximize the caloric burn while having the smallest impact on sleep quality. The core temperature of an overweight individual may fail to drop due to a low metabolism. In one example, the surface temperature is 20° C. (68° F.) at the start of a sleep period, 18.89° C. (66° F.) during N1-N2 sleep, 18.33° C. (65° F.) during N3 sleep, 19.44° C. (67° F.) during REM sleep, and 20° C. (68° F.) to wake the user.

In yet another embodiment, temperature modulation cycles are used to reduce insomnia. Insomnia may be caused by the core body temperature failing to drop or a delay of the drop in core body temperature. In one example, the surface temperature is 20° C. (68° F.) at the start of a sleep period, 17.78° C. (64° F.) during N1-N2 sleep, 15.56° C. (60° F.) during N3 sleep, 18.89° C. (66° F.) during REM sleep, and 20° C. (68° F.) to wake the user.

In still another embodiment, temperature modulation cycles are used to reduce sleep disruptions due to multiple sclerosis (MS). In MS, core temperature and extremity temperature management are not consistent. As a result, a warm to sleep and warm to wake is suggested. In one example, the surface temperature is 37.78° C. (100° F.) at the start of a sleep period, 21.11° C. (70° F.) during N1-N2 sleep, 20° C. (68° F.) during N3 sleep, 26.67° C. (80° F.) during REM sleep, and 37.78° C. (100° F.) to wake the user.

In yet another embodiment, temperature modulation cycles are used to support users with alternative sleep cycles. An alternative sleep cycle is when a user changes to a multiple phase sleep cycle in a 24-hour cycle (e.g., biphasic, segmented, polyphasic sleep). In one example, the surface temperature is 21.11° C. (70° F.) at the start of a sleep period, 17.78° C. (64° F.) during N1-N2 sleep, 16.67° C. (62° F.) during N3 sleep, 19.44° C. (67° F.) during REM sleep, and 21.11° C. (70° F.) to wake the user. This program can repeat for multiple, evenly spaced sleep blocks or be used in a longer block of 4-5 hours. For a short 30-minute block, the temperature drops (e.g., 0.278° C./minute (0.5° F./minute) or greater).

In one embodiment, temperature modulation cycles are used to reduce bed sores. The temperature modulation cycles alternate cooling and heating based on automated collection of risk factors, including temperature, surface area pressure, and moisture (e.g., sweat). In another embodiment, temperature modulation cycles are prescribed by a sleep specialist or physician based on a particular health condition of a user.

The custom programs 741 are sleep settings defined by the user. In one example, the user creates a custom program by modifying a predefined program (e.g., the weight loss program above) to be 1.11° C. (2° F.) cooler during the N3 stage. In another example, the user creates a custom program by modifying a predefined program (e.g., the weight loss program above) to have a start temperature of 37.78° C. (100° F.). The custom programs 741 allow a user to save preferred sleep settings.

The remote server 708 includes global historical subjective data 746, global historical objective data 748, global historical environmental data 750, global profile data 752, a global analytics engine 754, a calibration engine 756, and a simulation engine 758. The global historical subjective data 746, the global historical objective data 748, the global historical environmental data 750, and the global profile data 752 include data from multiple users.

The system components include a mattress pad 11 with adjustable temperature control, a mattress with adjustable firmness 768, a mattress with adjustable elevation 770, an alarm clock 772, a thermostat to adjust the room temperature 774, a lighting system 776, a fan 778, a humidifier 780, a dehumidifier 782, a pulsed electromagnetic field (PEMF) device 784, a transcutaneous electrical nerve stimulation (TENS) device 785, a sound generator 786, an air purifier 788, a scent generator 790, a red light and/or near-infrared lighting device 792, a sunrise simulator 793, and/or a sunset simulator 794.

The body sensors 702, the environmental sensors 704, the remote device 511 with local storage 706, the remote server 708, and the system components 710 are designed to connect directly (e.g., Universal Serial Bus (USB) or equivalent) or wirelessly (e.g., Bluetooth®, Wi-Fi®, ZigBee®) through systems designed to exchange data between various data collection sources. In a preferred embodiment, the body sensors 702, the environmental sensors 704, the remote device 511 with local storage 706, the remote server 708, and the system components 710 communicate wirelessly through Bluetooth®. Advantageously, Bluetooth® emits lower electromagnetic fields (EMFs) than Wi-Fi® and cellular signals.

Mattress Pad

Figure 3:
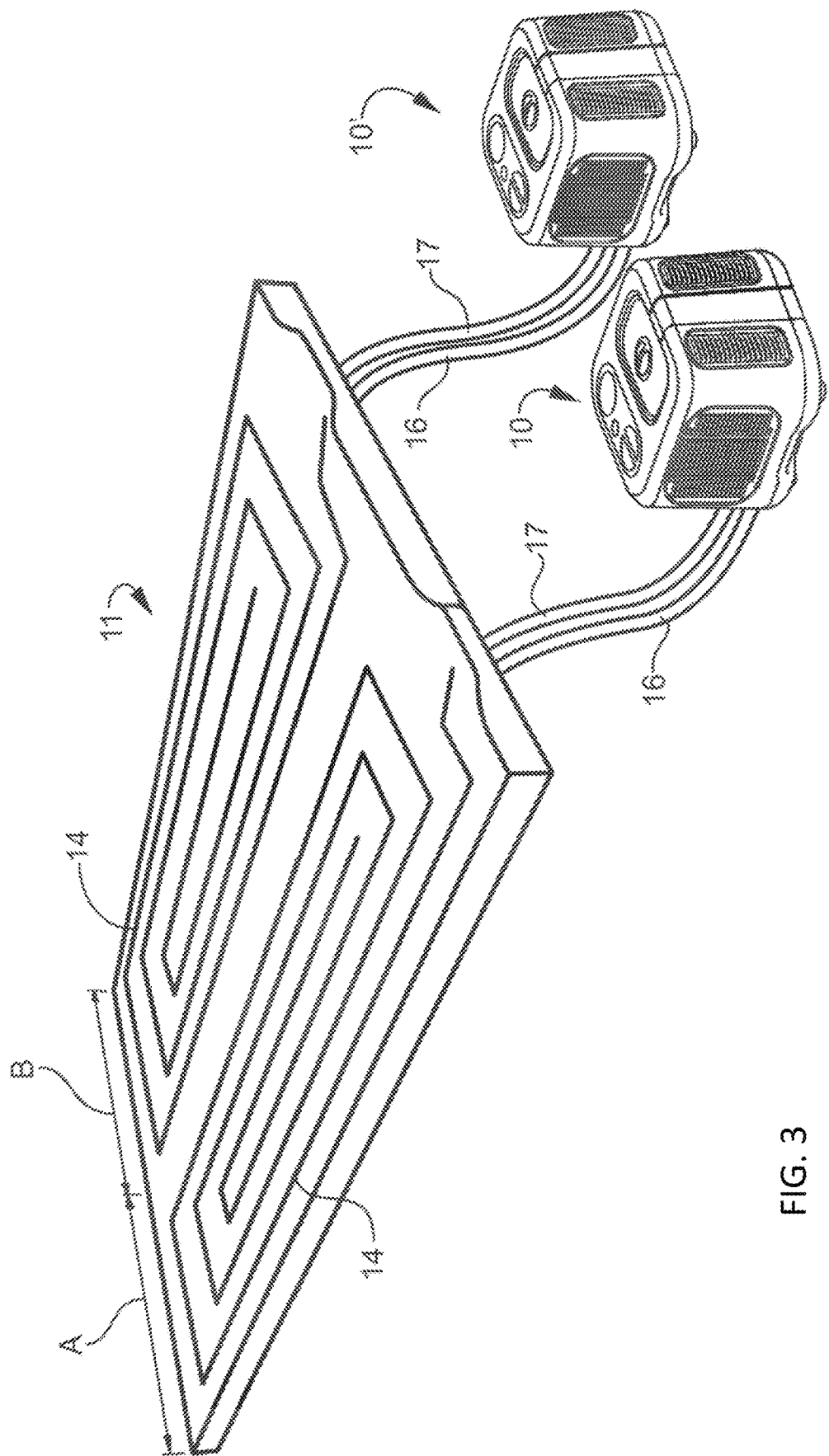
FIG. 3 is an environmental perspective view of a temperature-regulated mattress pad having two surface temperature zones connected to respective thermoelectric control units according to one exemplary embodiment of the present invention.
Figure 4:
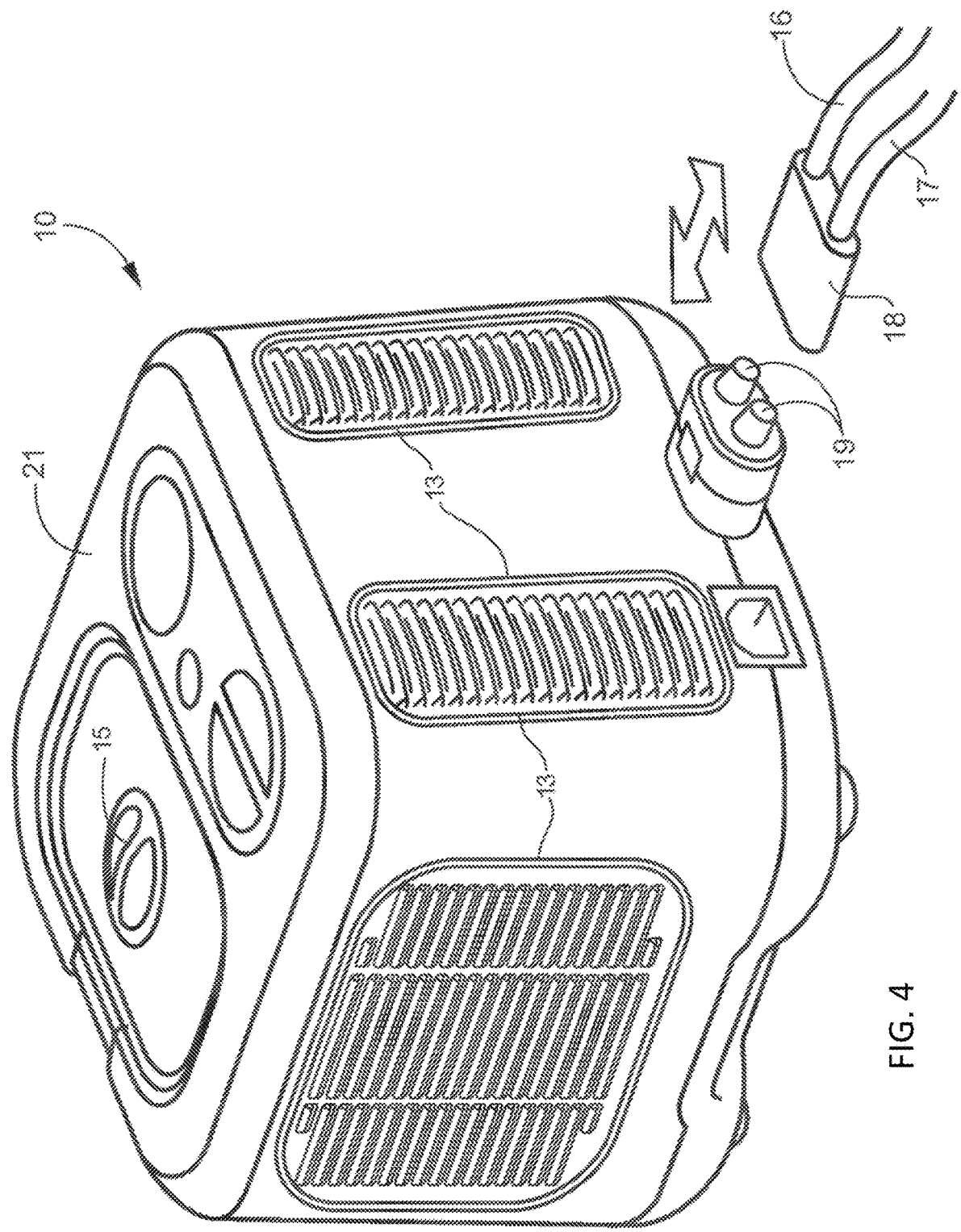
FIG. 4 is a perspective view of the exemplary control unit demonstrating the quick connection/disconnection of the flexible fluid supply and return lines.

In a preferred embodiment, the stress reduction and sleep promotion system 700 includes a mattress pad 11 to change the temperature of the sleep surface. FIG. 3 illustrates a thermoelectric control unit 10 according to the present invention. As shown, a pair of identical control units 10, 10' attach through flexible conduit to a temperature-conditioned article, such as mattress pad 11. The mattress pad 11 has two independent thermally regulated surface zones "A" and "B", each containing internal flexible (e.g., silicon) tubing 14 designed for circulating heated or cooled fluid within a hydraulic circuit between the control unit 10 and the mattress pad 11. As best shown in FIGS. 3 and 4, the flexible conduit assembly for each control unit 10 includes separate fluid supply and return lines 16, 17 connected to tubing 14, and a quick-release female connector 18 for ready attachment and detachment to external male connectors 19 of the control unit 10. Advantageously, the mattress pad 11 allows a user to retrofit an existing mattress.

In one embodiment, the thermoelectric control unit 10 is operatively connected (e.g., by flexible conduit) to a mattress, such that the temperature-conditioned surface is embedded in the mattress itself. In alternative exemplary embodiments, the thermoelectric control unit 10 is operatively connected (e.g., by flexible conduit) to any other temperature regulated article, such as a blanket or other bedding or covers, seat pad, sofa, chair, or the like.

Figure 5:
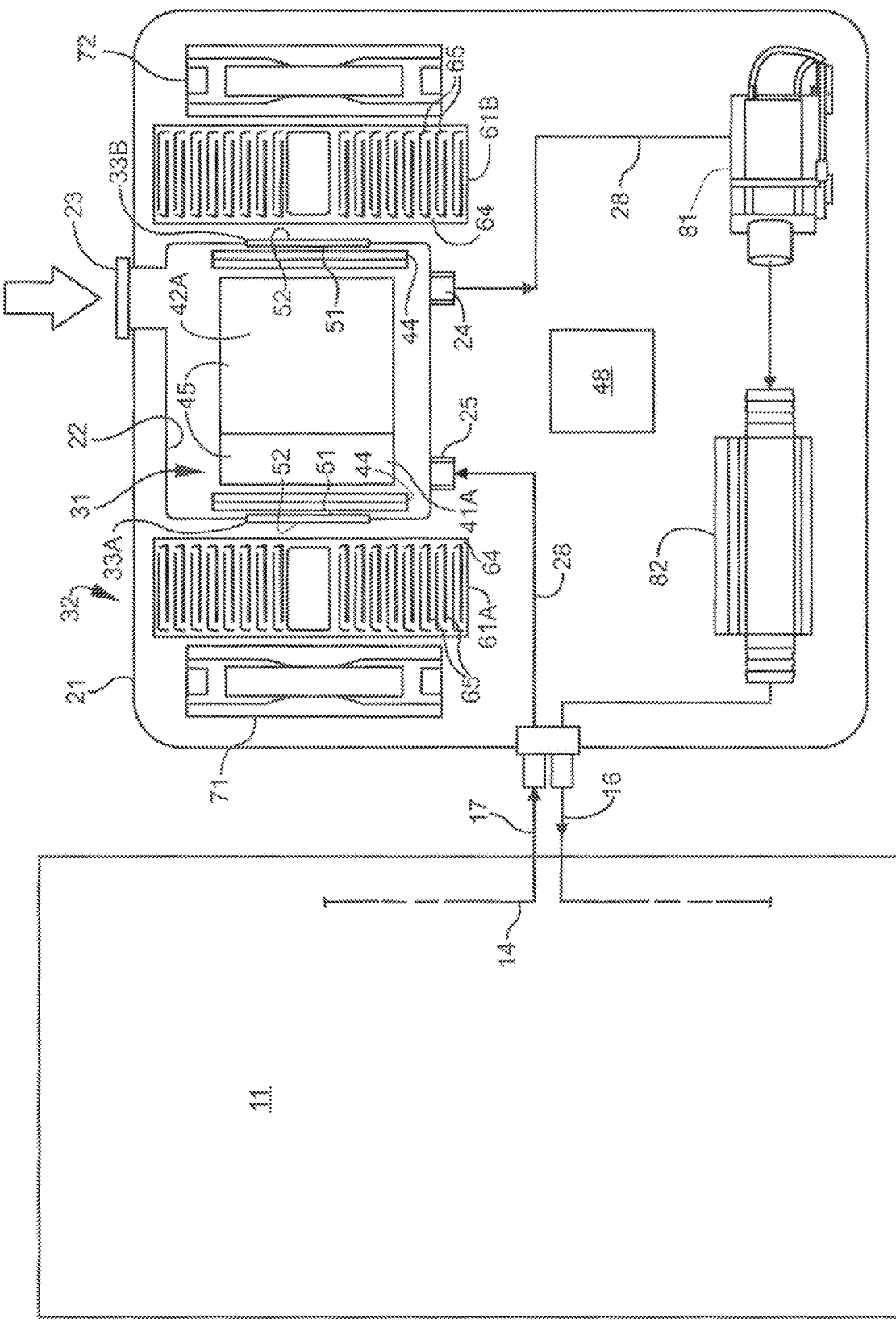
FIG. 5 is a side schematic view showing various internal components of the exemplary control unit fluidly connected to the mattress pad.
Figure 6:
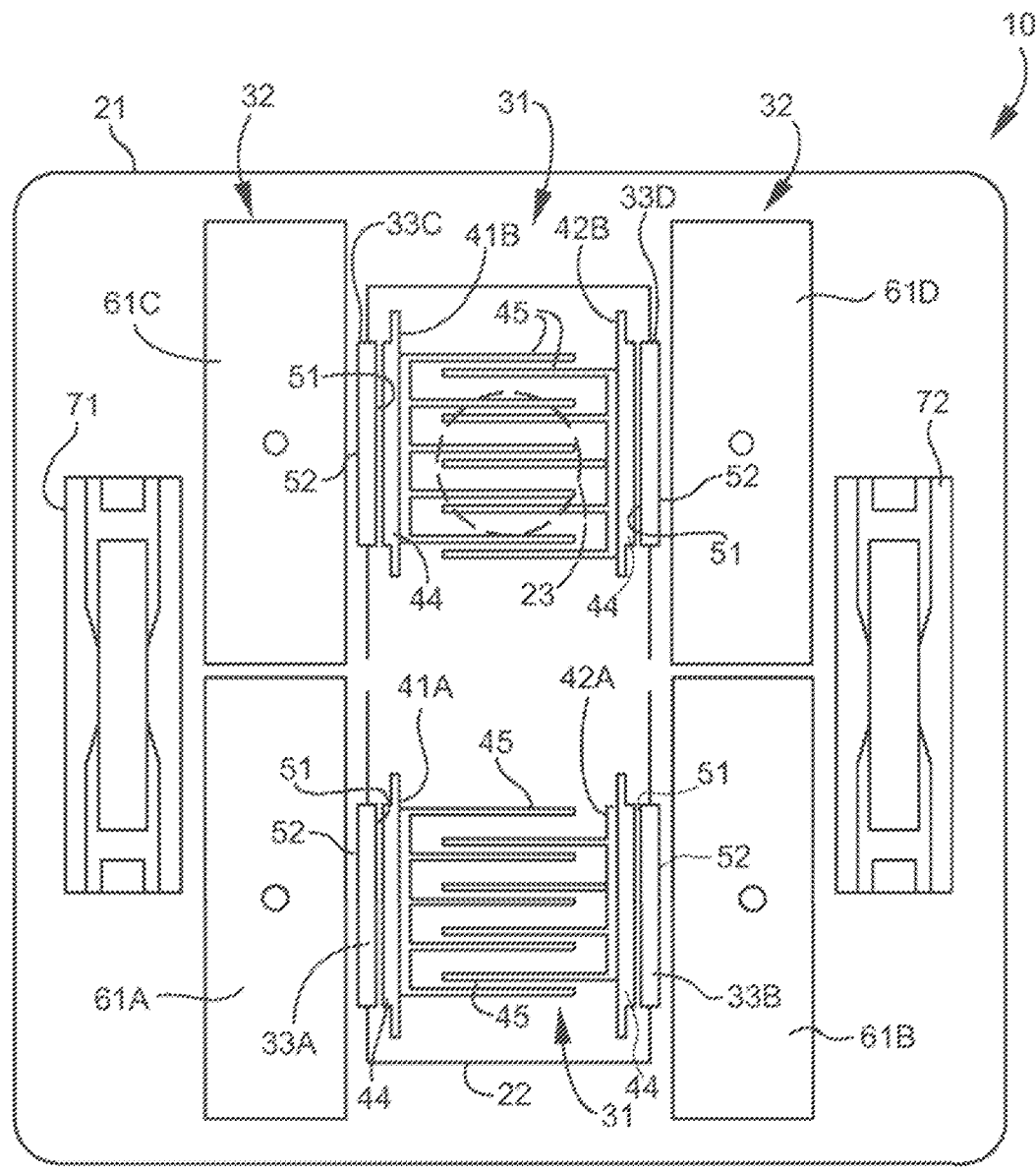
FIG. 6 is a top schematic view of the exemplary control unit.

As illustrated in FIGS. 5 and 6, the exemplary control unit 10 has an external housing 21, and a fluid reservoir 22 located inside the housing 21. The reservoir 22 has a fill opening 23 accessible through a removably capped opening 15 (FIG. 4) in housing 21, a fluid outlet 24, and a fluid return 25. Fluid contained in the reservoir 22 is moved in a circuit through a conduit assembly formed from in-housing tubes 28, the flexible supply and return lines 16, 17, and flexible silicone tubing 14 within the temperature-regulated pad 11. The fluid is selectively cooled, as described further below, by cooperating first and second heat exchangers 31, 32 and thermoelectric cooling modules 33A-33D. The cooling modules 33A-33D reside at an electrified junction between the first and second heat exchangers 31, 32, and function to regulate fluid temperature from a cool point of as low as 7.78° C. (46° F.), or cooler. The housing 21 and reservoir 22 may be either separately or integrally constructed of any suitable material, such as an anti-flammable ABS, polypropylene, or other molded polymer.

Referring to FIGS. 5 and 6, the first heat exchanger 31 is formed of pairs of oppositely directed internal heat sinks 41A, 42A and 41B, 42B communicating with an inside of the reservoir 22, and cooperating with thermoelectric cooling modules 33A-33D to cool the fluid inside the reservoir 22 to a selected (set) temperature. Each heat sink 41A, 42A, 41B, 42B has a substantially planar metal base 44 adjacent an exterior side wall of the reservoir 22, and a plurality of planar metal fins 45 extending substantially perpendicular to the base 44 and vertically inward towards a center region of the reservoir 22. In the exemplary embodiment, each pair of heat sinks 41A, 42A and 41B, 42B is formed from one 4-fin sink and one 5-fin sink arranged such that their respective fins 45 are facing and interleaved as shown in FIG. 6. The exemplary cooling modules 33A-33D are operatively connected to an internal power supply/main control board 48, and are formed from respective thin Peltier chips having opposing planar inside and outside major surfaces 51, 52. The inside major surface 51 of each cooling module 33A-33D resides in direct thermal contact with the planar base 44 of its corresponding heat sink 41A, 42A, 41B, 42B. A thermal pad or compound (not shown) may also reside between each cooling module 33A-33D and heat sink 41A, 42A, 41B, 42B to promote thermal conduction from base 44 outwardly across the fins 45.

The second heat exchanger 32 is formed from external heat sinks 61A-61D located outside of the fluid reservoir 22, and arranged in an opposite-facing direction to respective internal heat sinks 41A, 42A, 41B, 42B. Each external heat sink 61A-61D has a planar metal base 64 in direct thermal contact with the outside major surface 52 of an associated adjacent cooling module 33A-33D, and a plurality of planar metal fins 65 extending substantially perpendicular to the base 64 and horizontally outward away from the fluid reservoir 22. Heat generated by the cooling modules 33A-33D is conducted by the external heat sinks 61A-61D away from the modules 33A-33D and dissipated to a surrounding environment outside of the fluid reservoir 22. Electric case fans 71 and 72 may be operatively connected to the power supply/main control board 48 and mounted inside the housing 21 adjacent respective heat sinks 61A, 61B and 61C, 61D. The exemplary fans 71, 72 promote air flow across the sink fins 65, and outwardly from the control unit 10 through exhaust vents 13 formed with the sides and bottom of the housing 21. In one embodiment, each external heat sink 61A-61D has a substantially larger base 64 (as compared to the 4-fin and 5-fin internal sinks 41A, 42A, 41B, 42B) and a substantially greater number of fins 65 (e.g., 32 or more).

Both internal and external heat sinks may be active or passive, and may be constructed of any suitable conductive material, including aluminum, copper, and other metals. The heat sinks may have a thermal conductivity of 400 watts per meter-Kelvin (W/(m·K)), or more. The case fans 71, 72 may automatically activate and shut off as needed.

From the reservoir 22, the temperature conditioned fluid exits through the outlet 24 and enters the conduit assembly formed from an arrangement of in-housing Z-, L-, 7-, and S-shaped tubes 28 (and joints). A pump 81 is operatively connected to the reservoir 22 and functions to circulate the fluid through the control unit 10 in a circuit including the in-housing tubes 28 (and joints), flexible fluid supply line 16, silicone pad tubes 14, fluid return line 17, and back into the reservoir 22 through fluid return 25. As shown in FIG. 5, an insulated linear heat tube 82 is located outside of the fluid reservoir 22 and inside the housing 21, and communicates with the conduit assembly to selectively heat fluid moving from the control unit 10 to the mattress pad 11. The exemplary heat tube 82 may heat fluid moving in the hydraulic circuit to a desired temperature of as warm as 47.78° C. (118° F.).

The control unit has at least one fluid reservoir. In one embodiment, the control unit includes two fluid reservoirs. A first fluid reservoir is used to heat and/or cool fluid that circulates through the temperature-regulated pad. The first fluid reservoir includes at least one sensor to measure a level of the fluid. A second fluid reservoir is used to store fluid. In a preferred embodiment, fluid from the second fluid reservoir is automatically used to fill the first fluid reservoir when the at least one sensor indicates that the level of the fluid is below a minimum value. Advantageously, this optimizes the temperature in the first fluid reservoir because only a small amount of stored fluid is introduced into the first fluid reservoir when needed. Additionally, this embodiment reduces the refilling required for the control unit, saving the user time and effort. In one embodiment, the at least one fluid reservoir is formed of metal. In another embodiment, the metal of the at least one fluid reservoir is electrically connected to ground.

Figure 7:
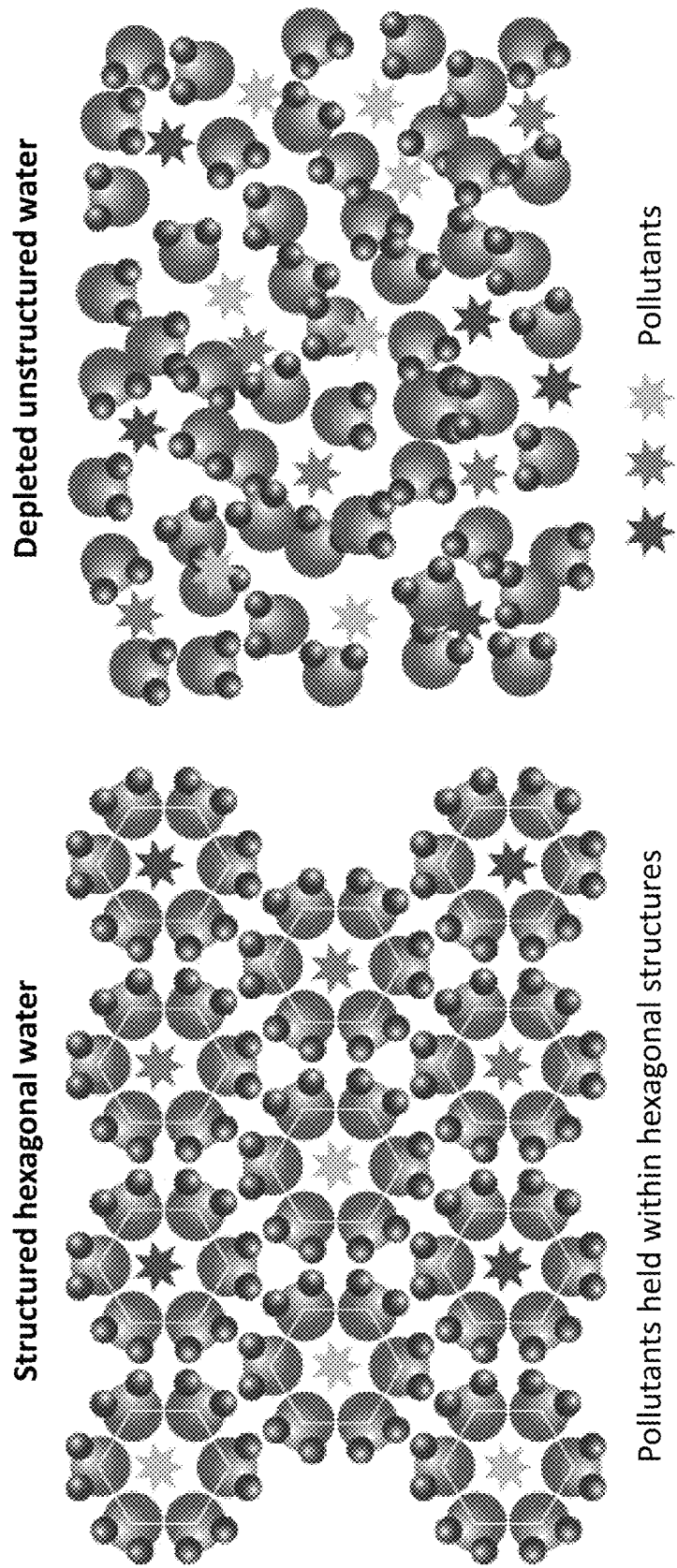
FIG. 7 illustrates the difference between structured water and unstructured water.

In a preferred embodiment, the control unit includes at least one mechanism for forming structured water. FIG. 7 illustrates the difference between structured water and unstructured water. In one embodiment, the control unit includes at least one vortex to treat the fluid. The at least one vortex reduces bacteria, algae, and fungus in the fluid without using additional chemicals. In one embodiment, the at least one vortex includes at least one left spin vortex and at least one right spin vortex. The at least one left spin vortex and the at least one right spin vortex mimics the movement of water in nature. One example of utilizing vortex technologies to treat fluids is described in U.S. Pat. No. 7,238,289, which is incorporated herein by reference in its entirety. Alternatively, the fluid flows or tumbles over or through a series of balls and/or rocks. In one embodiment, the rocks are in a hexagonal shape. A tumbling action or vortex aligns the molecules in the structured water to retain energy (i.e., cooling or heating) for a longer period of time. Surprisingly, the aligned or structured water molecules produce a 20% increase in the heating and cooling capacity of the water.

In a preferred embodiment, the fluid is water. In one embodiment, the water is treated with an ultraviolet (UV) purification system to kill microorganisms (e.g., bacteria, viruses, molds). The UV purification system includes at least one UV light bulb to expose microorganisms to UV radiation, which prevents the microorganisms from reproducing. This reduces the number of microorganisms in the water without using additional chemicals. In one embodiment, the at least one UV light bulb is a UV-C light emitting diode (LED). In another embodiment, the at least one UV light bulb is a mercury vapor bulb.

Additionally or alternatively, the water is treated with at least one filter to remove contaminants and/or particles. In a preferred embodiment, the at least one filter clarifies the water before exposure to the at least one UV light bulb. Contaminants and/or particles in the water are larger than the microorganisms, so contaminants and/or particles block the UV rays from reaching the microorganisms. In one embodiment, the at least one filter is a sediment filter, an activated carbon filter, a reverse osmosis filter, and/or a ceramic filter. In another embodiment, one or more of the at least one filter includes copper and/or silver (e.g., nanoparticles, ions, colloidal) to suppress the growth of microorganisms. Contaminants and/or particles that are removed from the water include sediment, rust, calcium carbonate, organic compounds, chlorine, and/or minerals.

The at least one filter preferably removes contaminants and/or particles with a diameter greater than 0.3 µm. Alternatively, the at least one filter removes contaminants and/or particles with a diameter greater than 0.5 µm. In another embodiment, the at least one filter removes contaminants and/or particles with a diameter greater than 0.05 µm. In another embodiment, the at least one filter removes contaminants and/or particles with a diameter greater than 1 nm.

In one embodiment, the water is treated with copper and/or silver ions. The copper and/or silver ions are positively charged and bond with negative sites on cell walls of microorganisms. This can lead to the deactivation of proteins and ultimately to cell death. Copper and/or silver ions can also destroy biofilms and slimes. In one embodiment, the copper and/or silver ions are created through electrolysis.

Alternatively, the water is treated with at least one chemical to inhibit growth of bacteria and microorganisms or to remove lime and calcium buildup. In one embodiment, the water is treated with a compound containing iodine or chlorine. In another embodiment, the water is treated with salt and/or a peroxide solution. In yet another embodiment, the water is treated with citric acid.

The thermoelectric control unit may further include other features and electronics not shown. In one embodiment, the control unit includes a touch control and display board, overheat protectors, fluid level sensor, thermostat, additional case fans, and/or at least one speaker. The control unit may also include an external power cord designed to plug into standard household electrical outlets, or may be powered using rechargeable or non-rechargeable batteries. In one embodiment, the touch control and display board includes a power button, temperature selection buttons (e.g., up arrow and down arrow), and/or an LCD to display the temperature. In another embodiment, the touch control and display board includes a program selection menu.

The control unit preferably has at least one processor. By way of example, and not limitation, the processor may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information. In one embodiment, one or more of the at least one processor is operable to run predefined programs stored in at least one memory of the control unit.

The control unit preferably includes at least one antenna, which allows the control unit to receive and process input data (e.g., temperature settings, start and stop commands) from at least one remote device (e.g., smartphone, tablet, laptop computer, desktop computer, remote control). In a preferred embodiment, the at least one remote device is in wireless network communication with the control unit. The wireless communication is, by way of example and not limitation, radiofrequency, Bluetooth®, ZigBee®, Wi-Fi®, wireless local area networking, near field communication (NFC), or other similar commercially utilized standards. Alternatively, the at least one remote device is in wired communication with the control unit through USB or equivalent.

In a preferred embodiment, the at least one remote device is operable to set target temperatures for the mattress pad. The at least one remote device preferably has a user interface (e.g., a mobile application for a smartphone or tablet, buttons on a remote control) that allows a user to select target temperatures for the mattress pad or independent zones within the mattress pad. In one embodiment, the mattress pad includes temperature probes in each zone that provide temperature data for that zone to the at least one processor, which compares a target temperature set using the at least one device to an actual measured temperature to determine whether to heat or cool the fluid and determine where to distribute the heated or cooled fluid in order to make the actual temperature match the target temperature.

Those skilled in the art will recognize that programmatic control of the target temperatures over time, such as over the course of a night's sleep, is possible using the at least one remote device. Because the target temperatures can be set at any time, those target temperatures can be manipulated through the sleeping period in order to match user preferences or a program to correlate with user sleep cycles to produce a deeper, more restful sleep.

Figure 8A:
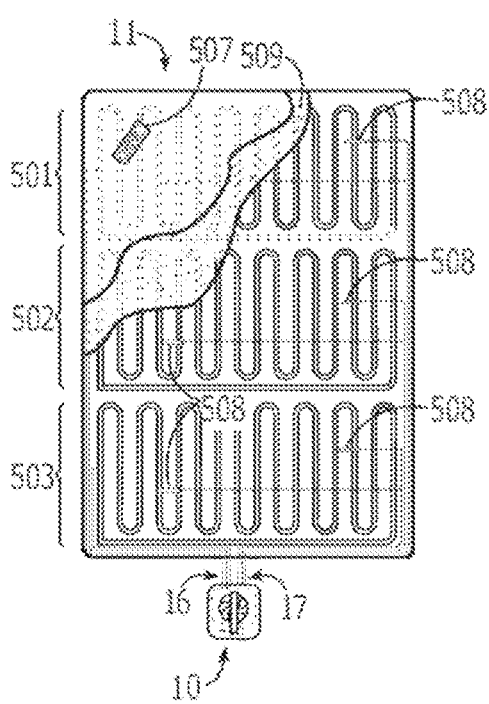
FIG. 8A illustrates one embodiment of a mattress pad with three independent temperature zones.

FIG. 8A illustrates one embodiment of a mattress pad with three independent temperature zones. The three independent temperature zones 501, 502, 503 generally correspond to the head, body and legs, and feet, respectfully, of a user. Although only three zones are shown, it is equally possible to have one, two, four, or more independent temperature zones. A wireless remote control 507 is used to set the target temperatures for each of the zones 501, 502, 503. Fluid is delivered to the mattress pad 11 from the control unit 10 via a fluid supply line 16 that enters the continuous perimeter via an opening sized to sealingly receive the fluid supply line 16. Fluid is removed from the mattress pad 11 and returned to the control unit 10 via a fluid return line 17 that exits the continuous perimeter via an opening sized to sealingly receive the fluid return line 17.

Temperature probes 508 in each zone provide actual measured temperature data for that zone to the control unit 10. The control unit 10 compares the target temperature set using the wireless remote control 507 and the actual measured temperature to determine whether to heat or cool the fluid and determine to which conduit or circuits the heated or cooled fluid should be distributed in order to make the actual temperature match the target temperature.

In one embodiment, a larger number of temperature probes are in the independent temperature zones corresponding to the core body region, and a smaller number of temperature probes are in the independent temperature zones not corresponding to the core body region. In one example, zone 501 contains three temperature probes, zone 502 contains five temperature probes, and zone 503 contains three temperature probes. This embodiment provides the advantage of more closely monitoring the temperature of the pad in the core body region, which is important because core body temperature impacts how well a user sleeps.

In another embodiment, an independent temperature zone contains three temperature probes. In one example, zone 501 contains a temperature probe in the center of the mattress pad 11, a temperature probe on the left side of the mattress pad 11, and a temperature probe on the right side of the mattress pad 11. Advantageously, this embodiment provides information about the left, center, and right of the mattress pad. In yet another embodiment, an independent temperature zone contains at least three temperature probes.

The mattress pad includes padding 509 between the conduit circuits and the resting surface, in order to improve the comfort of a user and to prevent the concentrated heat or cold of the conduit circuits from being applied directly or semi-directly to the user's body. Instead, the conduit circuits heat or cool the padding 509, which provides more gentle temperature modulation for the user's body.

Figure 8B:
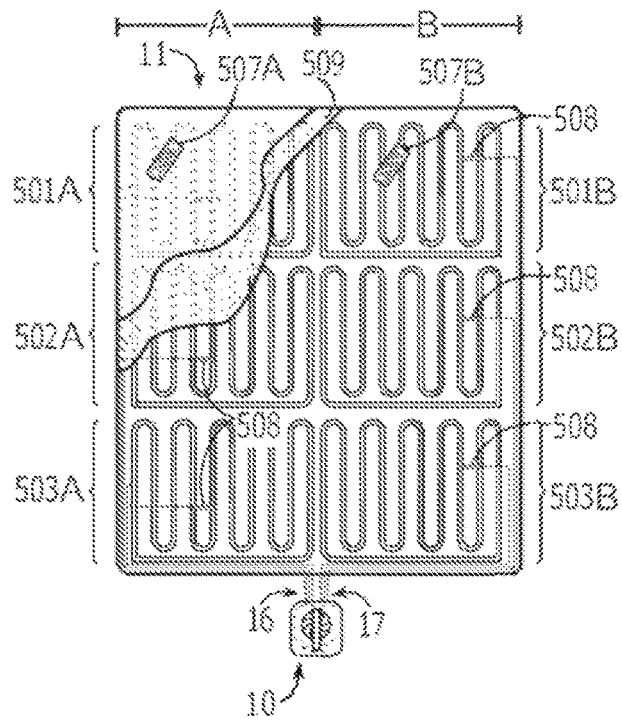
FIG. 8B illustrates one embodiment of a double mattress pad with three independent temperature zones for both users.

FIG. 8B illustrates one embodiment of a double mattress pad. Three independent temperature zones 501A, 502A, 503A generally correspond to the head, body and legs, and feet, respectfully, of a first user who utilizes surface zone "A". Three independent temperature zones 501B, 502B, 503B generally correspond to the head, body and legs, and feet, respectfully, of a second user who utilizes surface zone "B". Although only three zones are shown for each user, it is equally possible to have one, two, four, or more independent temperature zones. A first wireless remote control 507A is used to set the target temperatures for each of the zones 501A, 502A, 503A. A second wireless remote control 507B is used to set the target temperatures for each of the zones 501B, 502B, 503B. Temperature probes 508 in each zone provide actual measured temperature data for that zone to the control unit 10. The control unit 10 compares the target temperature set using the wireless remote control 507A, 507B and the actual measured temperature to determine whether to heat or cool the fluid and determine to which conduit or circuits the heated or cooled fluid should be distributed in order to make the actual temperature match the target temperature.

In this embodiment, despite the presence of two separate controls, a single control unit 10 is utilized to control the temperature of the fluid. In another embodiment, a first control unit is utilized to control the temperature of the fluid for the first user and a second control unit is utilized to control the temperature of the fluid for the second user. Alternatively, each user has at least two control units to control the temperature of the fluid.

Figure 8C:
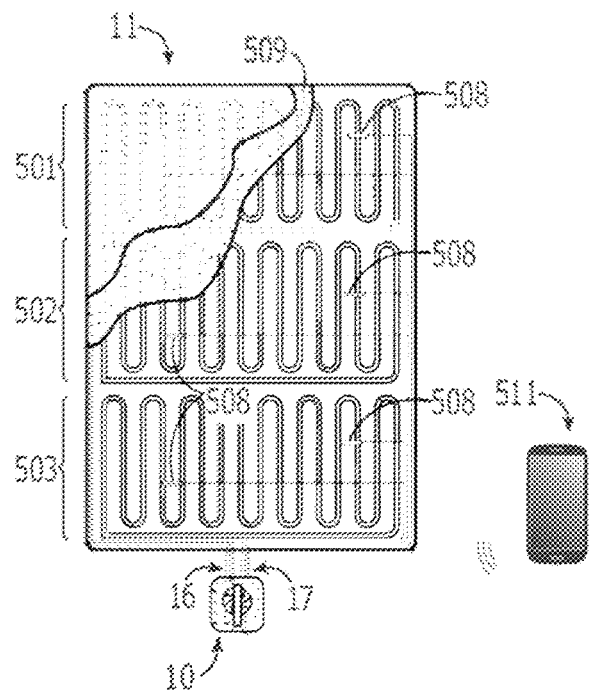
FIG. 8C illustrates one embodiment of a mattress pad with three independent temperature zones connected to at least one remote device.

FIG. 8C illustrates one embodiment of a mattress pad with three independent temperature zones connected to at least one remote device 511. In a preferred embodiment, the at least one remote device is a smartphone or a tablet. The at least one remote device preferably has a mobile application that allows for the control unit 10 to vary the temperature of the mattress pad 11 according to a schedule of target temperatures selected to correlate with sleep cycles of the user. Such an arrangement promotes deeper, more restful sleep by altering body temperature at critical points.

Preferably, the mattress pad is sized to fit standard mattress sizes. For example, twin (about 97 cm by about 191 cm (about 38 inches by about 75 inches)), twin XL (about 97 cm by about 203 cm (about 38 inches by about 80 inches)), full (about 137 cm by about 191 cm (about 54 inches by about 75 inches)), queen (about 152 cm by about 203 cm (about 60 inches by about 80 inches)), king (about 193 cm by about 203 cm (about 76 inches by about 80 inches), and California king (about 183 cm by about 213 cm (about 72 inches by about 84 inches)). In one embodiment, the mattress pad is about 76 cm by about 203 cm (about 30 inches by about 80 inches). This allows a single user of a full, queen, or king size bed to use the mattress pad without affecting a sleeping partner. In one embodiment, the mattress pad is sized to fit a crib mattress (about 71 cm by about 132 cm (about 28 inches by about 52 inches)). In a preferred embodiment, the single mattress pad (e.g., twin, twin XL, sized to fit a single user of a larger bed, crib) attaches to one control unit and the double mattress pad (e.g., full, queen, king, California king) attaches to two control units.

In an alternative embodiment, the mattress pad contains a conductive fiber to heat one section of the mattress pad and water circulation to cool another section of the mattress pad. In one example, this allows the temperature of the main body or body core region to be lower than the temperature for the feet. The feet play an active role in the regulation of body temperature. The feet have a large surface area and specialized blood vessels, which allow the feet to release heat from the body. If the feet become too cold, excess heat cannot be released from the body and an individual will not be able to sleep.

In one embodiment, the mattress pad is grounded, which provides the human body with electrically conductive contact with the surface of the earth. Grounding is based on the theory that the earth is a source of negatively charged free electrons, and, when in contact with the earth, the body can use these free electrons as antioxidants to neutralize free radicals within the body. Grounding the body during sleep can normalize cortisol levels, improve sleep, and decrease pain and stress levels. In a preferred embodiment, the mattress pad has a conductive material on at least one exterior surface of the mattress pad. In one embodiment, the mattress pad is attached to a wire that is electrically connected to an electrical outlet ground port. Alternatively, the mattress pad is attached to a wire that is connected to a ground rod.

The mattress pad includes at least two layers of a waterproof material that are laminated, affixed to each other, adhered to each other, attached to each other, secured to each other, or welded together to prevent separation or delamination of the layers. In a preferred embodiment, the waterproof material is a urethane or a mixture of urethane and ethylene-vinyl acetate (EVA). A first layer of the waterproof material is permanently affixed to a second layer of the waterproof material. The first layer of the waterproof material has an exterior surface and an interior surface. The second layer of the waterproof material has an exterior surface and an interior surface. In a preferred embodiment, the first layer of the waterproof material is welded (e.g., using high frequency/radio frequency (RF) welding or heat welding) to the second layer of the waterproof material along a continuous perimeter, creating at least one interior chamber constructed and configured to retain fluid without leaking between the interior surface of the first layer of the waterproof material and the interior surface of the second layer of the waterproof material. Fluid is delivered to the at least one interior chamber via a fluid supply line that enters the continuous perimeter via an opening sized to sealingly receive the fluid supply line. Fluid is removed from the at least one interior chamber via a fluid return line that exits the continuous perimeter via an opening sized to sealingly receive the fluid return line.

In a preferred embodiment, the waterproof material is covered on the exterior surfaces with an interlock or knit fabric. The interlock or knit fabric on the exterior surface of the mattress pad preferably contains a copper or a silver ion thread for antimicrobial protection. Alternatively, the interlock or knit fabric on the exterior surface of the mattress pad is treated with an antibacterial or an antimicrobial agent (e.g., Microban®). In one embodiment, the waterproof material is covered on the exterior surface with a moisture wicking material.

In one embodiment, the mattress pad includes a spacer layer positioned within the interior chamber between the interior surface of the first layer of the waterproof material and the interior surface of the second layer of the waterproof material. The spacer layer provides separation between the first layer of the waterproof material and the second layer of the waterproof material, ensuring that the fluid flows through the mattress pad when a body is on the mattress pad. The spacer layer advantageously provides structural support to maintain partial channels through the interior chamber or fluid passageways, which are important to ensure constant and consistent fluid flow through the interior chamber with heavy users on firm mattresses. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties.

Figure 9A:
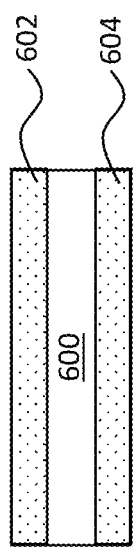
FIG. 9A illustrates a cross-section of a mattress pad with two layers of waterproof material.

FIG. 9A illustrates a cross-section of a mattress pad with two layers of waterproof material. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding).

Figure 9B:
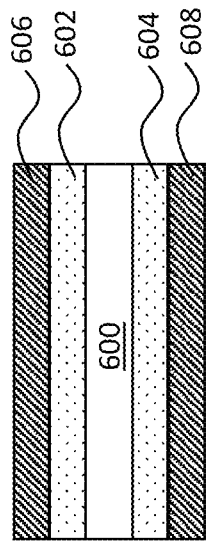
FIG. 9B illustrates a cross-section of a mattress pad with two layers of waterproof material and two layers of a second material.

FIG. 9B illustrates a cross-section of a mattress pad with two layers of waterproof material and two layers of a second material. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding). A first layer of a second material 606 is on an exterior surface of the first layer of the waterproof material 602. A second layer of the second material 608 is on an exterior surface of the second layer of the waterproof material 604. In a preferred embodiment, the second material is a knit or interlock material. Alternatively, the second material is a woven or non-woven material. In yet another embodiment, the second material is formed of plastic.

Figure 9C:
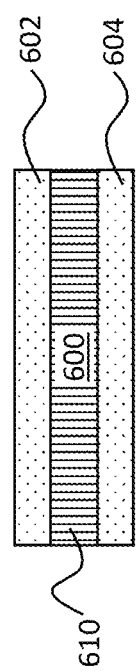
FIG. 9C illustrates a cross-section of a mattress pad with two layers of waterproof material and a spacer layer.

FIG. 9C illustrates a cross-section of a mattress pad with two layers of waterproof material and a spacer layer. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding).

A spacer layer 610 is positioned within the interior chamber 600 between an interior surface of the first layer of the waterproof material 602 and an interior facing of the second layer of the waterproof material 604. The spacer layer 610 is configured to provide structural support to maintain partial channels for fluid flow through the interior chamber. In one embodiment, the fluid flows through the spacer layer. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties. In another embodiment, the spacer layer 610 is in a honeycomb shape.

Figure 9D:
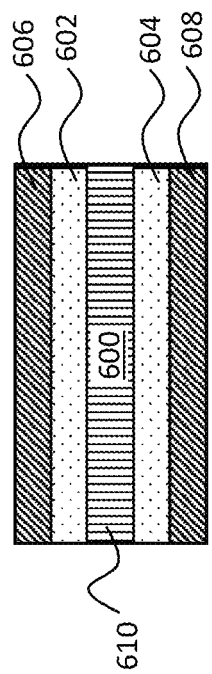
FIG. 9D illustrates a cross-section of a mattress pad with two layers of waterproof material, two layers of a second material, and a spacer layer.

FIG. 9D illustrates a cross-section of a mattress pad with two layers of waterproof material, two layers of a second material, and a spacer layer. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding). A first layer of a second material 606 is on an exterior surface of the first layer of the waterproof material 602. A second layer of the second material 608 is on an exterior surface of the second layer of the waterproof material 604. In a preferred embodiment, the second material is a knit or interlock material. Alternatively, the second material is a woven or non-woven material. In yet another embodiment, the second material is formed of plastic.

A spacer layer 610 is positioned within the interior chamber 600 between an interior surface of the first layer of the waterproof material 602 and an interior facing of the second layer of the waterproof material 604. The spacer layer 610 is configured to provide structural support to maintain partial channels for fluid flow through the interior chamber. In one embodiment, the fluid flows through the spacer layer. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties.

Figure 10:
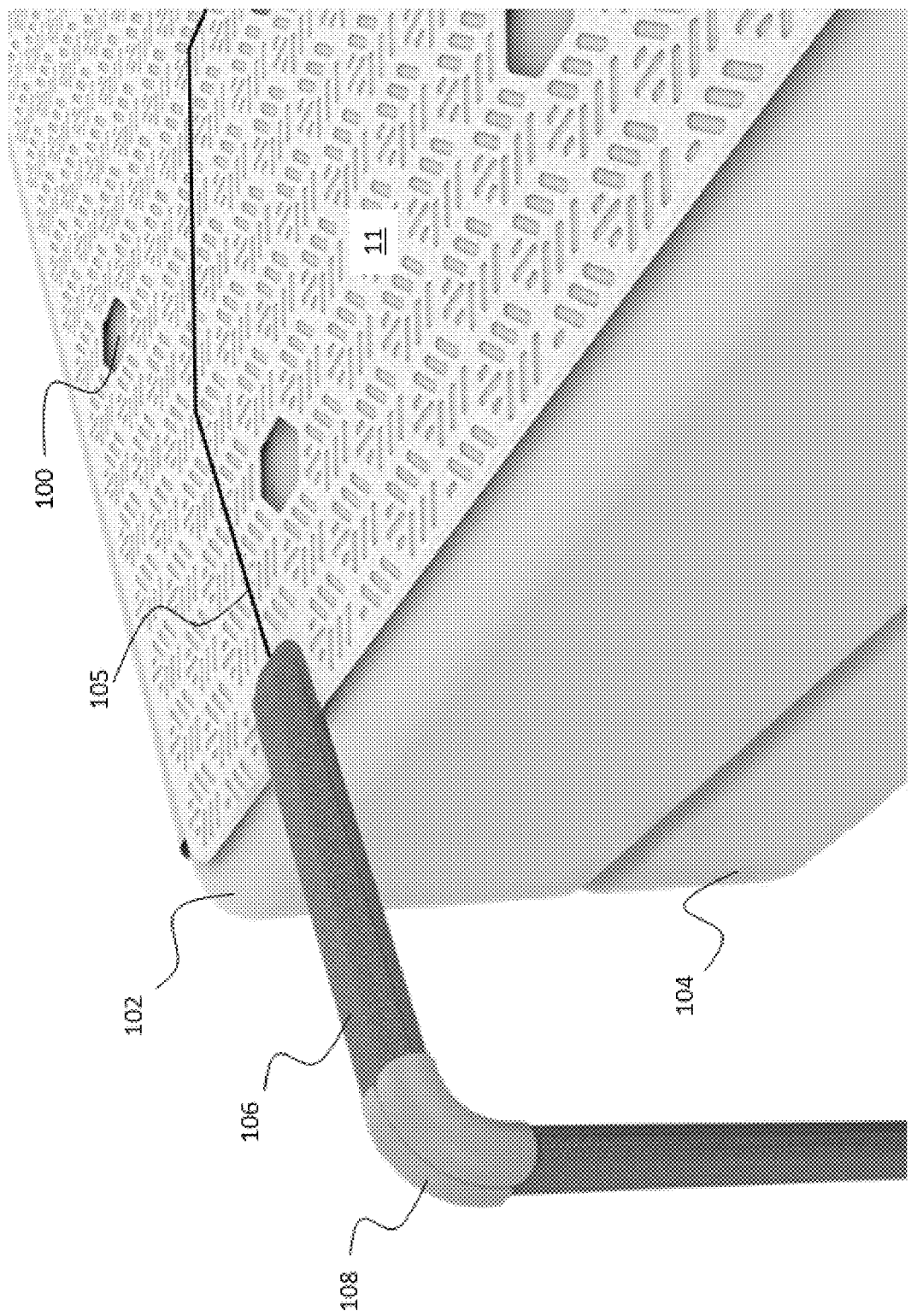
FIG. 10 is a view of a mattress pad hose elbow according to one embodiment.

FIG. 10 is a view of a mattress pad hose elbow according to a preferred embodiment. The mattress pad 11 is placed on top of a mattress 102 and box springs or foundation 104. The mattress pad 11 connects to the control unit (not shown) via a flexible hose 106 containing the flexible supply and return lines. The flexible hose is preferably formed from a polyurethane. Alternatively, the flexible hose is formed from extruded silicone double wall tubing. In one embodiment, the flexible hose has a polyethylene foam or other insulating cover. Additionally or alternatively, the flexible hose is covered with a fabric (e.g., nylon, polyester, rayon).

A mattress pad hose elbow 108 is concentric around the flexible hose 106. The mattress pad hose elbow 108 secures the flexible hose 106 to the side of the mattress 102 and box springs or foundation 104, which provides structural support to the flexible hose 106. The mattress pad hose elbow 108 is sized to fit tightly around the flexible hose 106. In a preferred embodiment, the mattress pad hose elbow 108 is formed with silicone or rubber. Alternatively, the mattress pad hose elbow 108 is formed from plastic (e.g., ethylene-vinyl acetate (EVA) foam, polyethylene foam). In a preferred embodiment, the mattress pad hose elbow 108 is operable to slide on the flexible hose 106. In one embodiment, the mattress pad hose elbow 108 is adjustable.

The mattress pad 11 preferably contains a plurality of holes or openings 100 in the surface of the mattress pad 11. The plurality of holes or openings 100 direct the movement of the fluid in the pad. In a preferred embodiment, the plurality of holes or openings 100 is in a preselected pattern to help manufacturing efficiency. Alternatively, the plurality of holes or openings 100 is in a random pattern. The plurality of holes or openings 100 is shown in a hexagon shape in FIG. 10. Alternatively, the shape of each of the plurality of holes or openings 100 can be in the shape of a triangle, a circle, a rectangle, a square, an oval, a diamond, a pentagon, a heptagon, an octagon, a nonagon, a decagon, a trapezium, a parallelogram, a rhombus, a cross, a semicircle, a crescent, a heart, a star, a snowflake, or any other polygon. In one embodiment, the voids created by the plurality of holes or openings 100 include at least 80% of the surface area of the mattress pad. In other embodiments, the voids created by the plurality of holes or openings 100 include at least 5%, at least 10%, at least 15%, at least 20%, at least 25%, at least 30%, at least 40%, at least 50%, at least 60%, at least 70%, at least 75%, at least 85%, at least 90%, or at least 95% of the surface area of the mattress pad.

The spacing and number of the plurality of holes or openings 100 can be varied to adjust the thermal properties of the mattress pad. For example, in one embodiment, the density of the holes or openings is higher near the torso region than in the head and leg regions, for providing more exposure to the torso region of the user for managing body temperature in that region, and less exposure to the extremities of the user. In one embodiment, the spacing between each of the plurality of holes or openings is at least 5 mm (0.2 inches).

In a preferred embodiment, the mattress pad 11 contains at least one weld line 105 to help manage the flow of the fluid in the interior chamber. The at least one weld line 105 preferably directs the fluid flow through the pad from head to foot, and returns the fluid to the control unit via the return line. The at least one weld line 105 allows the fluid to flow across all areas of the mattress pad 11 to provide a substantially uniform temperature within the pad. In one embodiment, the at least one weld line is formed from the permanent attachment of the first layer of the waterproof material and the second layer of the waterproof layer along the periphery of the plurality of holes or openings.

Figure 11:
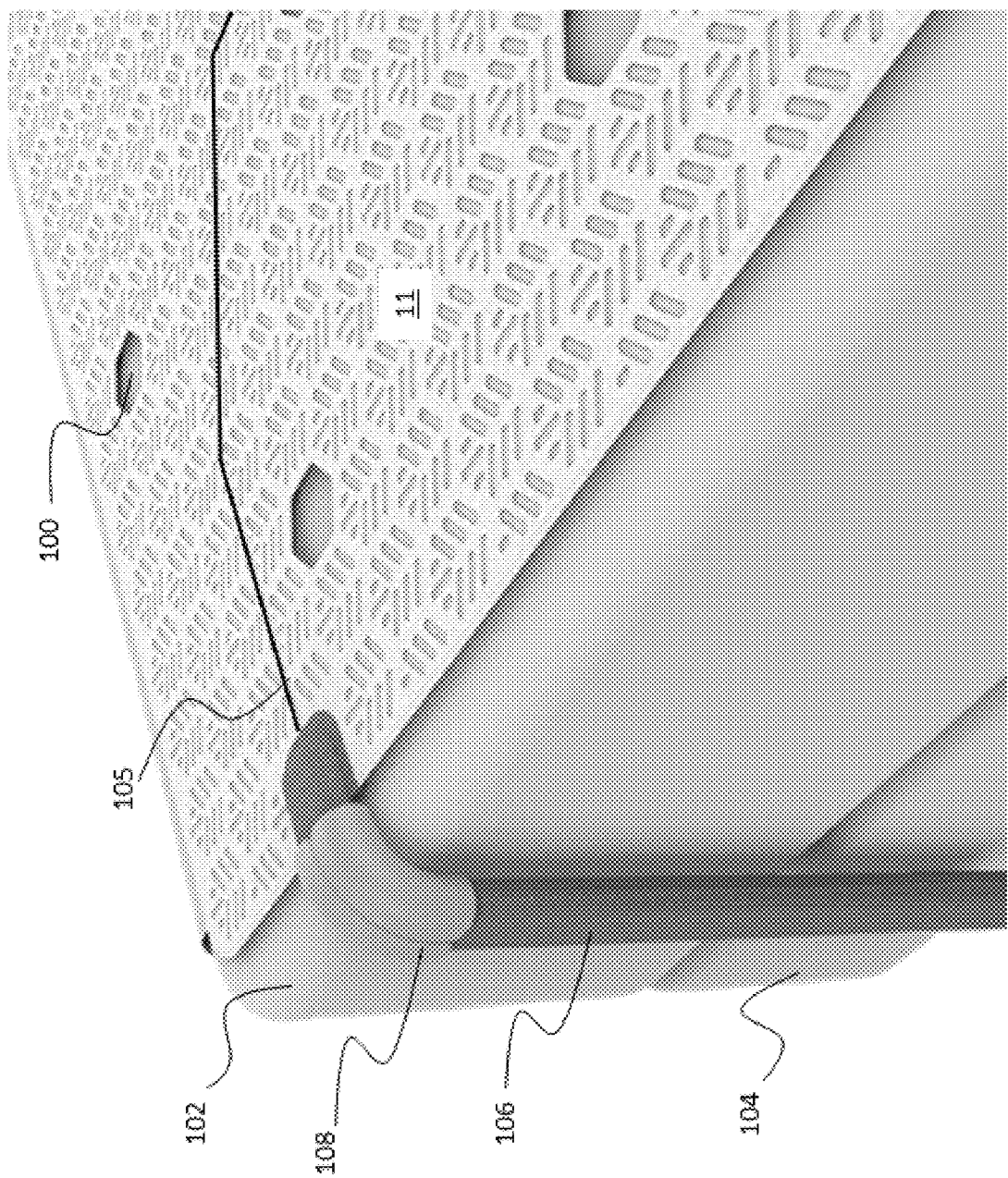
FIG. 11 is another view of the mattress pad hose elbow of FIG. 10.

FIG. 11 is another view of the mattress pad hose elbow of FIG. 10. The flexible hose 106 is positioned next to the mattress 102 and the box springs or foundation 104 using the mattress pad hose elbow 108. Advantageously, the mattress pad hose elbow 108 secures the flexible hose 106 to the side of the mattress 102 and box springs or foundation 104, providing structural support for the flexible hose 106. Further, the total height of a mattress, box springs or foundation, and/or a bed frame is not uniform. The mattress pad hose elbow 108 provides customization for the height of the mattress, the box springs or foundation, and/or the bed frame.

In another embodiment, the flexible hose is positioned next to the mattress using hook and loop tape. In yet another embodiment, the flexible hose is positioned next to the mattress using elastic. In still another embodiment, the flexible hose is positioned next to the mattress using at least one snap. Alternatively, the flexible hose is positioned next to the mattress using at least one buckle.

Figure 12:
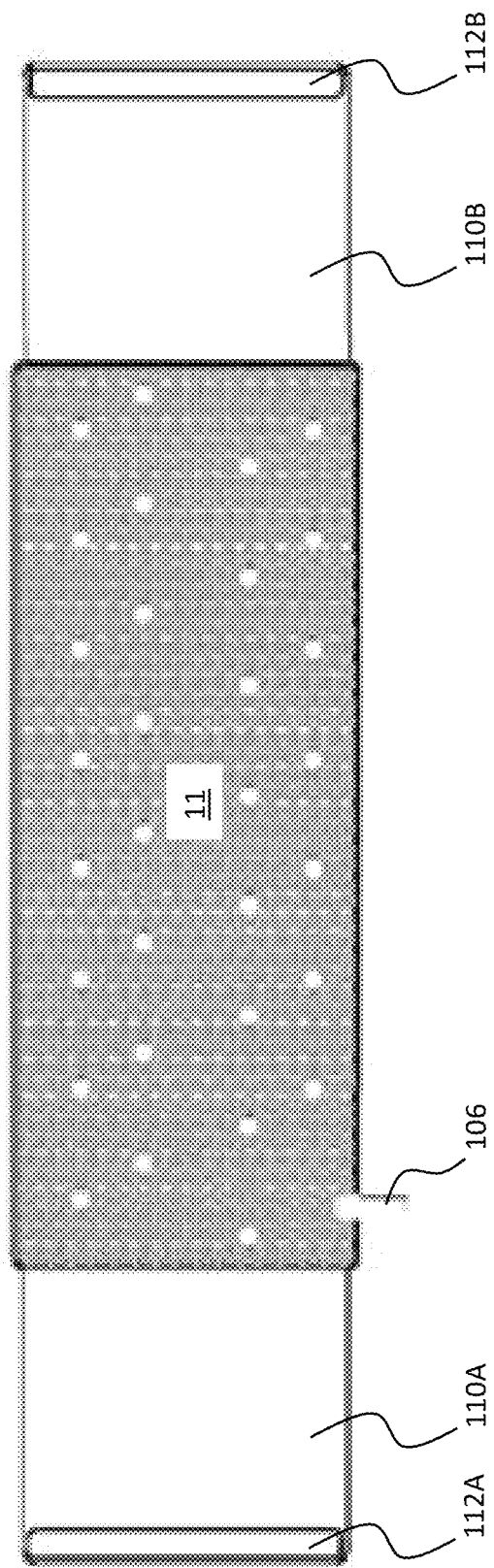
FIG. 12 is an exploded view of a single mattress pad.

FIG. 12 is a top perspective view of a single mattress pad. A top panel 110A is attached (e.g., sewn, adhered, welded) to the top of the mattress pad 11 at an attachment point 114A. A bottom panel 110B is attached (e.g., sewn, adhered, welded) to the bottom of the mattress pad 11 at an attachment point 114B. A non-slip piece 112A is attached (e.g., sewn, adhered, welded) to the top panel 110A on a side opposite the attachment point 114A. A non-slip piece 112B is attached (e.g., sewn, adhered, welded) to the bottom panel 110B on a side opposite the attachment point 114B. Preferably, the top panel 110A and the bottom panel 110B are formed from the same material as the second material (e.g., a knit or interlock fabric) on the exterior surface of the mattress pad. In a preferred embodiment, the non-slip pieces 112A, 112B are formed from foam. Alternatively, the non-slip pieces 112A, 112B are formed from latex, silicon, or rubber. The non-slip pieces 112A, 112B are preferably moisture wicking and/or antimicrobial. In one embodiment, the non-slip pieces 112A, 112B are printed onto the top panel 110A and the bottom panel 110B. In one embodiment, the top panel 110A and the bottom panel 110B are between about 18 cm (about 7 inches) and about 76 cm (about 30 inches) in length. In a preferred embodiment, top panel 110A and the bottom panel 110B are about 66 cm (about 26 inches) in length.

In another embodiment, the top panel 110A and the bottom panel 110B act as a non-slip surface. In one embodiment, the top panel 110A and the bottom panel 110B are made of gripper or anti-slip fabric. In this embodiment, the non-slip pieces 112A and 112B are not needed because the top panel 110A and the bottom panel 110B act as the non-slip surface.

The single mattress pad is preferably reversible, such that the mattress pad is operable when either exposed surface is facing upward. Advantageously, this allows the flexible hose to exit on either the left or the right side of the bed. This reversibility eliminates the need to manufacture single mattress pads with a "left" configuration or a "right" configuration for single users of a full, queen, or king size bed and/or single users where a bed is positioned such that a particular configuration is required (e.g., a bed positioned against a wall).

Figure 13:
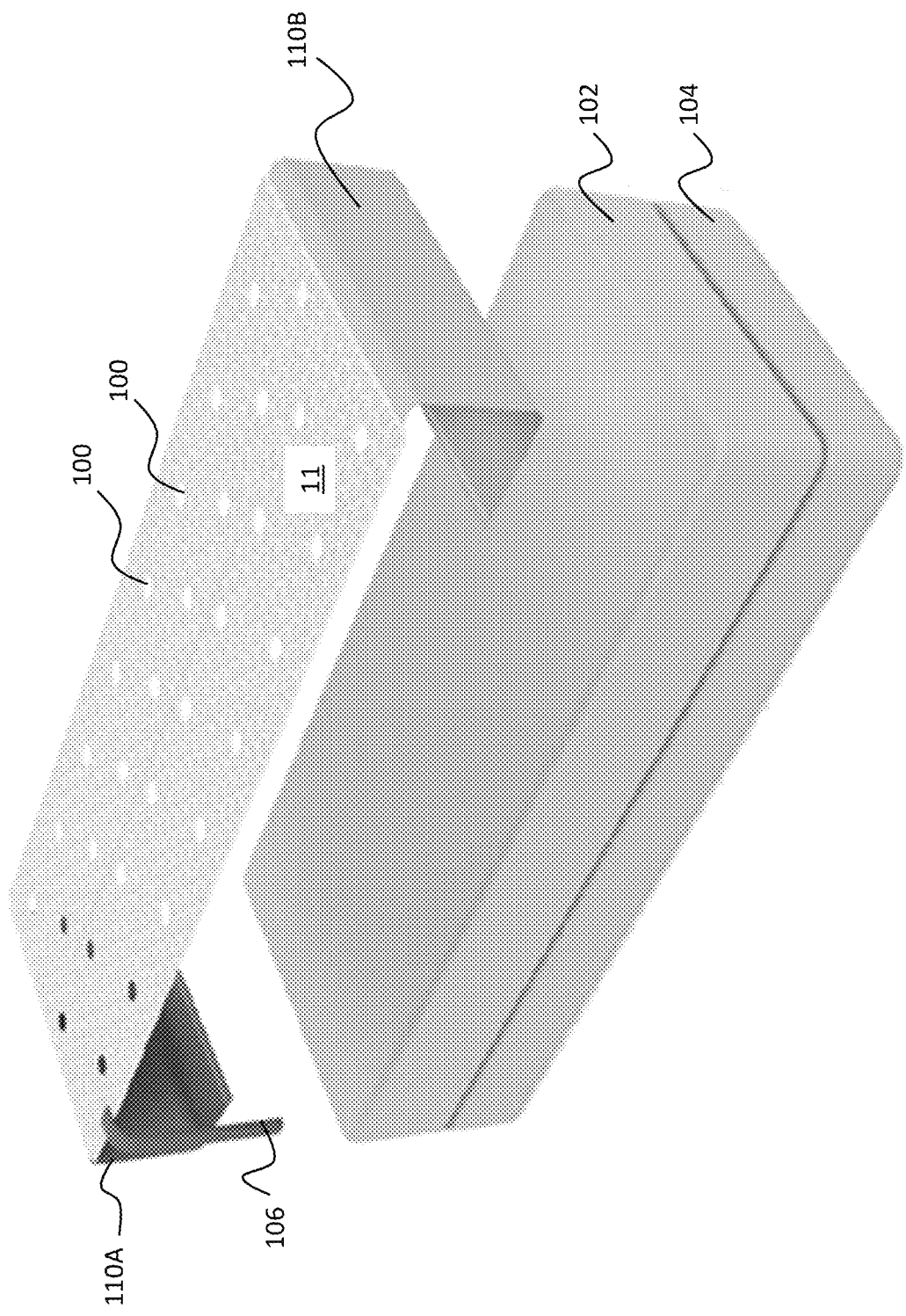
FIG. 13 is a top perspective view of a single mattress pad.

FIG. 13 is an exploded view of a single mattress pad. The mattress pad 11 is shown above the mattress 102 and the box springs or foundation 104. While in use, the mattress pad 11 is placed on top of the mattress 102. The ends of the mattress pad 11 are attached to panels 110A, 110B. Panels 110A, 110B are placed over the head and foot ends of the mattress 102, with the ends of the panels 110A, 110B sandwiched between the mattress 102 and box springs or foundation 104.

As previously described, the mattress pad 11 preferably contains a plurality of holes or openings 100 in the surface of the mattress pad 11. A first layer having a plurality of holes or openings is permanently affixed to a second layer having a plurality of holes or openings along a periphery of the mattress pad and a periphery of each of the plurality of holes or openings. At least one interior chamber is defined between an interior surface of the first layer and an interior surface of the second layer. The at least one interior chamber is constructed and configured to retain a fluid without leaking. The interior surface of the first layer and the interior surface of the second layer are made of at least one layer of a waterproof material.

In an alternative embodiment, the mattress pad does not contain a plurality of holes or openings in the surface in the mattress pad. A first layer is permanently affixed to a second layer along a periphery of the mattress pad. In one embodiment, the waterproof material is stretchable. In a preferred embodiment, the stretch rate of the waterproof material is equal to or greater than the stretch rate of surrounding materials (e.g., a mattress). Advantageously, this prevents the mattress pad from gathering and bunching underneath a user.

Figure 14:
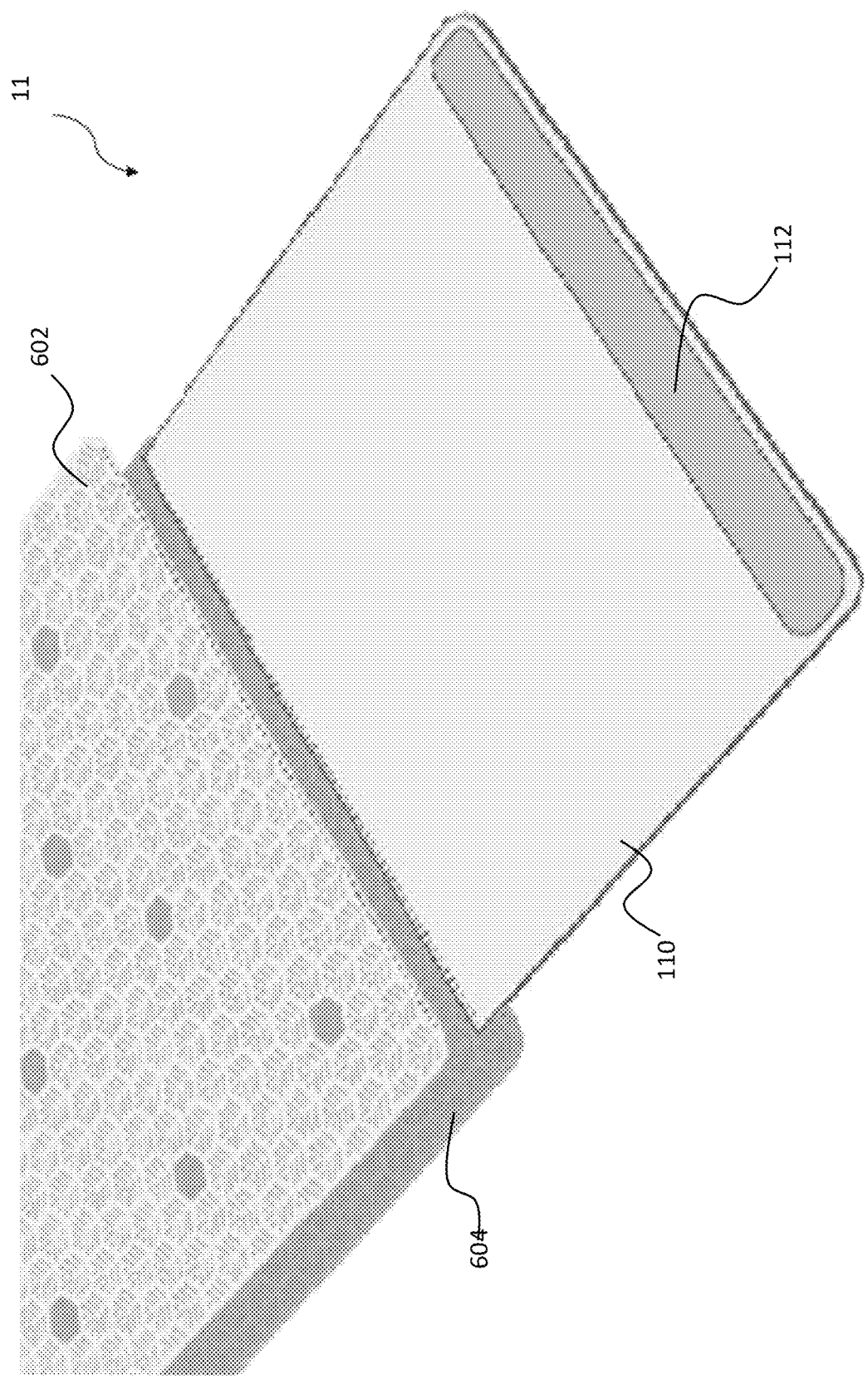
FIG. 14 is a top perspective view of an end of a single mattress pad.

FIG. 14 is an exploded view of an end of a single mattress pad. The mattress pad 11 is formed of at least two layers of waterproof material as shown in FIGS. 9A-9D. In one embodiment, the panel 110 is permanently affixed (e.g., sewn, adhered, welded) between a first layer of a waterproof material 602 and a second layer of a waterproof material 604. On the opposite end from where the panel 110 is attached to the mattress pad 11, a non-slip piece 112 is permanently affixed (e.g., sewn, adhered, welded) to the panel. In a preferred embodiment, the non-slip piece 112 is formed from foam. Alternatively, the non-slip pieces 112 are formed from latex, silicon, or rubber. The non-slip pieces 112 are preferably moisture wicking and/or antimicrobial.

Figure 15:
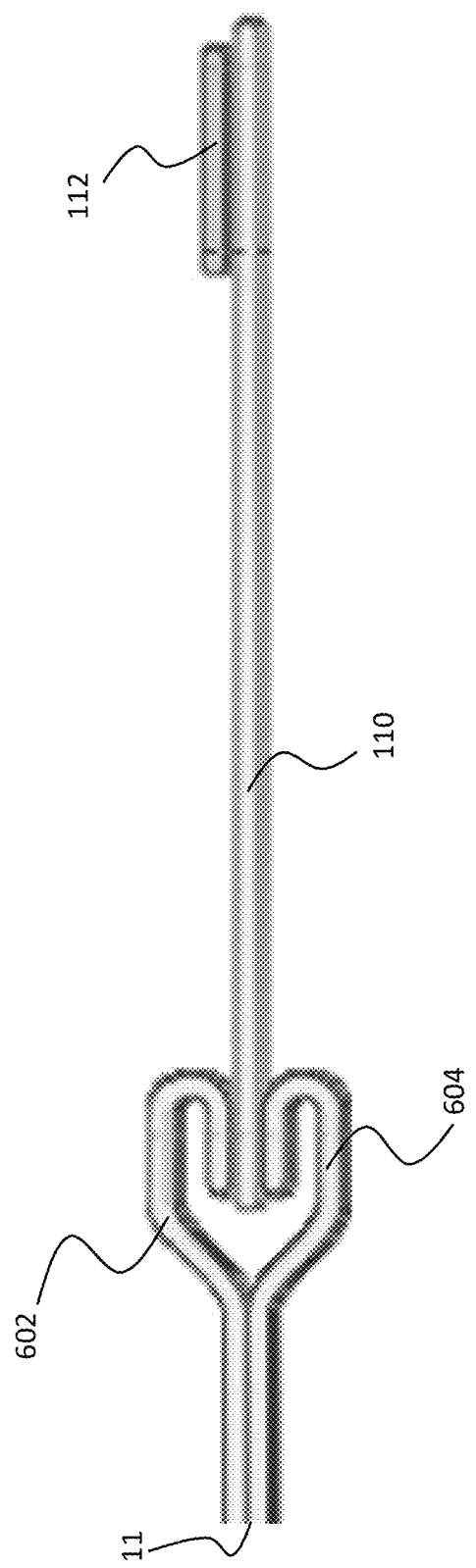
FIG. 15 is a side perspective view of an end of a single mattress pad.

FIG. 15 is a side perspective view of an end of a single mattress pad. The mattress pad 11 has a first layer of waterproof material 602 and a second layer of waterproof material 604. A first end of panel 110 is attached to the first layer of waterproof material 602 and the second layer of waterproof material 604. The panel 110 is permanently affixed (e.g., sewn, adhered, welded) between the first layer of waterproof material 602 and the second layer of waterproof material 604. In a preferred embodiment, the external surface of the first layer of waterproof material 602 and the second layer of waterproof material 604 are folded over to attach to the first end of panel 110. A non-slip piece 112 is permanently affixed (e.g., sewn, adhered, welded) to the end opposite of the first end of panel 110. In a preferred embodiment, the non-slip piece 112 is formed from foam. Alternatively, the non-slip pieces 112 are formed from latex, silicon, or rubber. The non-slip pieces 112 are preferably moisture wicking and/or antimicrobial.

In alternative embodiments, the mattress pad includes interlock or knit fabric on exterior surfaces of the mattress pad. In other embodiments, the exterior surfaces of the mattress pad are covered with a woven fabric, a non-woven fabric, or a polymer film (e.g., urethane or thermoplastic polyurethane (TPU)). Additionally or alternatively, the mattress pad includes a spacer layer between an interior surface of the first layer of waterproof material 602 and an interior surface of the second layer of waterproof material 604.

Figure 16:
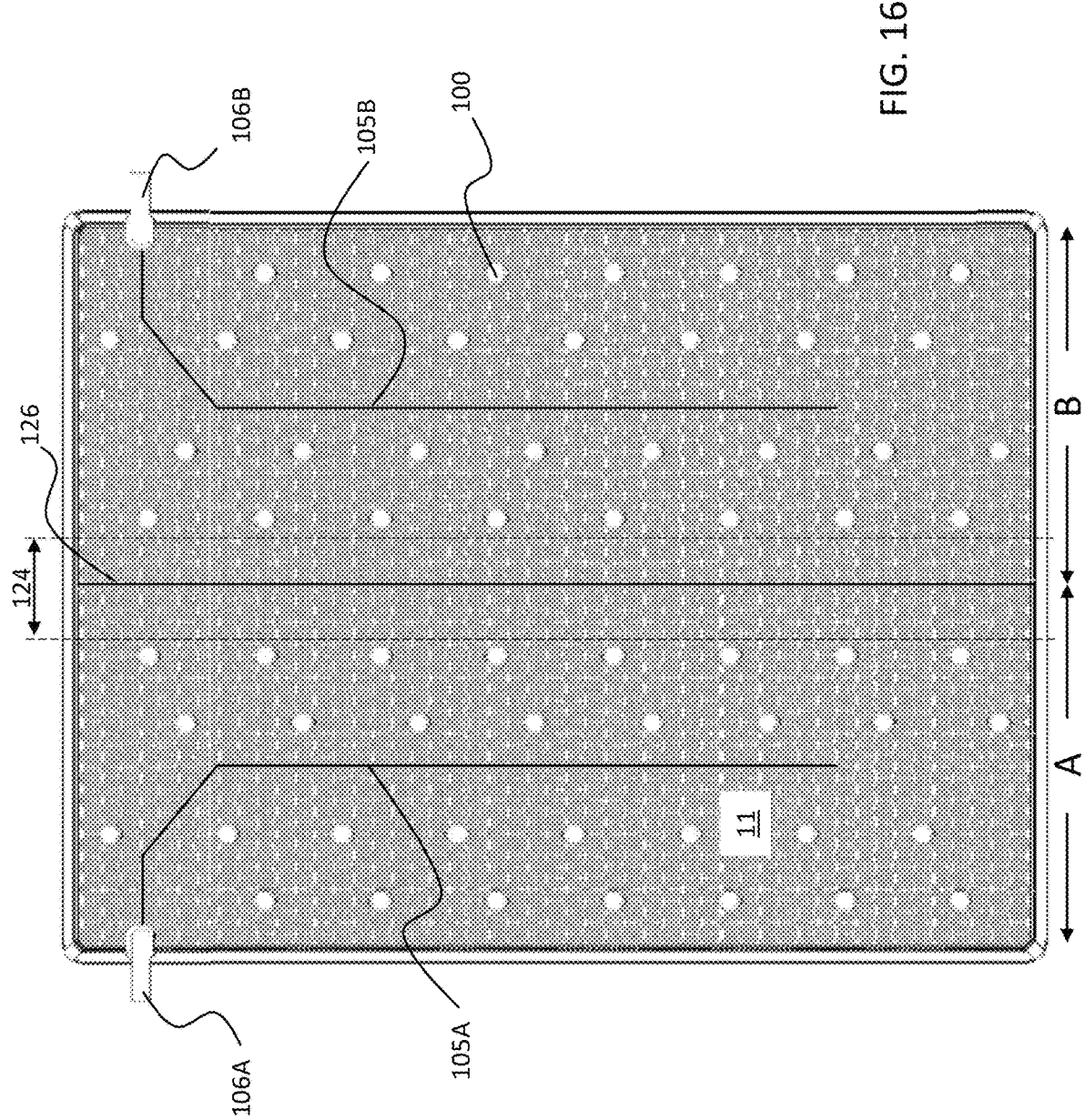
FIG. 16 is a top perspective view of a double mattress pad.

FIG. 16 is a top perspective view of a double mattress pad. The mattress pad 11 has two independent thermally regulated surface zones "A" and "B". The mattress pad 11 has a first flexible hose 106A and a second flexible hose 106B. In a preferred embodiment, the first flexible hose 106A attaches to a first control unit (not shown) and the second flexible hose 106B attaches to a second control unit (not shown). In a preferred embodiment, the center of the mattress pad 11 contains an area free of holes or openings 124. The area free of holes or openings 124 contains a welded separator 126, which provides a boundary between the two independent thermally regulated surface zones "A" and "B".

Figure 17:
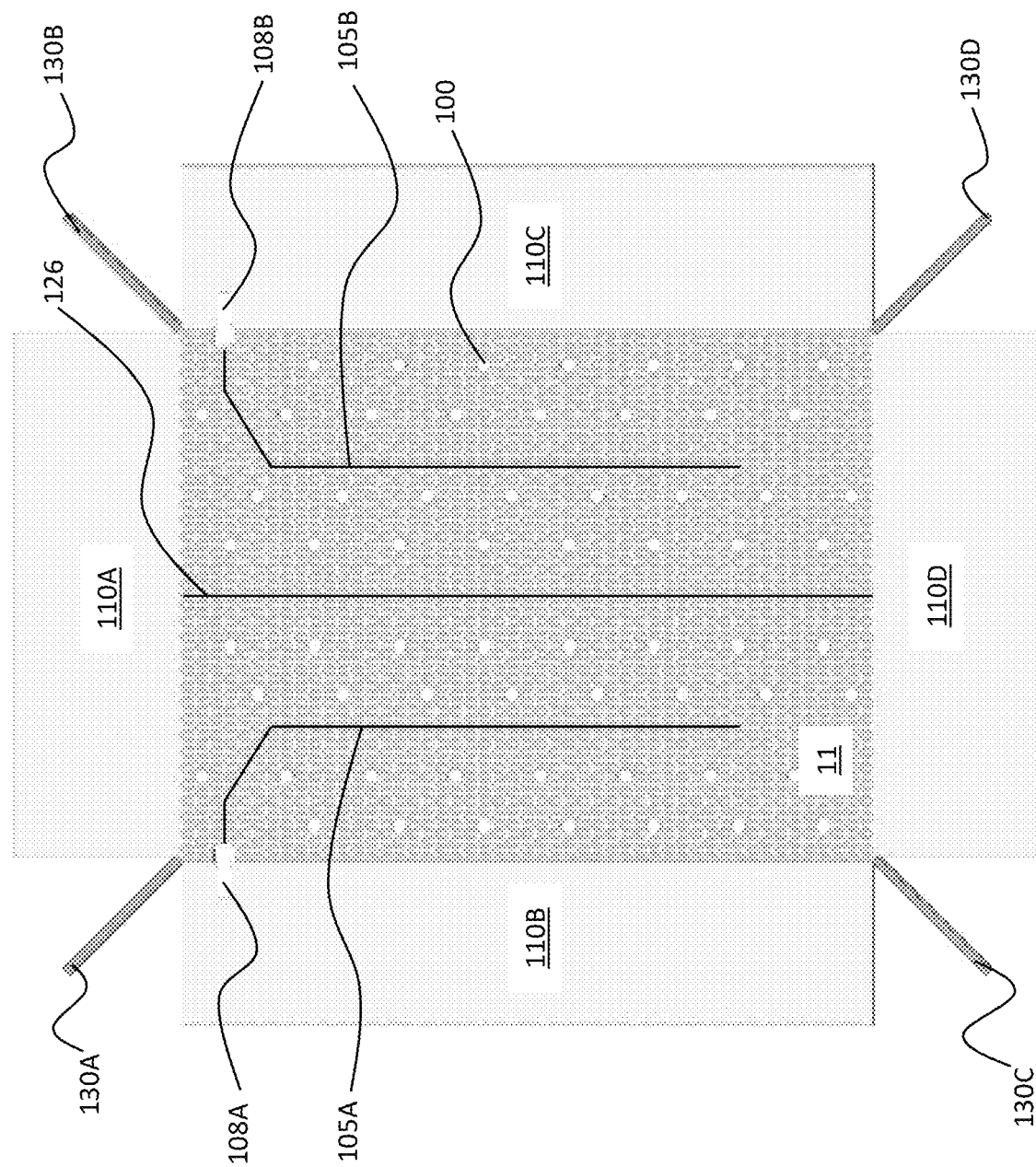
FIG. 17 is an exploded view of a double mattress pad.

FIG. 17 is another top perspective view of a double mattress pad. The mattress pad 11 has a top end panel 110A, a left side panel 110B, a right side panel 110C, and a bottom end panel 110D. The top end panel 110A, the left side panel 110B, the right side panel 110C, and the bottom end panel 110D are preferably formed from a material with stretch (e.g., interlock or knit). In a preferred embodiment, each corner of the mattress pad 11 contains at least one non-slip piece. In one embodiment, a top non-slip piece and a bottom non-slip piece are attached to each corner of the mattress pad 11. In the embodiment shown in FIG. 17, the corner between the top panel 110A and the left side panel 110B has a non-slip piece 130A, the corner between the top panel 110B and the right side panel 110C has a non-slip piece 130B, the corner between the left side panel 110B and the bottom end panel 110D has a non-slip piece 130C, and the corner between the right side panel 110C and the bottom end panel 110D has a non-slip piece 130D.

The mattress pad 11 preferably contains at least one weld line or other separation to help manage the flow of fluid in the at least one interior chamber. The at least one weld line 105 directs the fluid flow through the pad from head to foot, and returns the fluid to the control unit via the return line. In FIG. 17, the mattress pad has a first weld line 105A to help manage the flow of fluid in the interior chamber of zone "A" and a second weld line 105B to help manage the flow of fluid in the interior chamber of zone "B". Although only one weld line is shown for each independent temperature zone, it is equally possible to have two or more weld lines for each independent temperature zone.

Figure 18:
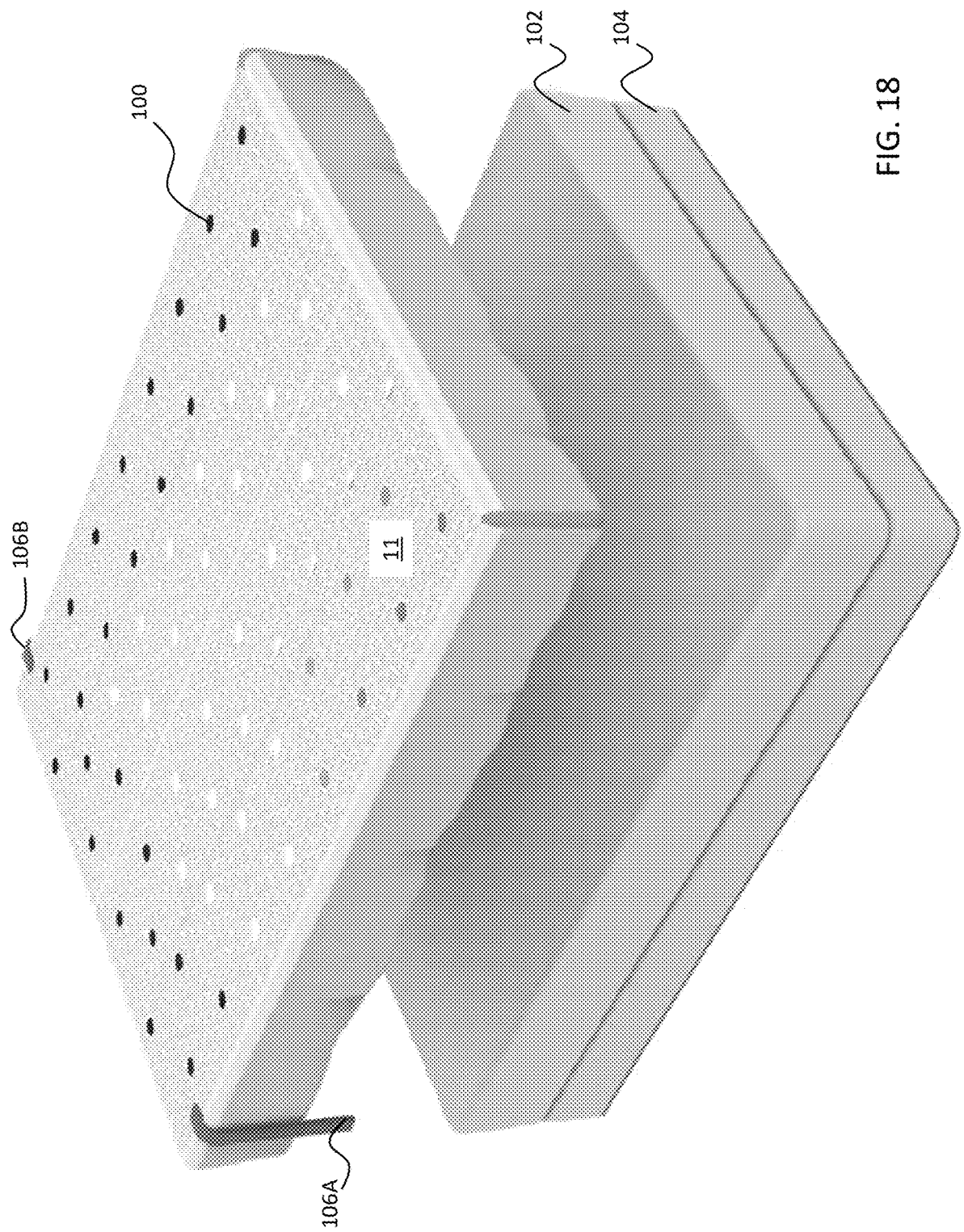
FIG. 18 is another top perspective view of a double mattress pad.

FIG. 18 is an exploded view of a double mattress pad. The mattress pad 11 is shown above the mattress 102 and the box springs or foundation 104. The mattress pad 11 has a first flexible hose 106A and a second flexible hose 106B. In a preferred embodiment, the first flexible hose 106A attaches to a first control unit (not shown) and the second flexible hose 106B attaches to a second control unit (not shown). Alternatively, the first flexible hose 106A and the second flexible hose 106B attach to the same control unit. The surface of the mattress pad 11 contains a plurality of holes or openings 100 in the surface of the mattress pad 11.

Figure 19:
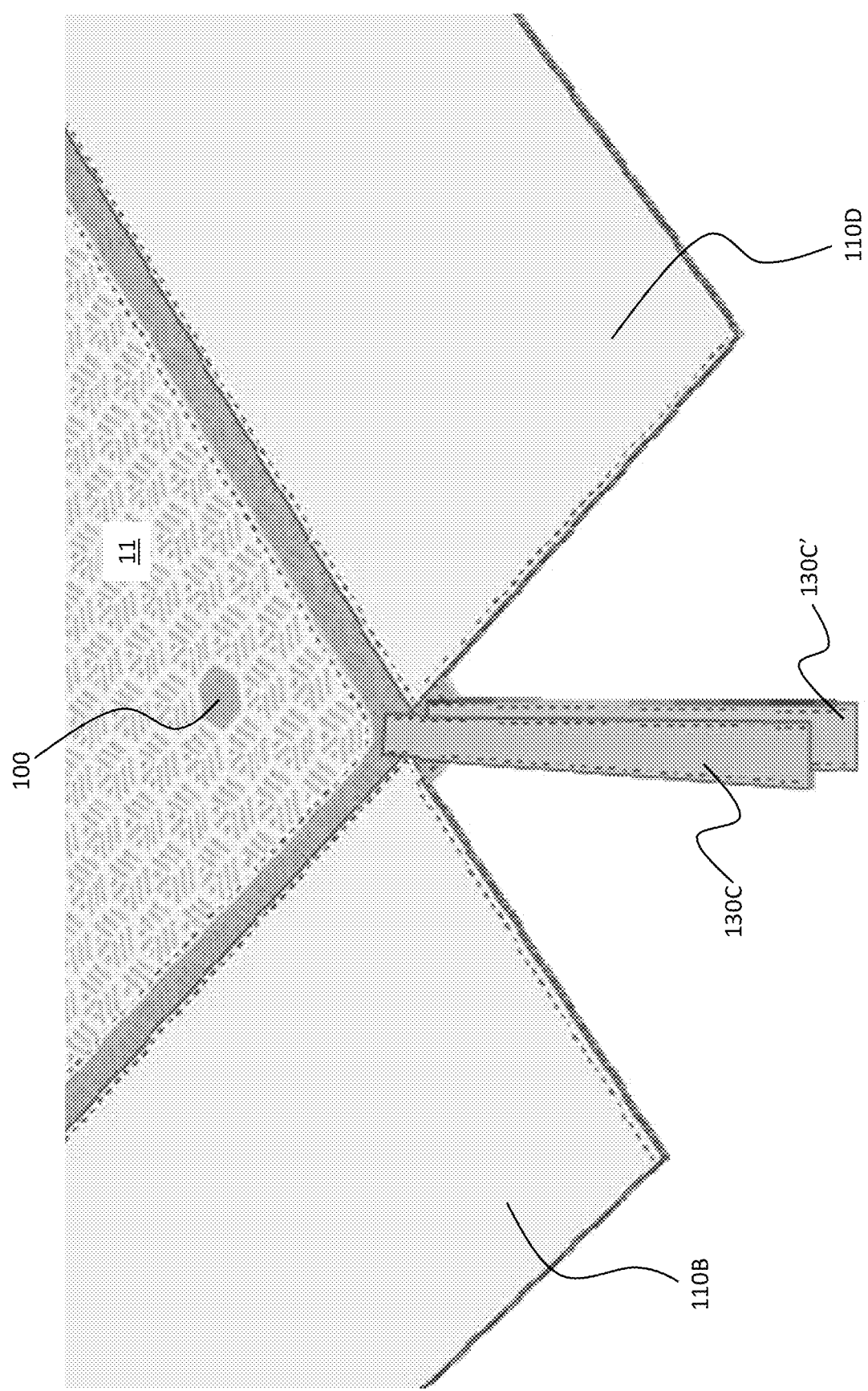
FIG. 19 is a view of the corner of a double mattress pad.

FIG. 19 is an exploded view of the bottom left corner of one embodiment of a double mattress pad before the mattress pad is secured to the bed. In a preferred embodiment, each corner of the mattress pad 11 contains a top non-slip piece 130C and a bottom non-slip piece 130C'. In FIG. 19, the top non-slip piece 130C and the bottom non-slip piece 130C' are shown attached (e.g., sewn, adhered, welded) to the corner formed between the left side panel 110B and the bottom end panel 110D. The left side panel 110B and the bottom end panel 110D are preferably formed from a material with stretch (e.g., interlock or knit). In one embodiment, elastic is attached (e.g., sewn, adhered, welded) to a bottom edge of the left side panel 110B and a bottom edge of the bottom end panel 110D. Alternatively, elastic is encased at the bottom edge of the left side panel 110B and the bottom edge of the bottom end panel 110D.

To secure the mattress pad 11 to the bed, the edge of the left side panel 110B and the edge of the bottom panel 110D are placed on top of the bottom non-slip piece 130C'. The top non-slip piece 130 is then placed on top the left side panel 110B, bottom panel 110D, and the bottom non-slip piece 130C'. The top non-slip piece 130C and bottom non-slip piece 130C' are preferably formed from non-slip foam. Alternatively, the top non-slip piece 130C and bottom non-slip piece 130C' are formed from silicone, rubber, or latex. In one embodiment, the left side panel 110B and the bottom panel 110D are formed from a material with stretch (e.g., interlock or knit). The top non-slip piece 130C and bottom non-slip piece 130C' provide friction to keep the mattress pad in place.

Figure 20:
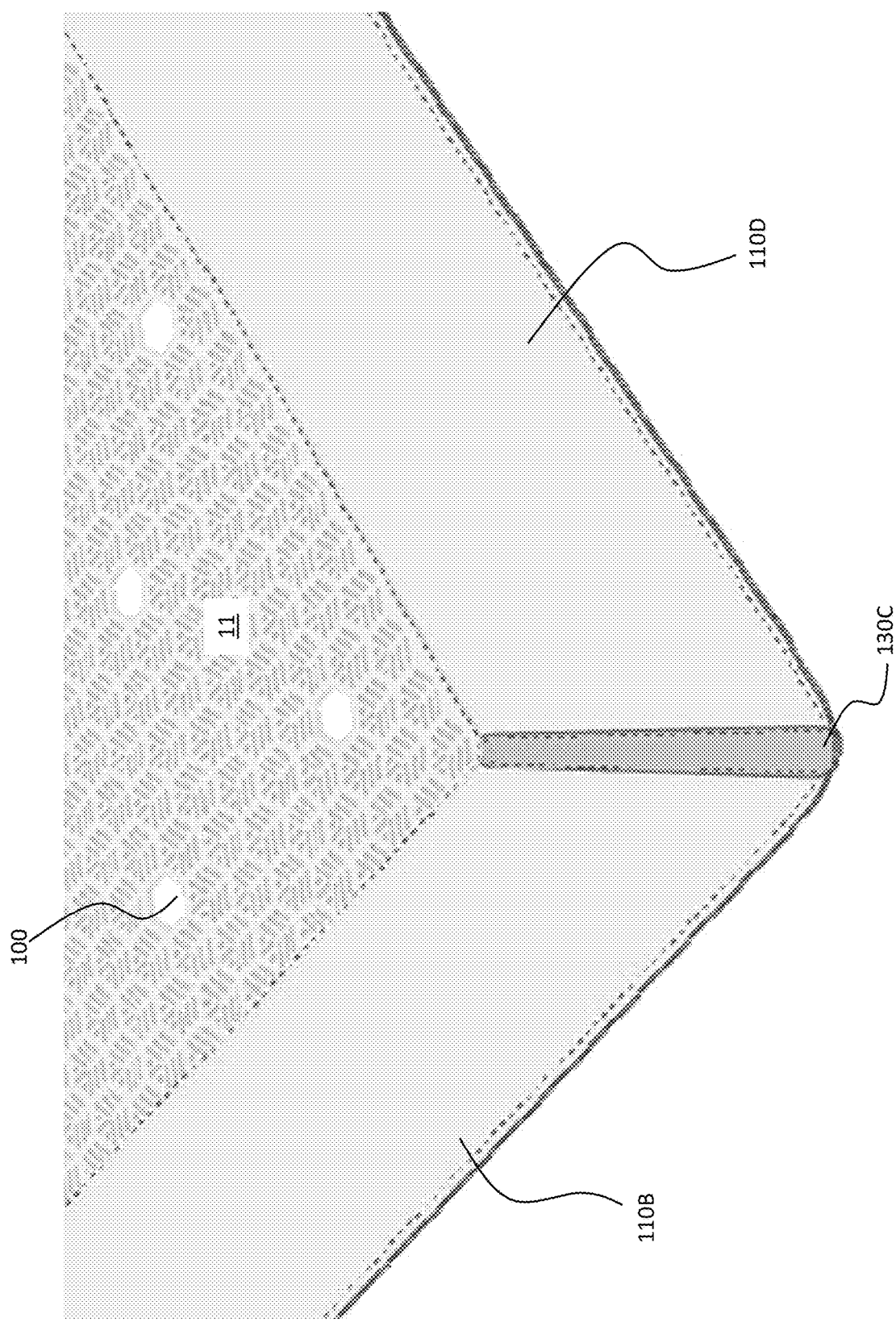
FIG. 20 is another view of the corner of a double mattress pad.

FIG. 20 is a view of the bottom left corner of a double mattress pad after the mattress pad is secured to the bed.

Figure 21:
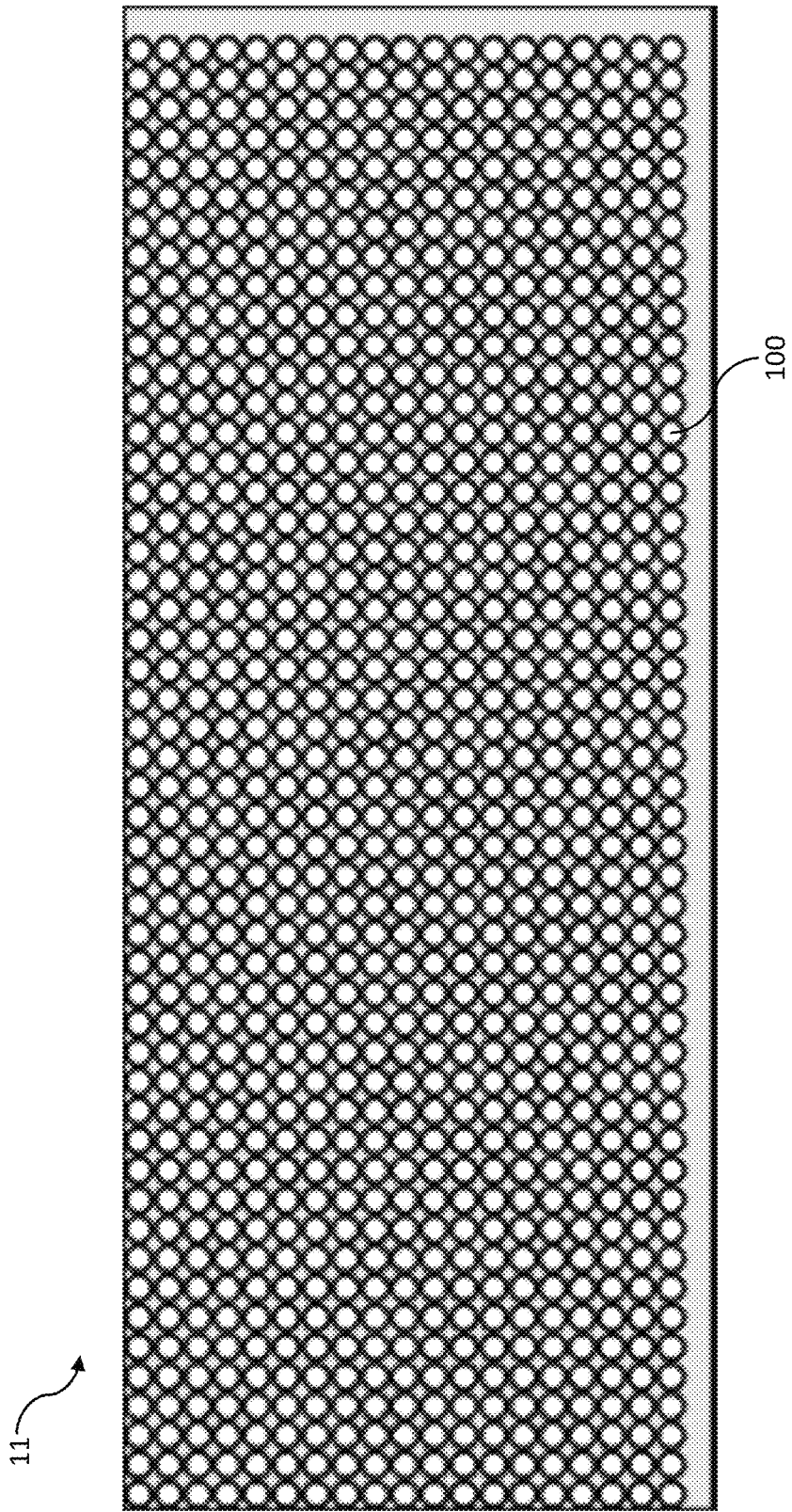
FIG. 21 is a view of another embodiment of a mattress pad.

FIG. 21 is a view of another embodiment of the mattress pad. The plurality of holes or openings 100 is shown in a circle shape in FIG. 21. The voids created by the plurality of holes or openings 100 include at least 80% of the surface area of the mattress pad 11 in this embodiment.

As mentioned previously, the at least one remote device is operable to programmatically control the target temperatures over time, such as over the course of a night's sleep. Because the target temperatures can be set at any time, those target temperatures can be manipulated through the sleeping period in order to match user preferences or a program to correlate with user sleep cycles to produce a deeper, more restful sleep.

The following documents provide general information regarding sleep and sleep monitoring, and are incorporated herein by reference in their entirety: (1) Iber et al. The AASM manual for the scoring of sleep and associated events: rules, terminology and technical specifications. 1st ed. Westchester, Ill.: American Academy of Sleep Medicine, 2007. (2) Berry et al. The AASM Manual for the Scoring of Sleep and Associated Events: Rules, Terminology, and Technical Specifications. www.aasm.org. Darien, Ill.: American Academy of Sleep Medicine, 2015. (3) Orem, et al. (Eds.). Physiology in Sleep. New York: Elsevier, 2012. (4) Sleep Research Society. Basics of Sleep Behavior. Los Angeles, Calif.: UCLA and Sleep Research Society, 1993. (5) Hirshkowitz, et al. The physiology of sleep. In Guilleminault (Ed.). Handbook of Clinical Neurophysiology—Clinical Neurophysiology of Sleep Disorders. Philadelphia: Elsevier, 2005; 3-20. (6) Avidian. Normal Sleep in Humans. In: Kryger, et al. (Eds.). Atlas of Clinical Sleep Medicine (2nd ed.). Philadelphia, Pa.: Elsevier, 2014; 70-97. (7) Consumer Technology Association. Definitions and Characteristics for Wearable Sleep Monitors, ANSI/CTA/NSF-2052.1, September 2016.

There are two main types of sleep: rapid eye movement (REM) sleep and non-rapid eye movement (non-REM) sleep. A sleep cycle typically lasts about 90 minutes, with REM sleep and non-REM sleep alternating within the sleep cycle. Non-REM sleep is divided into three stages: Stage 1 ("N1", drowsy sleep), Stage 2 ("N2", light sleep), and Stage 3 ("N3", deep sleep).

The N1 stage is a transitional stage between wakefulness and sleep, and is characterized as a very light and easily disrupted sleep. During N1 sleep, breathing becomes more regular and the heart rate slows. N1 sleep typically lasts less than 10 minutes and accounts for approximately 2-5% of total sleep time. The N2 stage is a deeper stage of sleep. N2 sleep accounts for approximately 45-50% of total sleep time because sleepers pass through the N2 stage multiple times throughout the night. The N3 stage is deep sleep. During N3 sleep, brain temperature, breathing rate, heart rate, and blood pressure are each at their lowest levels. Deep sleep is associated with repairing and regrowing tissues, building bone and muscle, and strengthening the immune system.

REM sleep is a stage of sleep associated with random movement of the eyes. REM sleep accounts for approximately 20-25% of total sleep time. The first period of REM sleep begins approximately 90 minutes after sleep begins and lasts for approximately 10 minutes. Further, REM sleep is more prevalent in the last half of a sleeping period, such that the last REM stage may last up to about 60 minutes. Heart rate, breath rate, and blood pressure increase during REM sleep. Additionally, due to high brain activity, dreams are more prevalent in REM sleep. REM is associated with preserving memories and building neural connections.

Because deep sleep and REM sleep are the most regenerative parts of the sleep cycle, it is most beneficial to spend most of a sleeping period in deep sleep and/or REM sleep. The target temperature of the mattress pad can be manipulated over time through programmatic control using the at least one remote device. Because the target temperature can be manipulated using the at least one remote device, those target temperatures can be manipulated through the sleeping period to allow a user to spend more time in REM and/or deep sleep.

Figure 22A:
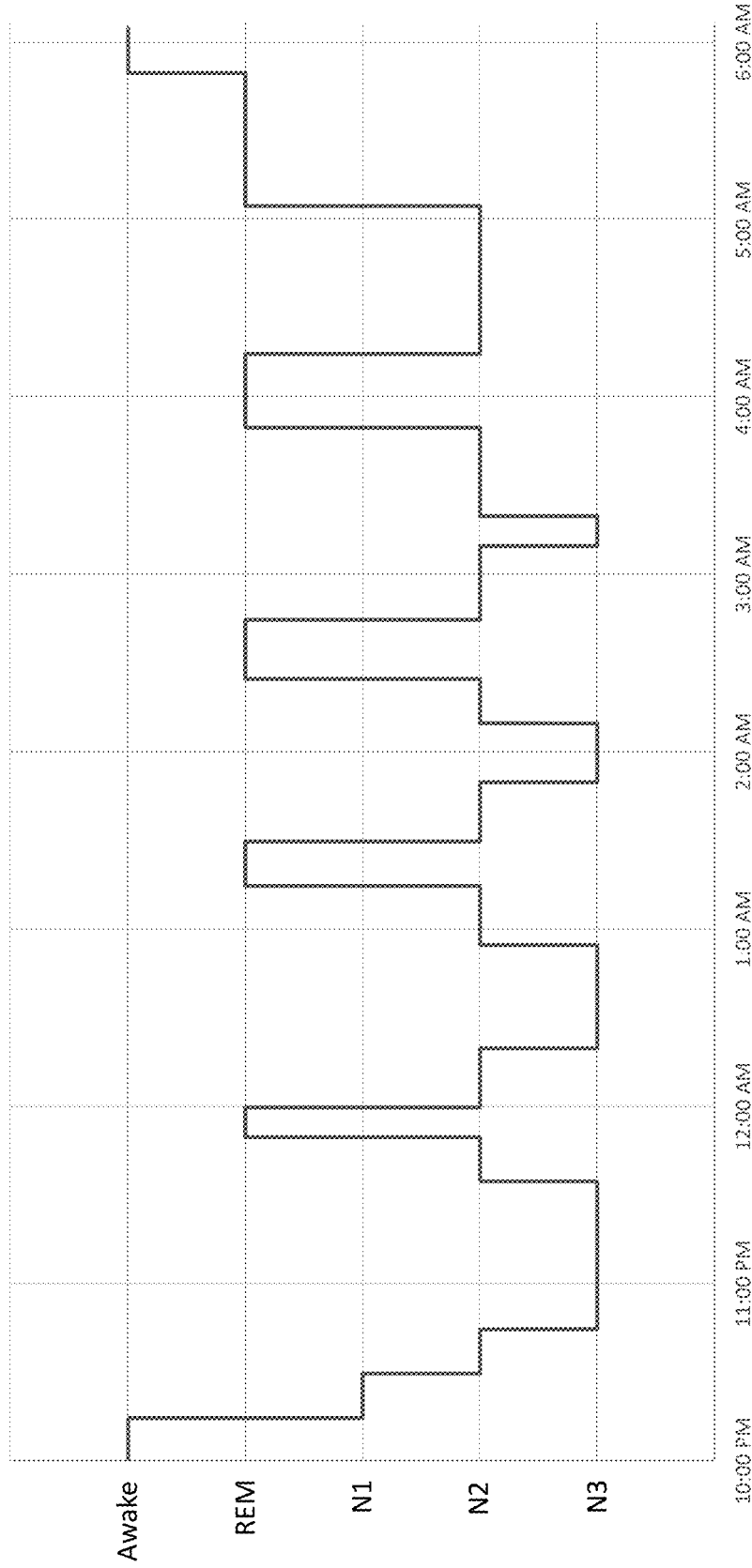
FIG. 22A illustrates a graph of a sleep cycle for a normal sleeper.

FIG. 22A illustrates a graph of the sleep cycle for a normal sleeper. A normal sleeper enters deep sleep 3-5 times in a sleeping period.

Figure 22B:
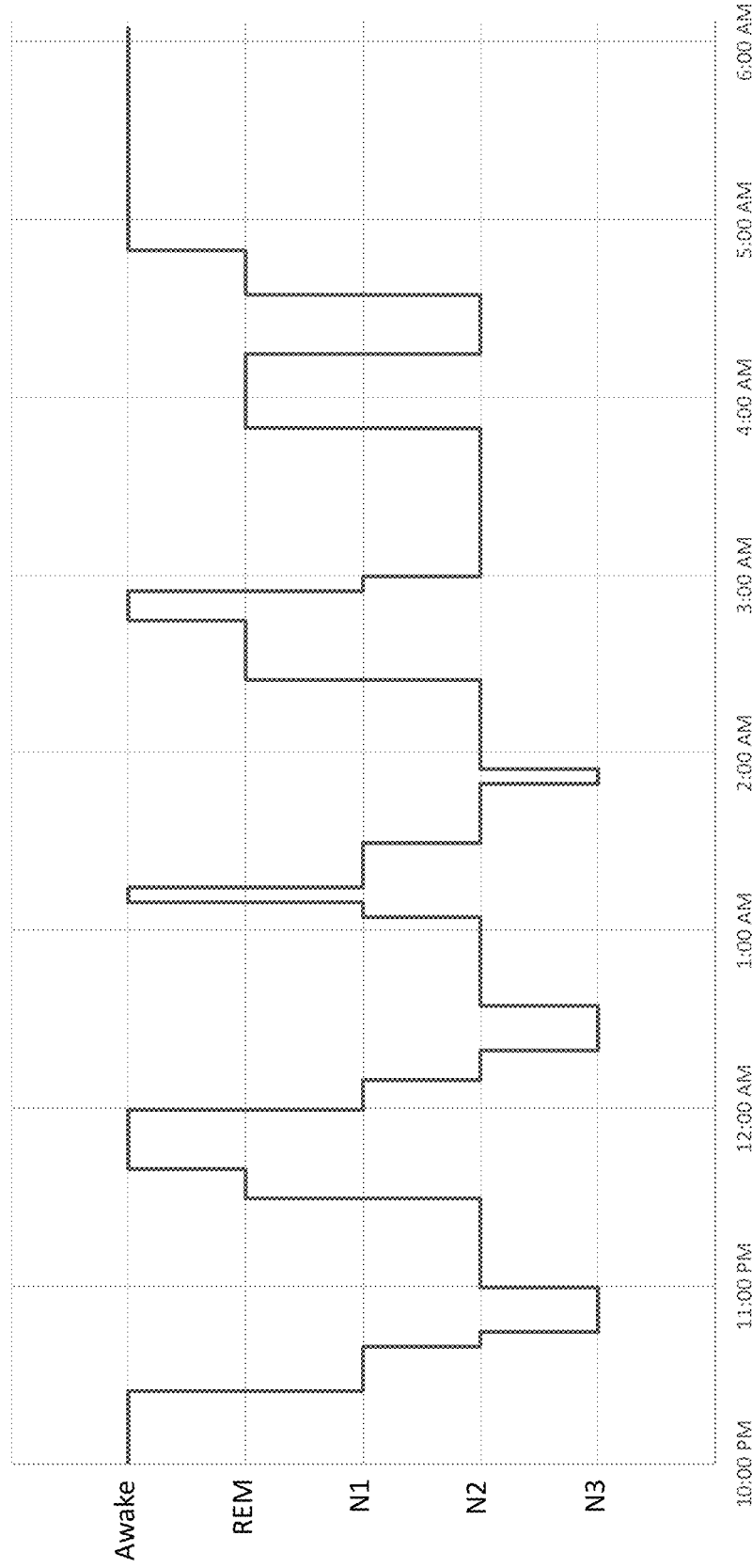
FIG. 22B illustrates a graph of a sleep cycle for a restless sleeper.

FIG. 22B illustrates a graph of the sleep cycle for a restless sleeper. Restless sleep is characterized by little or no deep sleep. Additionally, the sleep cycles are uneven. The sleeper may awaken several times throughout the night and have difficulty falling back asleep. Further, the time to sleep may be delayed and/or the sleeper may wake up earlier, as shown in FIG. 22B.

Figure 22C:
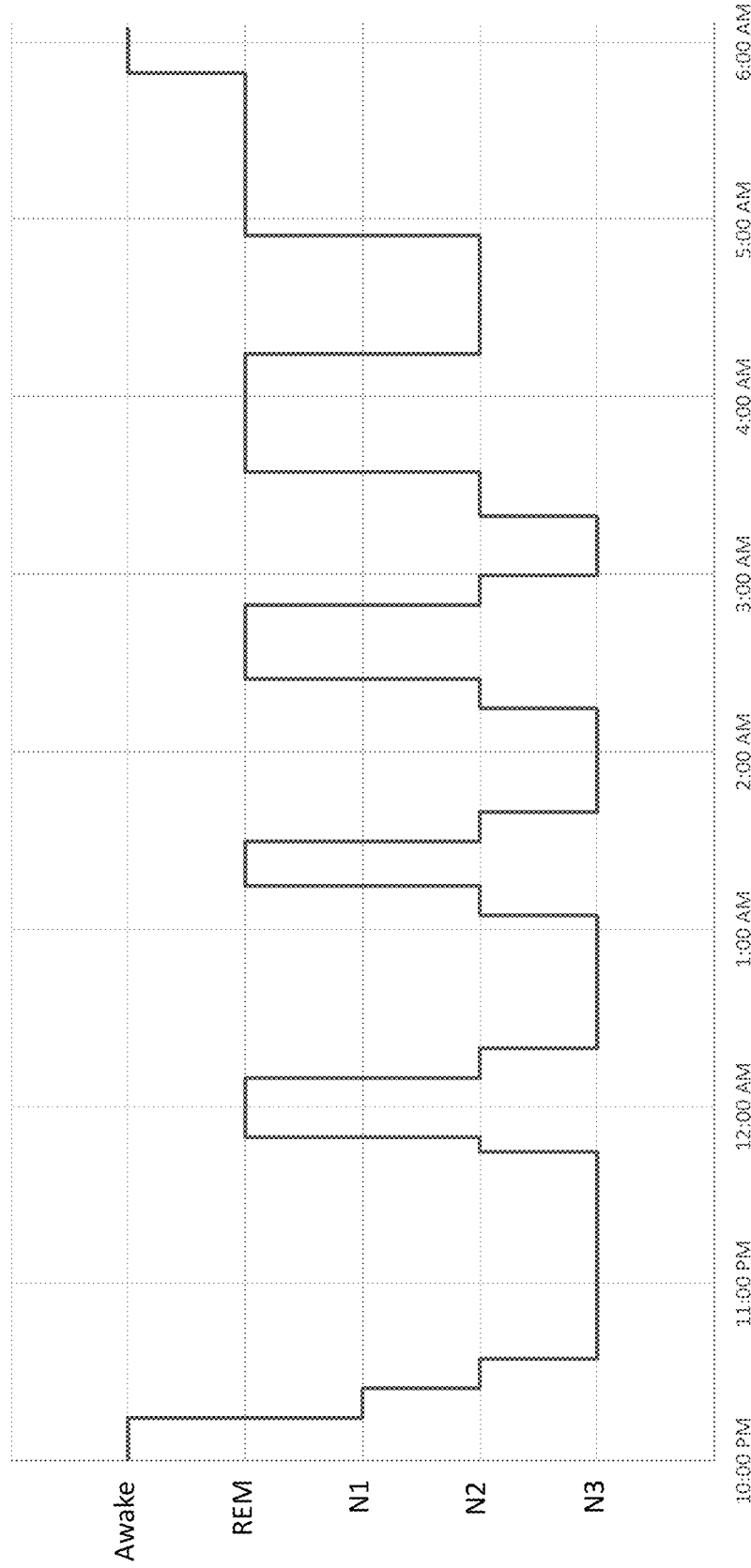
FIG. 22C illustrates a graph of a sleep cycle for a temperature-manipulated sleeper.

FIG. 22C illustrates a graph of the sleep cycle for a temperature-manipulated sleeper. The mattress pad cools the user to induce a sleep cycle. Additional cooling may be applied while the user is in deep sleep to extend the time spent in deep sleep. Slight warming (e.g., 0.278° C./minute (0.5° F./minute)) may be applied within a sleep cycle to move the user from deep sleep to REM sleep at a faster pace, such that less time is spent in N2 sleep. At the end of the last sleep cycle, the temperature is increased (e.g., 0.278° C./minute (0.5° F./minute)) to gently awaken the user. Advantageously, gently awakening the user by increasing the temperature prevents sleep inertia. Sleep inertia is characterized by impaired cognitive and motor function after awakening. It can take several hours to recover from sleep inertia, which presents a danger for individuals who need to make important decisions or perform tasks safely (e.g., driving).

PEMF Device

In a preferred embodiment, the stress reduction and sleep promotion system includes a Pulsed Electromagnetic Field (PEMF) device. PEMF therapy has many applications, including healing fractures, improving sleep, and treating migraines and depression. The PEMF device includes a power supply coupled to a circuit that produces an AC or DC output that is transmitted to at least one inductor coil. The inductor coil is formed of wire windings wrapped around a coil body with an open center or a ferrous core. The inductor coil emits an electromagnetic field (EMF) in response to the output from the circuit. In a preferred embodiment, the inductor coil is formed from copper.

The circuit produces a pulsed or time-varying output as a square wave, a sawtooth wave, a rectangular wave, a triangular wave, a trapezoidal wave, a sine wave, or an impulse. The pulsed or time-varying output can be at any voltage and/or frequency. The pulsed or time-varying output results in a pulsed or time-varying PEMF produced by the inductor coil. If the circuit produces an AC output, the positions of the north and south poles of the electromagnetic field change with each cycle. If the circuit produces a DC output, the positions of the north and south poles of the electromagnetic field remain constant.

The PEMF device includes at least one coil. In one embodiment, the PEMF device includes at least two coils per user. In a preferred embodiment, the PEMF device includes a pair of coils corresponding to a first region (e.g., head and neck), a pair of coils corresponding to a second region (e.g., torso and hips), and a pair of coils corresponding to a third region (e.g., legs and feet). In one example, the PEMF device includes six coils for a single user and twelve coils for two users (six coils per user). In other examples, the PEMF device includes two coils per user, three coils per user, four coils per user, five coils per user, seven coils per user, or eight coils per user.

In one embodiment, the PEMF device produces a magnetic field greater than about 10 gauss. In a preferred embodiment, the PEMF device produces a magnetic field of between about 80 and about 100 gauss. In yet another preferred embodiment, the PEMF device produces a square wave. In another embodiment, the intensity of the electromagnetic field is greater near the legs and feet and weaker near the head and neck.

Figure 23:
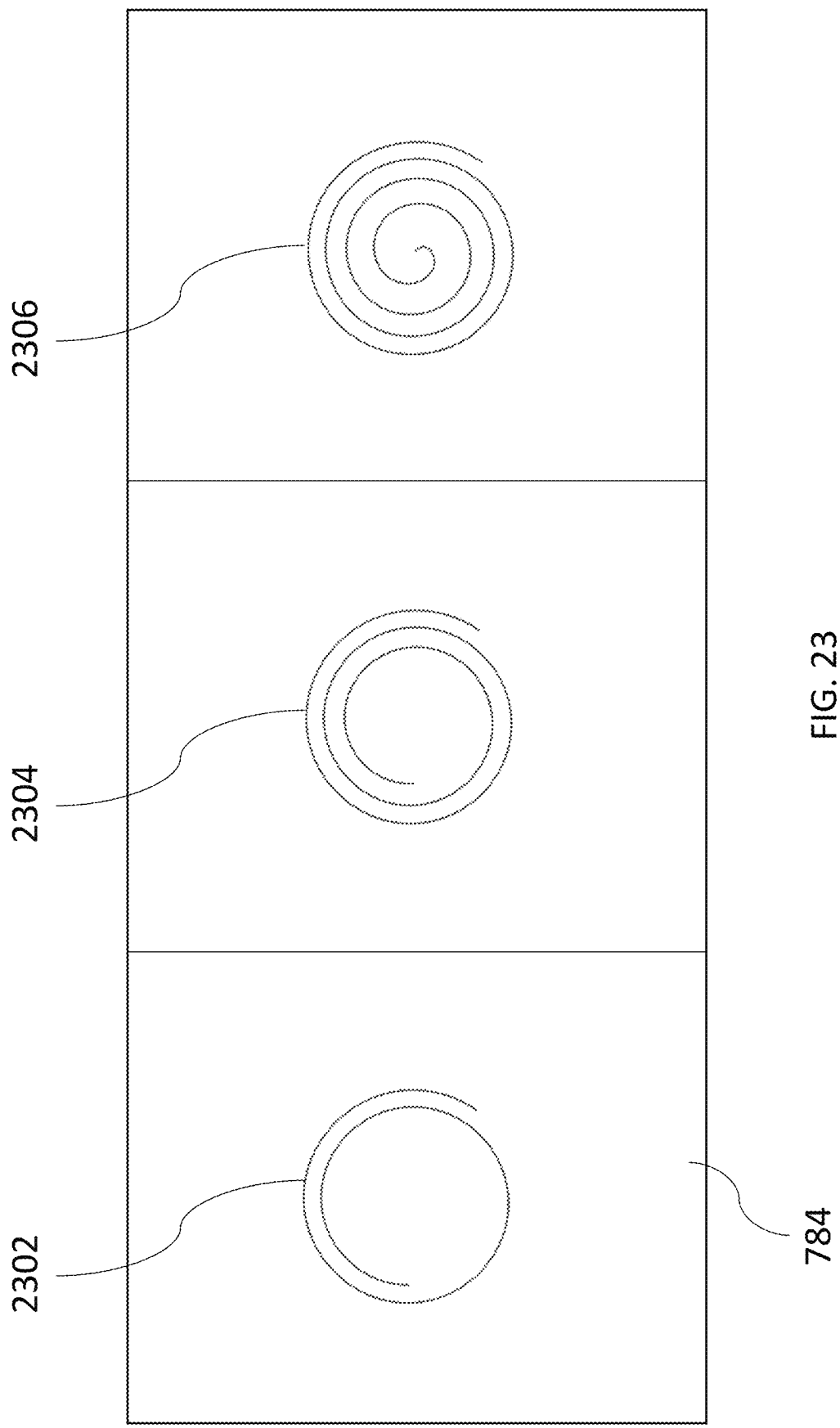
FIG. 23 illustrates an embodiment of a PEMF device with three coils.

FIG. 23 illustrates an embodiment of a PEMF device with three coils. In this embodiment, the PEMF device 784 is a mat with three coils. The PEMF device 784 includes a first coil 2302 corresponding to a first region (e.g., head and neck), a second coil 2304 corresponding to a second region (e.g., torso and hips), and a third coil 2306 corresponding to a third region (e.g., legs and feet). The third coil 2306 produces a stronger electromagnetic field than the second coil 2304, and the second coil 2304 produces a stronger electromagnetic field than the first coil 2302.

Figure 24:
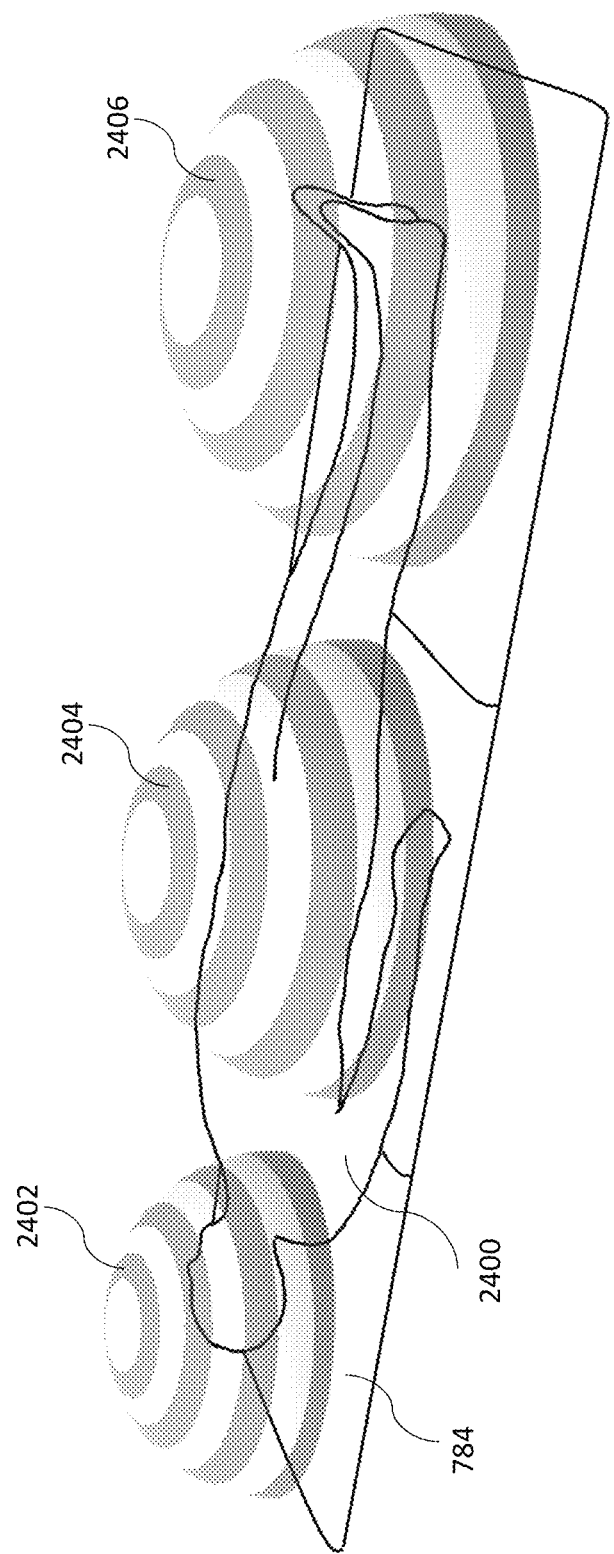
FIG. 24 illustrates the electromagnetic fields produced by the PEMF device of FIG. 23.

FIG. 24 illustrates the electromagnetic fields produced by the PEMF device of FIG. 23. In this embodiment, a user 2400 is positioned such that the user's back is against the mat. The three coils produce a first electromagnetic field 2402 corresponding to a first region (e.g., head and neck), a second electromagnetic field 2404 corresponding to a second region (e.g., torso and hips), and a third electromagnetic field 2406 corresponding to a third region (e.g., legs and feet). In a preferred embodiment, the third electromagnetic field 2406 is stronger than the second electromagnetic field 2404, and the second electromagnetic field 2404 is stronger than the first electromagnetic field 2402. Alternatively, the electromagnetic fields 2402, 2404, and 2406 are of the same strength.

FIG. 25 shows a table of frequencies and the effects on tissues. In one embodiment, the PEMF device produces a frequency between about 0 Hz and about 100 Hz. In a preferred embodiment, the PEMF device produces a frequency of about 10 Hz. In another preferred embodiment, the PEMF device produces a frequency between about 7 Hz and about 8 Hz. In yet another preferred embodiment, the PEMF device produces a frequency of about 2 Hz, about 15 Hz, and/or about 20 Hz. Advantageously, frequencies between about 0 Hz and about 30 Hz correspond to delta (0-4 Hz), theta (4-8 Hz), alpha (8-12 Hz), and beta (12-40 Hz) brainwaves. In one example, the PEMF device produces a frequency of about 2 Hz to promote sleep. The user's brainwaves slow to match the frequency generated by the PEMF device (i.e., 2 Hz) and, thus, promotes sleep.

Figure 26:
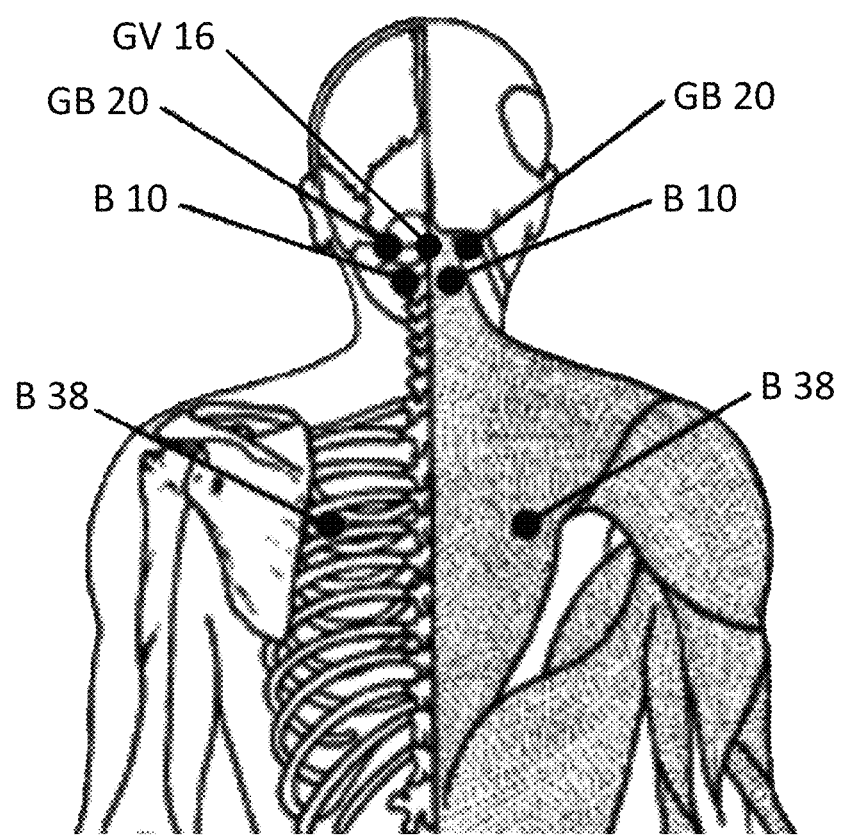
FIG. 26 illustrates selected acupressure points located in the upper body.

FIG. 26 illustrates selected acupressure points located in the upper body. In one embodiment, the PEMF device includes at least one coil corresponding to a region including acupressure points B10, GV16, and/or GB20. Acupressure point B10 is a significant acupressure point for relieving insomnia, stress, and exhaustion. Acupressure point GV16 aids in treating insomnia and sleeping disorders caused by stress and anxiety. Acupressure point GB20 provides relief from insomnia, fatigue, low energy, and headaches. Additionally or alternatively, the PEMF device includes at least one coil corresponding to a region including acupressure points B38. In one embodiment, the PEMF device includes one coil centered between acupressure points B38. In another embodiment, the PEMF device includes two coils corresponding to acupressure points B38 (i.e., one coil per acupressure point B38). Acupressure point B38 is an important acupressure point for treating sleep disorders and promoting restful sleep. Stimulating B38 helps in balancing negative emotions (e.g., stress, anxiety, grief, fear) that prevent sleep. In another embodiment, the PEMF device produces a magnetic field located over at least one meridian line used in Traditional Chinese Medicine. In yet another embodiment, the PEMF device produces a magnetic field isolated to a specific area.

In one embodiment, the PEMF device is incorporated into a mattress. In another embodiment, the PEMF device is operable to be placed under the box springs or foundation (e.g., on the floor). In yet another embodiment, the PEMF device is a pad placed on top of the mattress. In still another embodiment, the PEMF device is incorporated into a pillow. Alternatively, the PEMF device is a ring. Advantageously, the ring allows for localized treatment (e.g., neck, arm, leg).

The PEMF device preferably has at least one processor. By way of example, and not limitation, the processor may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information. In one embodiment, one or more of the at least one processor is operable to run predefined programs stored in at least one memory of the PEMF device.

The PEMF device preferably includes at least one antenna, which allows the PEMF device to receive and process input data (e.g., temperature settings, start and stop commands) from at least one remote device (e.g., smartphone, tablet, laptop computer, desktop computer, remote control). In a preferred embodiment, the at least one remote device is in wireless network communication with the PEMF device. The wireless communication is, by way of example and not limitation, radiofrequency, Bluetooth®, ZigBee®, Wi-Fi®, wireless local area networking, near field communication (NFC), or other similar commercially utilized standards. Alternatively, the at least one remote device is in wired communication with the PEMF device through USB or equivalent.

The PEMF device is operable to be used before a sleeping period to promote sleep, during a sleeping period to maintain sleep, and after a sleeping period to wake a user. In a preferred embodiment, different frequencies, patterns, and field lines are offered in programmable options. In one embodiment, the PEMF device includes settings for various conditions and/or body types (e.g., joint pain, depression, post-traumatic stress disorder, nightmares, back pain, multiple sclerosis, pinched nerves, asthma, swelling and inflammation, tissue repair, cell growth).

In one example, the PEMF device is used to aid a user in sleeping for a sleeping period of about 8 hours. The PEMF device starts at a recovery mode with a frequency of 9.6 Hz. After 15 minutes at 9.6 Hz, the frequency falls to 3 Hz and cycles between 3 Hz and 1 Hz four times in 7.25 hours. The polarity changes from north to south every about 30 minutes. For the final 15 minutes of the sleeping period, the frequency increases to 12 Hz and then 14.1 Hz to ensure the user wakes up.

In another example, the PEMF device is used to aid a user in sleeping for a sleeping period of about 8 hours. The PEMF device starts at a recovery mode with a frequency of 9.6 Hz. After 15 minutes at 9.6 Hz, the frequency drops from 9.6 Hz to 1 Hz over a 30-minute period. The frequency then cycles between 5 Hz and 1 Hz four times in 7.25 hours. The polarity changes from north to south every about 30 minutes. For the final 15 minutes of the sleeping period, the frequency increases to 12 Hz and then 14.1 Hz to ensure the user wakes up.

In yet another example, the PEMF device is used to aid a user in sleeping for a sleeping period of about 8 hours. The PEMF device starts at a recovery mode with a frequency of 9.6 Hz. After 15 minutes at 9.6 Hz, the frequency drops from 9.6 Hz to 1 Hz over a 30-minute period. The frequency then cycles between 5 Hz and 1 Hz six times in 7.25 hours. The polarity changes from north to south every about 30 minutes. For the final 15 minutes of the sleeping period, the frequency increases to 12 Hz and then 14.1 Hz to ensure the user wakes up.

In still another example, the PEMF device is used to aid a user who struggles to fall asleep. The PEMF device starts with a frequency at 3 Hz. The frequency cycles between 3 Hz and 1 Hz four times in 7.25 hours. The polarity changes from north to south every about 30 minutes. For the final 15 minutes of the sleeping period, the frequency increases to 12 Hz and then 14.1 Hz to ensure the user wakes up.

In one example, the PEMF device is used to aid a user who struggles to fall asleep. The PEMF device starts with a frequency at 1 Hz. The polarity changes from north to south every about 30 minutes. For the final 15 minutes of the sleeping period, the frequency increases to 14.1 Hz to ensure the user wakes up.

In another example, the PEMF device is used to aid a user in taking a power nap. The PEMF device maintains a frequency of 9.6 Hz for about 15 minutes to about 30 minutes.

TENS Device

In a preferred embodiment, the stress reduction and sleep promotion system includes a Transcutaneous Electrical Nerve Stimulation (TENS) device. TENS is a form of therapy that uses electrical stimulation for pain relief. Examples of a TENS device include U.S. Pat. Nos. 8,948,876, 9,675,801, and 9,731,126 and U.S. Publication Nos. 20140296935, 20140309709, and 20170056643, each of which is incorporated herein by reference in its entirety.

The TENS device preferably has a monophasic, a symmetric biphasic, or an asymmetric biphasic waveform. In one embodiment, the TENS device has a pulse amplitude between about 1 mA and about 50 mA. In another embodiment, the TENS device has a pulse duration between about 50 microseconds and about 500 microseconds. In yet another embodiment, the TENS device has a frequency between about 1 Hz and about 200 Hz. In still another embodiment, the TENS device has a continuous pulse pattern or a burst pulse pattern. The TENS device preferably has a single channel or double channels.

In one example, the TENS device is used to activate A-delta fibers. In this example, the TENS device uses a pulse frequency of between about 60 Hz and about 100 Hz with a pulse duration of less than 300 microseconds. The pulse frequency is preferably 80 Hz. The pulse duration is preferably between about 60 microseconds and about 100 microseconds. A treatment duration lasts between about 30 minutes and about 24 hours.

In another example, the TENS device is used to release β-endorphins. In this example, the TENS device uses a pulse frequency of less than 10 Hz and a pulse width between about 150 microseconds and about 300 microseconds. The pulse frequency is preferably between about 1 Hz and about 5 Hz. The pulse duration is preferably between about 200 microseconds and about 300 microseconds. A treatment duration lasts between about 20 minutes and about 40 minutes.

In yet another example, the TENS device is used stimulate active C fibers. In this example, the TENS device uses a pulse frequency of between about 60 Hz and about 100 Hz with a pulse duration of between about 200 microseconds and about 1000 microseconds. The pulse frequency is preferably 100 Hz. The pulse duration is preferably 200 microseconds. A treatment duration lasts between about 15 minutes and about 30 minutes.

Sound Generator

In a preferred embodiment, the stress reduction and sleep promotion system includes a sound generator. Sound can positively impact sleep, alleviate pain, manage stress, and promote wellness. Sounds can cause an individual to fall asleep, move between sleep stages, or wake. Sounds including, but not limited to, white noise, heartbeat, or environmental sounds (e.g., rain, ocean waves, thunderstorms, rainforests, wind, birds, river, waterfalls, city noise) can help users fall asleep and stay asleep.

The sound generator is preferably operable to generate sound both within and outside of the audible range for humans. In one embodiment, the sound generator is operable to generate low frequency sounds (i.e., below 20 Hz). These low frequency sounds accelerate healing and strengthen immune function. In another embodiment, the sound generator is operable to play at least one sound during a sleeping period. In yet another embodiment, the sound generator is operable to fade at least one sound to quiet.

In one embodiment, the sound generator is operable to play binaural beats. Binaural beats occur when two pure-tone sine waves of different frequencies are sent simultaneously to the left ear and the right ear. As a result, the brain perceives a third tone based on the difference between the two frequencies. The two pure-tone sine waves each have a frequency lower than 1500 Hz and differ in frequency by less than 40 Hz. In a preferred embodiment, the two pure-tone sine waves each have a frequency lower than 1000 Hz and differ in frequency by less than 30 Hz. For example, if a 500 Hz tone is presented to the left ear and a 510 Hz tone is presented to the right ear, the listener perceives a third tone (i.e., a binaural beat) correlating to a frequency of 10 Hz. Binaural beats may help induce mental states, including relaxation, meditation, and creativity.

In another embodiment, the sound generator is operable to play a guided meditation for a user. In one embodiment, the guided meditation includes exhalation and inhalation cues to reduce stress and/or promote sleep. In another embodiment, the guided meditation includes guided imagery (e.g., beach, meadow) to reduce stress and/or promote sleep. In yet another embodiment, the guided meditation includes physical directions for a user (e.g., allow the jaw to drop, wiggle the toes, open the hands).

In one embodiment, the sound generator is incorporated into the control unit of the mattress pad. Alternatively, the sound generator is incorporated into the alarm clock, the sunrise simulator, and/or the sunset simulator. In another embodiment, the sound generator is incorporated into the remote device.

Air Purification

In a preferred embodiment, the stress reduction and sleep promotion system includes an air purification system. The air purification system removes air pollutants and allergens from the sleep environment. The air purification system is a high-efficiency particulate arrestance (HEPA) filter, an activated carbon filter, a photocatalytic (e.g., titanium dioxide) filter, a polarized-media electronic air cleaner, a negative ion generator or ionizer, a germicidal UV lamp, a heat sterilizer, a size exclusion filter, and/or an electrostatic dust collector. In one embodiment, the air purification system is operable to change settings (e.g., on/off) through a third-party system and/or home automation system (e.g., Amazon® Alexa®, Apple® HomeKit™, Google® Home™, IF This Then That® (IFTTT®), Nest®).

Scent Generator

In a preferred embodiment, the stress reduction and sleep promotion system includes a scent generator to trigger relaxation and sleep and/or an awakened state. Some scents (e.g., lavender, vetiver, chamomile, ylang ylang, bergamot, sandalwood, marjoram, cedarwood, jasmine, vanilla, geranium, rose) trigger relaxation and sleep. Other scents (e.g., coffee, lemon, cinnamon, mint, orange, grapefruit, rosemary) trigger an awakened state.

In one embodiment, the scent generator includes at least one scent cartridge that is activated by temperature. The at least one scent cartridge comprises scents to trigger relaxation and sleep and scents to trigger an awakened state in a preferred embodiment. Examples of scent generators including at least one scent cartridge include U.S. Pat. Nos. 6,581,915, 6,834,847, 7,160,515, 7,223,361, 7,691,336, 7,981,367, 8,016,207, 8,061,628, 8,119,064, 8,210,448, 8,349,251, 8,651,395, and 8,721,962 and U.S. Publication Nos. 20140377130, 20150048178, 20170070845, and 20170076403, each of which is incorporated herein by reference in its entirety.

In an alternative embodiment, the scent generator is at least one diffuser. In one embodiment, the at least one diffuser is incorporated into the control unit of the mattress pad. Alternatively, the at least one diffuser is incorporated into the alarm clock, the sunrise simulator, and/or the sunset simulator. In yet another embodiment, the at least one diffuser is incorporated into a headboard. Examples of a diffuser include U.S. Pat. Nos. 5,805,768, 7,878,418, 9,126, 215, 9,358,557, 9,421,295, 9,511,166, 9,517,286, and 9,527, 094 and U.S. Publication No. 20160243576, each of which is incorporated herein by reference in its entirety.

In another embodiment, the housing of the control unit is infused with a scent to trigger relaxation and sleep. A method of infusing a plastic with a scent is described in U.S. Pat. No. 7,741,266, which is incorporated herein by reference in its entirety. Alternatively, the mattress pad, the mattress, or bedding (e.g., sheets, comforter, pillowcase) is infused with a scent to trigger relaxation and sleep. In yet another embodiment, the scent generator is incorporated into the humidifier and/or the dehumidifier.

Lighting

The stress reduction and sleep promotion system is operable to control lighting in a room and/or a house. In one embodiment, the lighting includes at least one smart light bulb (e.g., Philips® Hue™, Cree® Connected®, C by GE®). In a preferred embodiment, the stress reduction and sleep promotion system is operable to change a color and/or intensity of the lighting. In one example, the stress reduction and sleep promotion system includes blue light in the morning to wake an individual and reduces the blue light at night to promote sleep. In another example, the stress reduction and sleep promotion system dims the lighting at night and increases the intensity of the lighting in the morning. In one embodiment, the stress reduction and sleep promotion system integrates with an external application and/or home automation system (e.g., Amazon® Alexa®, Apple® HomeKit™, Google® Home™, IF This Then That® (IFTTT®), Nest®) to control the lighting.

In one embodiment, the stress reduction and sleep promotion system includes a red light and/or near-infrared lighting device. The red light and/or near-infrared lighting device includes at least one red light and/or at least one near-infrared light. Red light therapy stimulates production of collagen and elastin, reduces inflammation and joint pain, improves the appearance of wrinkles and stretch marks, reduces acne and eczema, increases circulation, and improves healing of wounds and injuries. Further, red or near-infrared light at night may aid in the production of melatonin and promote sleep.

In one embodiment, the at least one red light and/or the at least one near-infrared light is a light-emitting diode (LED). In another embodiment, the red light and/or near-infrared lighting device emits a wavelength of light between about 600 nm and about 1000 nm, and more preferably between about 660 nm and about 670 nm and/or between about 830 nm and about 850 nm. Alternatively, the red light and/or near-infrared lighting device emits a wavelength of light between about 1400 nm and about 1600 nm (e.g., 1450 nm, 1550 nm). The red light and/or near-infrared lighting device produces a continuous wave or pulsed wave. In one embodiment, the red light and/or near-infrared lighting device produces a pulsed wave with a frequency between about 10 Hz and about 40 Hz.

Light also helps the body synchronize to a 24-hour day. In one embodiment, the stress reduction and sleep promotion system includes a sunrise simulator consisting of a light that gradually increases in brightness to wake a user. Bright lights can increase levels of alertness and boost mood. In one embodiment, the sunrise simulator is operable to take about 15 minutes, about 30 minutes, about 45 minutes, about 60 minutes, or about 90 minutes to reach full brightness. In one example, the sunrise simulator is operable to take about 30 minutes to increase light from 0 percent of full brightness (i.e., light off) to 100 percent of full brightness. In another embodiment, the sunrise simulator is incorporated into the alarm clock.

Additionally or alternatively, the stress reduction and sleep promotion system includes a sunset simulator that gradually decreases in brightness to relax a user and promote sleep. In one embodiment, the sunset simulator is operable to take about 15 minutes, about 30 minutes, about 45 minutes, about 60 minutes, or about 90 minutes to reach full darkness. In one example, the sunset simulator is operable to take about 30 minutes to decrease light from 100 percent of full brightness to 0 percent of full brightness (i.e., light off). In another embodiment, the sunset simulator is incorporated into the alarm clock.

Environmental Controls

In a preferred embodiment, the stress reduction and sleep promotion system is operable to control the room temperature, the fan, the humidifier, and/or the dehumidifier settings (e.g., on/off, temperature up, temperature down). In one embodiment, the stress reduction and sleep promotion system is operable to change the settings through a third-party system and/or home automation system (e.g., Amazon® Alexa®, Apple® HomeKit™, Google® Home™, IF This Then That® (IFTTT®), Nest®).

Alarm Clock

In a preferred embodiment, the stress reduction and sleep promotion system includes an alarm clock. In one embodiment, the alarm clock is incorporated in the remote device.

In another embodiment, the alarm clock includes the sunrise simulator and/or the sunset simulator.

Corrective EMF

In one embodiment, the stress reduction and sleep promotion system includes a device that emits a corrective signal to target electromagnetic fields (EMF). EMFs are the radiation associated with the use of electrical power and different forms of lighting (e.g., natural, man-made). These EMFs may cause stress to the body, which triggers a decrease in energy and an immune response. Further, EMFs may decrease the production of melatonin in the body. Symptoms of exposure to EMFs may include headaches, fatigue, irritability, depression, insomnia, poor memory, and/or shortness of breath.

In a preferred embodiment, the corrective signal is a harmonic resonance that interacts with EMFs. In one embodiment, the device emits a corrective resonance through electronic devices plugged into circuitry of a bedroom, a home, or an office. In another embodiment, the device is worn on a user's body (e.g., necklace).

Static Magnetic Therapy

In one embodiment, the stress reduction and sleep promotion system includes a device for generating static magnetic fields. Static magnets are often used in bracelets, shoe inserts, necklaces, and bedding to subtly influence the tissues that come in contact with the magnets and its static magnetic field. A static magnetic field exhibits no change in the flux density or intensity over the time interval of use or measurement. Static magnetic fields may improve pain and aid with sleep disorders. In a preferred embodiment, the static magnetic fields are used to stimulate a user's body along acupuncture Meridian lines.

In a preferred embodiment, the device for generating static magnetic fields includes a plurality of magnets to produce a negative magnetic field directed towards a sleep surface and a positive magnetic field directed away from the sleep surface. The device for generating static magnetic fields is positioned above a mattress or between the mattress and the box springs or foundation. One example of a device for generating static magnetic fields is described in U.S. Pat. No. 6,702,730, which is incorporated herein by reference in its entirety. In one embodiment, the plurality of magnets is formed from ceramic or neodymium magnets. In another embodiment, the plurality of magnets is formed from electromagnets.

The device for generating static magnetic fields is operable to generate a magnetic field greater than about 0.5 gauss. The Earth's magnetic field averages 0.5 gauss and completely penetrates the body, so a static magnet with a field strength lower than 0.5 gauss would not be expected to be active. In a preferred embodiment, the device for generating static magnetic fields is operable to generate a magnetic field between about 300 gauss to about 3000 gauss.

Grounding/Earthing

In a preferred embodiment, the stress reduction and sleep promotion system includes a device for grounding or earthing a user's body. Grounding or earthing is a practice whereby individuals connect themselves electrostatically to the earth by walking barefoot outdoors or by using grounded conductive mats, bed sheets, or body bands when indoors. Grounding is based on the theory that the earth is a source of negatively charged free electrons, and, when in contact with the earth, the body can use these free electrons as antioxidants to neutralize free radicals within the body. Research published over the last decade reports a broad array of health-related results, including improved sleep, decreased pain, normalizing effect on cortisol, reduction and/or normalization of stress, diminished damage to muscles caused by delayed onset muscle soreness, reduction of primary indicators of osteoporosis, improved glucose regulation, and enhanced immune function. In one embodiment, a surface in contact with the body (e.g., mattress pad, a sheet) is attached to a wire that is electrically connected to an electrical outlet ground port. Alternatively, the surface in contact with the body is attached to a wire that is connected to a ground rod. Examples of a device for grounding the body are described in U.S. Pat. Nos. 6,683,779, 7,212,392, and 7,724,491, each of which is incorporated herein by reference in its entirety.

Far Infrared Reflection

In a preferred embodiment, the stress reduction and sleep promotion system includes far infrared reflection technology (e.g., Celliant®, Redwave®). The far infrared reflection technology absorbs and converts body heat into infrared (IR) energy that increases blood flow to muscles and tissues in the body. The far infrared reflection technology is formed from polyethylene terephthalate fibers (e.g., Celliant®) or incorporates bioceramics (e.g., Redwave®). In one embodiment, the far infrared reflection technology is included in a set of sheets, a bed covering (e.g., comforter, duvet, duvet cover), or a mattress cover. In another embodiment, the far infrared reflection technology is included in sleepwear.

Electromagnetic Fields Blocking

In a preferred embodiment, the stress reduction and sleep promotion system includes electromagnetic fields blocking. Electromagnetic fields (EMFs) are present in modern daily life due to wireless technologies (e.g., Wi-Fi), power lines, cellular phones and cellular phone towers, cordless phones, electrical wiring in homes and businesses, appliances (e.g., televisions, microwaves), computers, radios, smart meters, and lighting. Some researchers advocate for shielding against EMFs, especially while sleeping, because this is when the body repairs itself. Electromagnetic fields may disrupt production of melatonin, which is responsible for regulating daily sleep/wake cycles. This may lead to long-term health effects, including suppression of the immune system.

In one embodiment, a Faraday cage blocks the EMFs. The Faraday cage includes at least one shielding fabric to protect a bed or sleep space from EMFs. The at least one shielding fabric is comprised of at least one base material and at least one metal. The at least one base material is polyester, cotton, rayon, silk, bamboo and/or nylon. The at least one metal is silver, copper, nickel, cobalt, and/or tin. In a preferred embodiment, a first shielding fabric is placed under the bed or the mattress and a second shielding fabric is placed above the bed as a canopy that surrounds the bed.

A Faraday cage may block wireless transmissions of data from the at least one body sensor. In one embodiment, the at least one body sensor obtains measurements before or after a sleeping period. In another embodiment, the at least one body sensor collects and stores data during a sleeping period. The at least one body sensor is operable to transmit the data to the at least one remote device after the sleeping period.

Integrated Bed System

Figure 27:
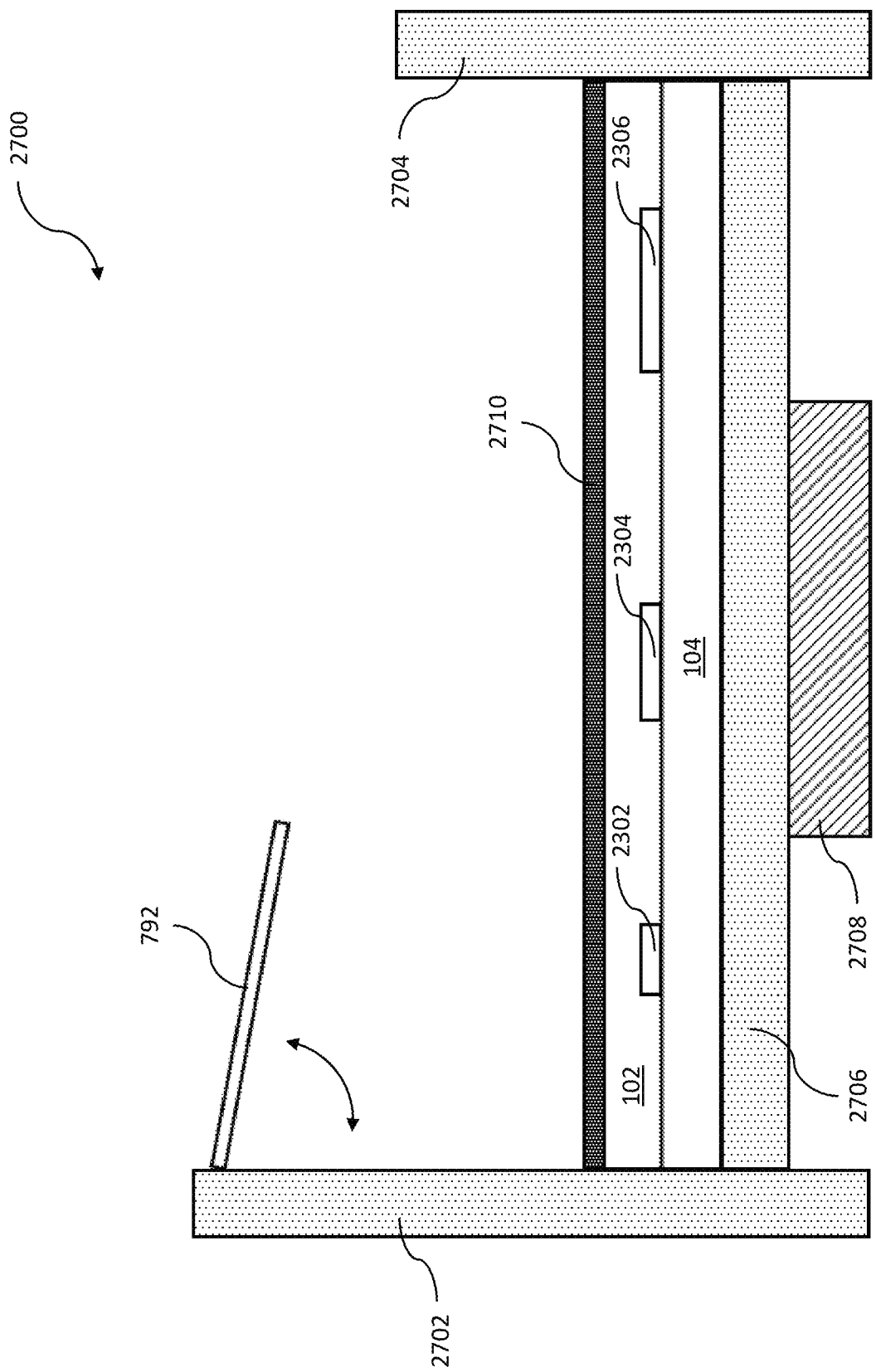
FIG. 27 illustrates one embodiment of an integrated bed system.

FIG. 27 illustrates one embodiment of an integrated bed system 2700. The integrated bed system 2700 includes a headboard 2702, a footboard 2704, and a bed frame 2706 to support a mattress 102 and a box springs or foundation 104. In one embodiment, the headboard 2702, the footboard 2704, and/or the bed frame 2706 include EMF shielding and/or positive ion shielding.

In a preferred embodiment, the headboard 2702 includes at least one red light and/or near-infrared lighting device 792. The at least one red light and/or near-infrared lighting device 792 preferably folds away from the headboard 2702 manually and/or automatically (e.g., on a timer). The at least one red light and/or near-infrared lighting device 792 includes at least one hinge, at least one spring, at least one piston, and/or at least one motor to reposition the at least one red light and/or near-infrared lighting device 792. Alternatively, the at least one red light and/or near-infrared lighting device 792 is permanently fixed to the headboard 2702 facing a sleeping surface. In one example, the at least one red light and/or near-infrared lighting device 792 is two red light and/or near-infrared lighting devices. Advantageously, this allows each user of a two-person bed to independently operate a red light and/or near-infrared lighting device 792. In another embodiment, the at least one red light and/or near-infrared lighting device 792 is positioned above the sleeping surface (e.g., on a ceiling). In one embodiment, the at least one red light and/or near-infrared lighting device 792 includes at least one fan. The at least one fan cools the user from heat generated by the at least one red light and/or near-infrared lighting device 792.

In a preferred embodiment, the mattress 102 includes a PEMF device 784 embedded in the mattress 102. In the example shown in FIG. 27, the PEMF device 784 has a first coil 2302 corresponding to a first region (e.g., head and neck), a second coil 2304 corresponding to a second region (e.g., torso and hips), and a third coil 2306 corresponding to a third region (e.g., legs and feet). In an alternative embodiment, the PEMF device 784 is embedded in the box springs or foundation 104. In yet another embodiment, the PEMF device 784 is placed under the box springs or foundation 104 (e.g., on the floor, between the box springs or foundation 104 and the bed frame 2706).

In the example shown in FIG. 27, the integrated bed system 2700 includes a combination mattress pad and red light and/or near-infrared lighting device 2710. The combination mattress pad and red light and/or near-infrared lighting device 2710 includes a mattress pad and a red light and/or near-infrared lighting device 792. Alternatively, the integrated bed system 2700 includes a mattress pad and/or a red light and/or near-infrared lighting device 792. In one embodiment, the mattress pad and/or the red light and/or near-infrared lighting device 792 are positioned on a sleep surface (e.g., mattress 102). In another embodiment, the mattress pad and/or the red light and/or near-infrared lighting device are embedded in the mattress 102.

A control box 2708 controls electronic components of the integrated bed system 2700. The control box 2708 preferably has at least one processor. By way of example, and not limitation, the processor may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information. In one embodiment, one or more of the at least one processor is operable to run predefined programs stored in at least one memory of the control box 2708.

The control box 2708 preferably includes at least one antenna, which allows the control box 2708 to receive and process input data (e.g., temperature settings, start and stop commands) from at least one remote device (e.g., smartphone, tablet, laptop computer, desktop computer, remote control). In a preferred embodiment, the at least one remote device is in wireless network communication with the control box 2708. The wireless communication is, by way of example and not limitation, radiofrequency, Bluetooth®, ZigBee®, Wi-Fi®, wireless local area networking, near field communication (NFC), or other similar commercially utilized standards. Alternatively, the at least one remote device is in wired communication with the control box 2708 through USB or equivalent.

In a preferred embodiment, the at least one remote device is operable to adjust settings (e.g., therapy on/off, temperature settings, PEMF settings) for the components of the integrated bed system 2700. The at least one remote device preferably has a user interface (e.g., a mobile application for a smartphone or tablet, buttons on a remote control) that allows a user to select target therapies using the integrated bed system 2700.

The control box 2708 may further include other features and electronics not shown. In one embodiment, the control box 2708 includes features of the control unit for the mattress pad (e.g., at least one fluid reservoir, at least one mechanism for forming structured water). In another embodiment, the control box 2708 includes a touch control and display board, overheat protectors, fluid level sensor, thermostat, additional case fans, and/or at least one speaker. The control box 2708 may also include an external power cord designed to plug into standard household electrical outlets, or may be powered using rechargeable or non-rechargeable batteries. In one embodiment, the touch control and display board includes a power button, temperature selection buttons (e.g., up arrow and down arrow), and/or an LCD to display the temperature. In another embodiment, the touch control and display board includes a program selection menu.

Figure 28:
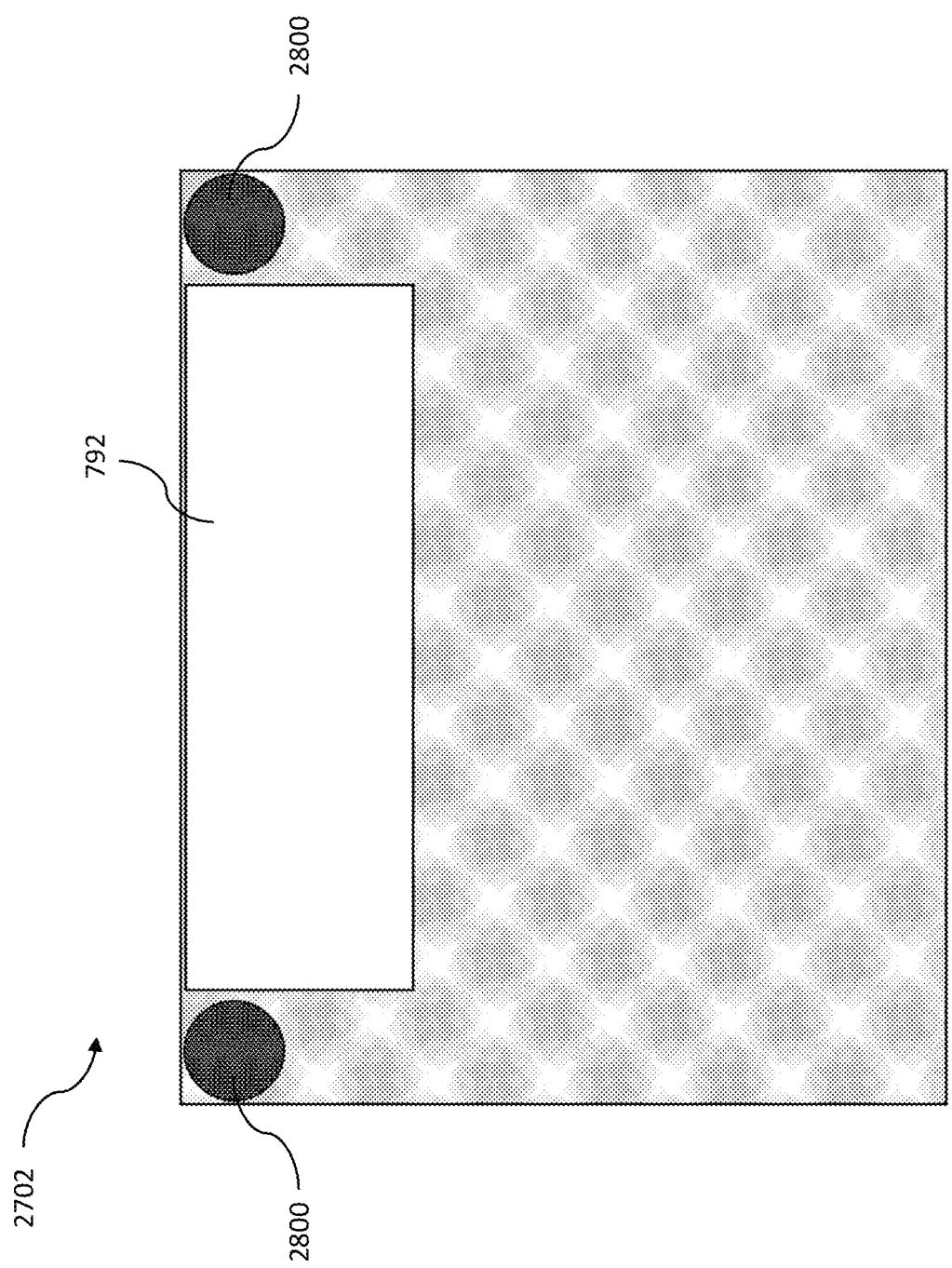
FIG. 28 illustrates one embodiment of a headboard of an integrated bed system.

FIG. 28 illustrates one embodiment of a headboard of an integrated bed system. The headboard 2702 includes a red light and/or near-infrared lighting device 792. The red light and/or near-infrared lighting device 792 In the example shown in FIG. 28, the headboard 2702 includes integrated speakers 2800 for the sound generator. The integrated speakers 2800 are also operable to function as an alarm clock to wake a user with sound.

Figure 29:
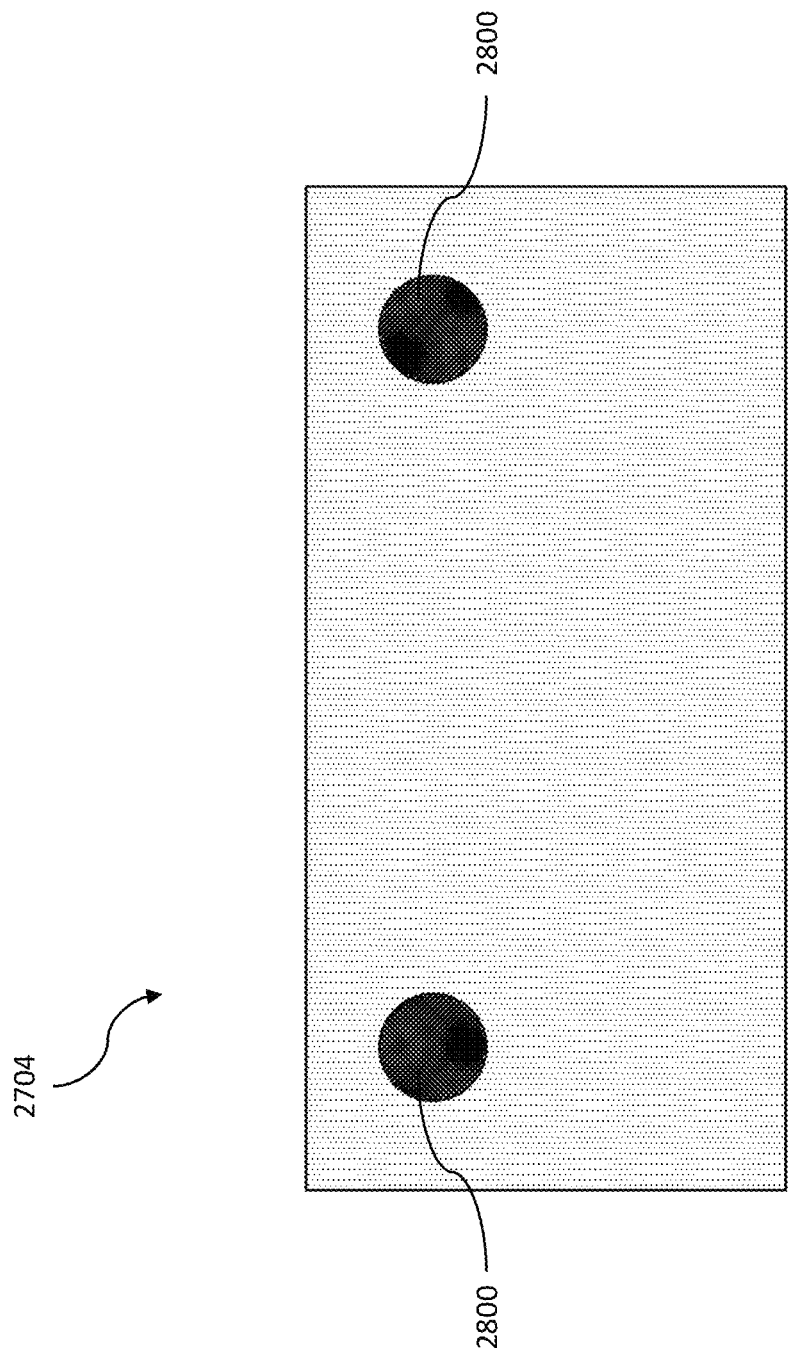
FIG. 29 illustrates one embodiment of a footboard of an integrated bed system.

FIG. 29 illustrates one embodiment of a footboard of an integrated bed system. In the example shown in FIG. 29, the footboard 2704 includes integrated speakers 2800 for the sound generator. The integrated speakers 2800 are also operable to function as an alarm clock to wake a user with sound.

Figure 30:
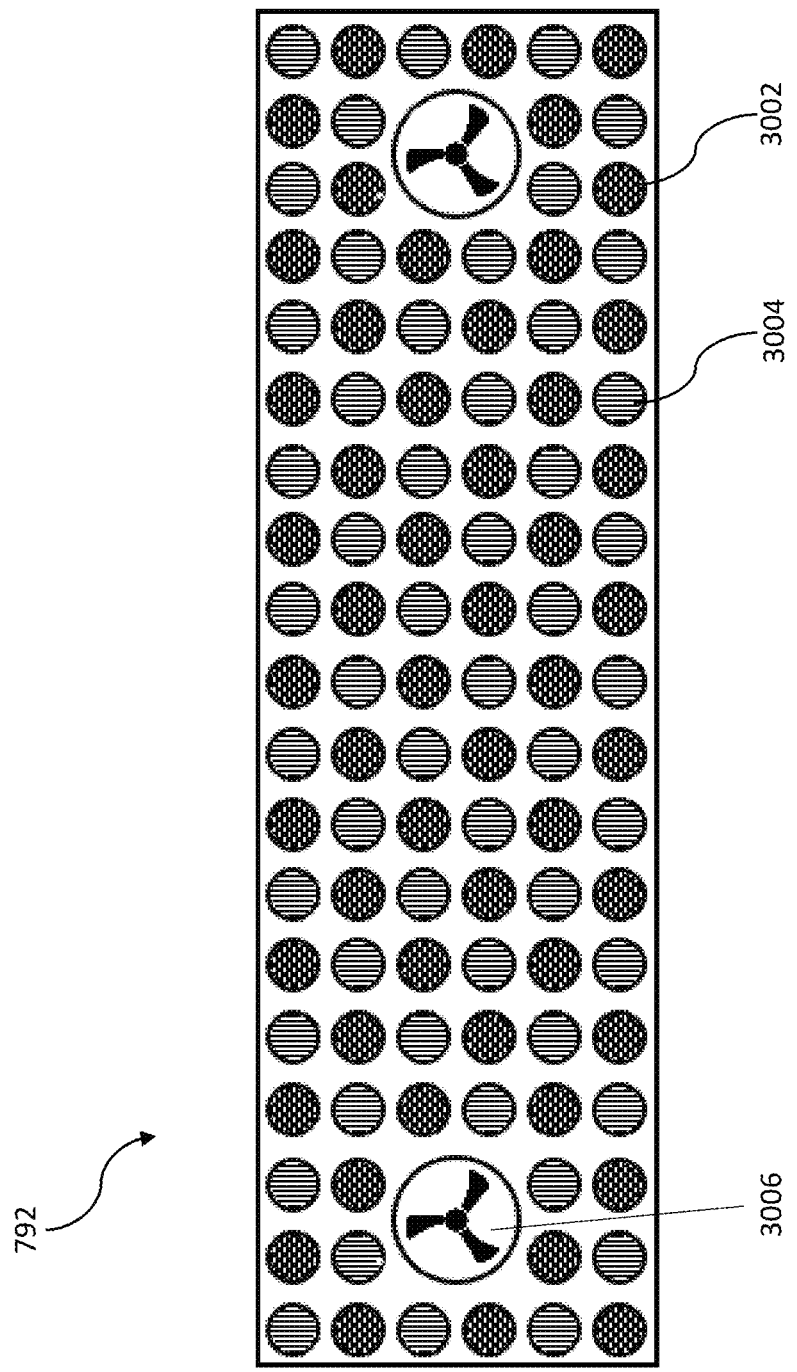
FIG. 30 illustrates one embodiment of a red light and/or near-infrared lighting device of an integrated bed system.

FIG. 30 illustrates one embodiment of a red light and/or near-infrared lighting device 792 of an integrated bed system. In the example shown in FIG. 30, the red light and/or near-infrared lighting device 792 includes at least one light emitting a first wavelength 3002 and at least one light emitting a second wavelength 3004. In one example, the at least one light emitting a first wavelength 3002 has a wavelength between about 660 nm and about 670 nm and the at least one light emitting a second wavelength 3004 has a wavelength between about 830 nm and about 850 nm. Although an equal number of the at least one light emitting a first wavelength 3002 and the at least one light emitting a second wavelength 3004 are shown in FIG. 30, alternative ratios are compatible with the present invention. Further, although a total of 106 lights are shown in FIG. 30, alternative numbers of lights are compatible with the present invention. In one embodiment, the red light and/or near-infrared lighting device 792 includes at least one fan 3006. The at least one fan 3006 cools the user from heat generated by the red light and/or near-infrared lighting device 792.

Figure 31:
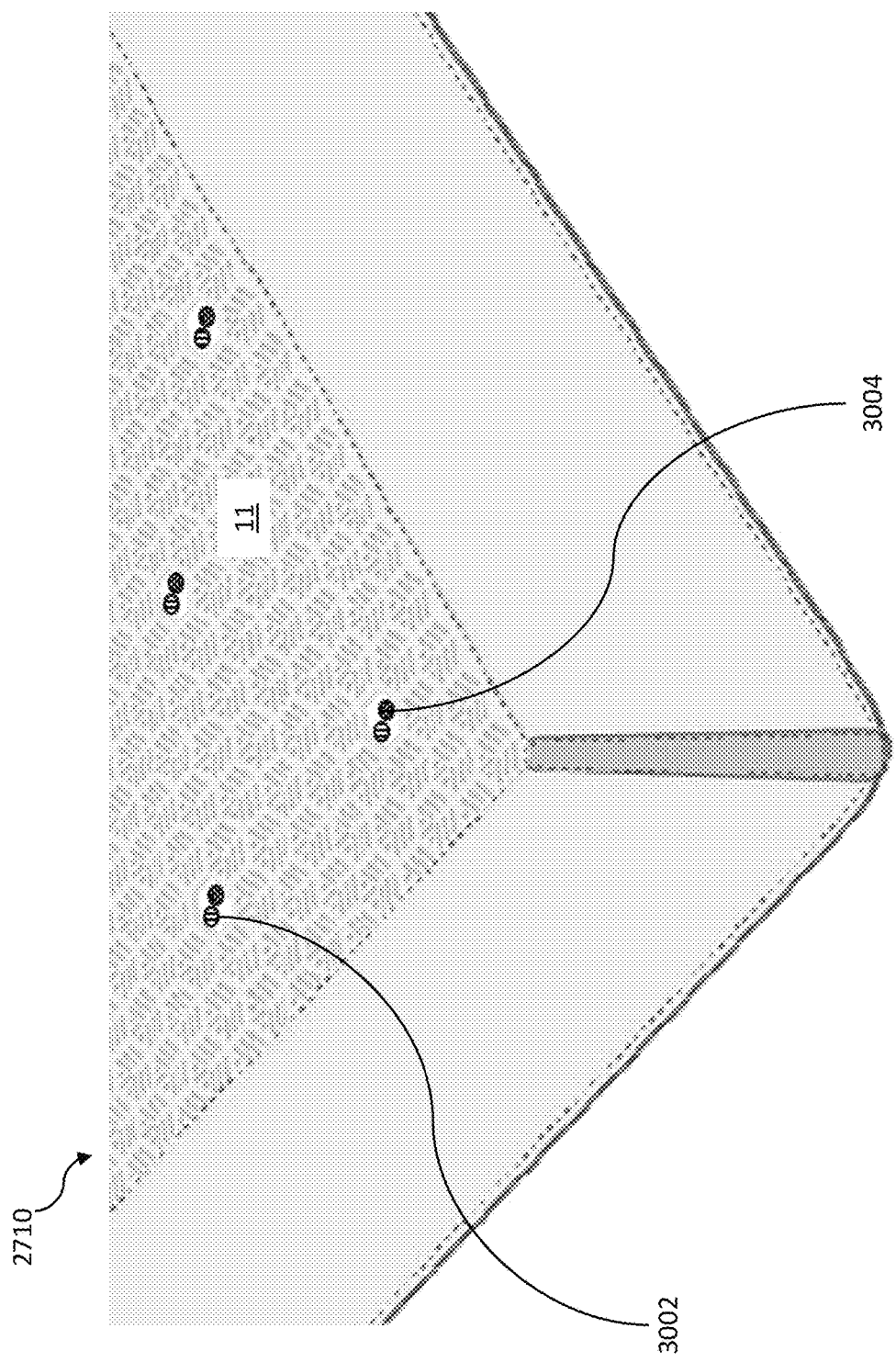
FIG. 31 illustrates one embodiment of a combination mattress pad and red light and/or near-infrared lighting device.

FIG. 31 illustrates one embodiment of a combination mattress pad and red light and/or near-infrared lighting device. The combination mattress pad and red light and/or near-infrared lighting device 2710 includes a mattress pad 11 and a red light and/or near-infrared lighting device. The red light and/or near-infrared lighting device includes at least one light emitting a first wavelength 3002 and at least one light emitting a second wavelength 3004. Advantageously, the combination mattress pad and red light and/or near-infrared lighting device 2710 cools the user from heat generated by the red light and/or near-infrared lighting device portion using the mattress pad 11 portion.

Figure 32:
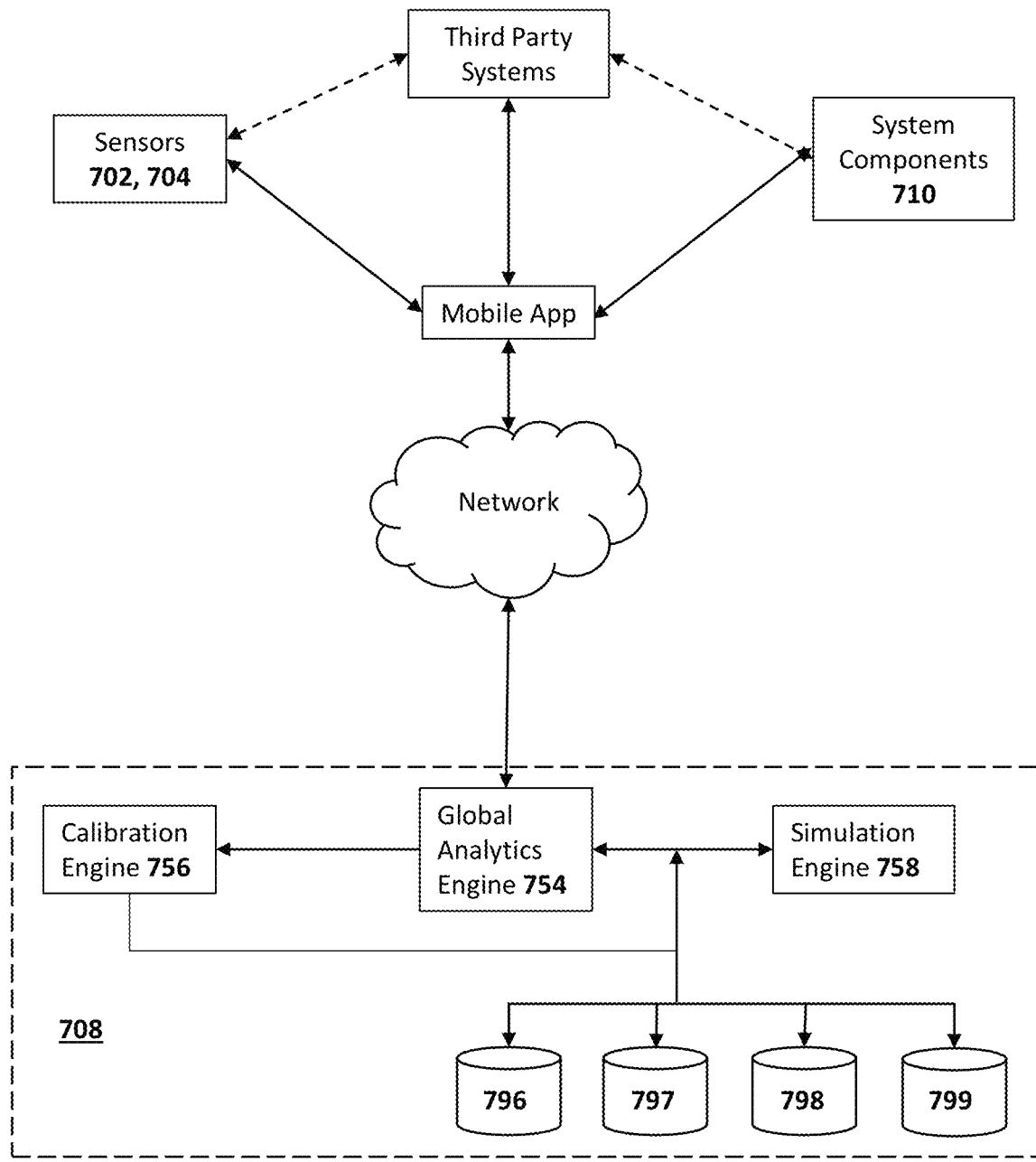
FIG. 32 is a block diagram of one embodiment of the system architecture.

FIG. 32 is a block diagram of one embodiment of the system architecture. The remote device has a mobile application, preferably on a smartphone, which is in wireless communication with body sensors 702 and/or environmental sensors 704. The mobile application is operable to communicate with third-party systems (e.g., Fitbit®, Jawbone®, Amazon® Alexa®, Apple® HomeKit™, Google® Home™, IF This Then That® (IFTTT®), Nest®) and the system components 710. The body sensors 702 and/or the environmental sensors 704 may communicate information to the mobile application through the third-party systems. The system components 710 may communicate information to the mobile application through the third-party systems. The mobile application communicates with the remote server 708 over the network.

At the start of a sleeping period, a program is selected that provides optimized values for the sleeping period. The program is preferably a predefined program or customized program based on user preferences. In one embodiment, the optimized values include, but are not limited to, sleep stage (e.g., awake, Stage N1, Stage N2, Stage N3, REM Sleep), breath rate, heart rate, brain waves (e.g., beta waves, alpha waves, theta waves, delta waves), blood oxygen rate, body temperature, and/or settings for the system components 710.

As shown in FIG. 32, in one embodiment, the remote server 708 hosts a global analytics engine 754, a calibration engine 756, a simulation engine 758, and databases 796, 797, 798, and 799. Although four databases are shown, it is equally possible to have any number of databases greater than one. The global analytics engine 754 generates predicted values for a monitored stress reduction and sleep promotion system using a virtual model of the stress reduction and sleep promotion system based on real-time data. The calibration engine 756 modifies and updates the virtual model based on the real-time data. Any operational parameter of the virtual model may be modified by the calibration engine 756 as long as the resulting modification is operable to be processed by the virtual model.

The global analytics engine 754 analyzes differences between the predicted values and optimized values. If the difference between the optimized values and the predicted values is greater than a threshold, then the simulation engine 758 determines optimized values of the monitored stress reduction and sleep promotion system based on the real-time data and user preferences. The global analytics engine 754 determines whether a change in parameters of the system components 710 is necessary to optimize sleep based on the output of the simulation engine 758. If a change in parameters is necessary, the new parameters are transmitted to the mobile application on the remote device and then to the system components 710. The calibration engine 756 then updates the virtual model with the new parameters. Thus, the system autonomously optimizes the stress reduction and sleep promotion system (e.g., surface temperature) without requiring input from a user.

Figure 33:
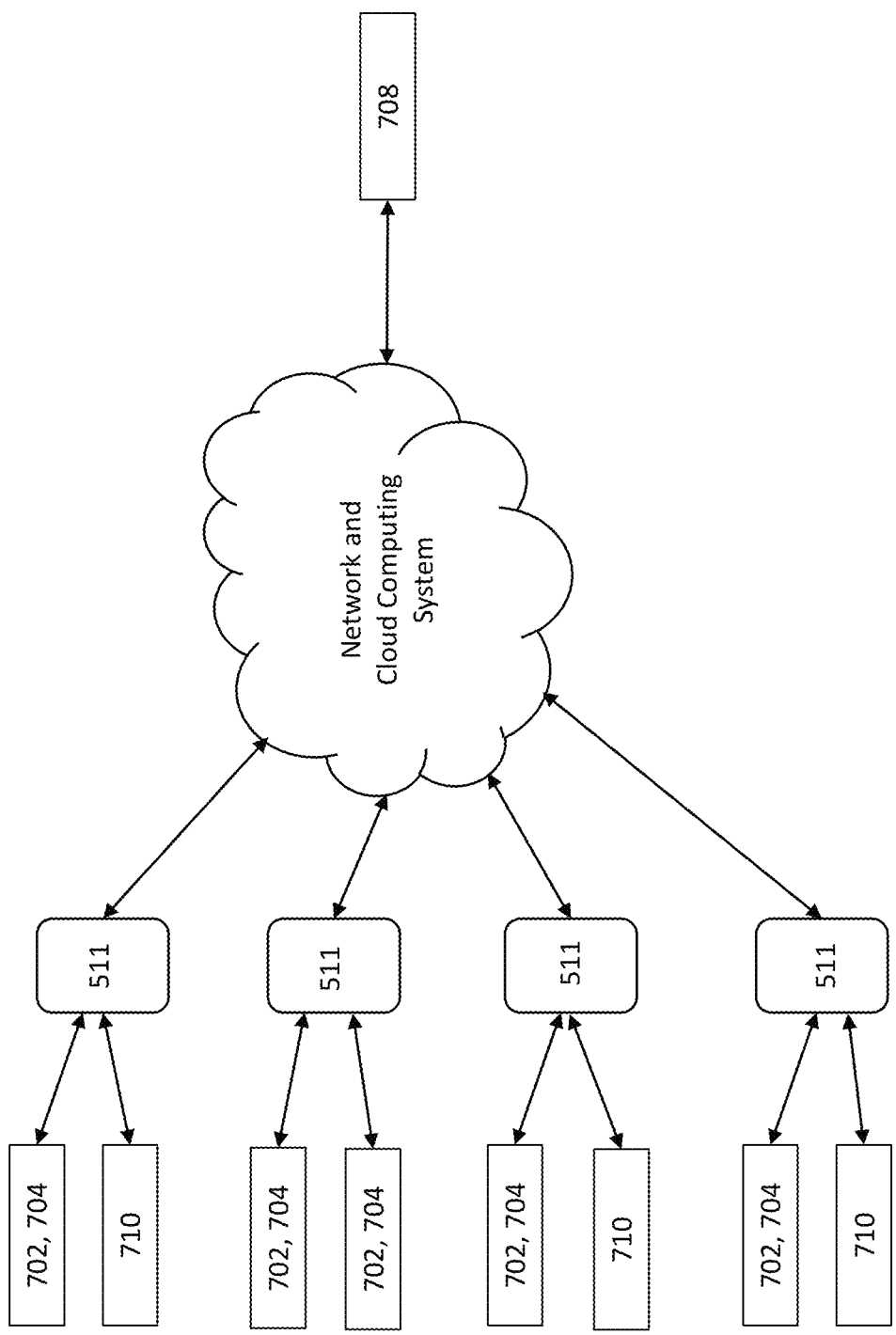
FIG. 33 is an illustration of a network of stress reduction and sleep promotion systems.

FIG. 33 is an illustration of a network of stress reduction and sleep promotion systems. Data from multiple users can be stored on a remote server 708. The remote server 708 is connected through a network and cloud computing system to a plurality of remote devices 511. Each of the plurality of remote devices 511 is connected to body sensors 702 and/or environmental sensors 704, as well as system components 710. Although one remote server is shown, it is equally possible to have any number of remote servers greater than one. A user may opt into sending their data to the remote server 708, which is stored in at least one database on the remote server 708. The simulation engine on the remote server 708 is operable to use data from the multiple users to determine customized and optimized sleep settings for the user based on personal preferences (e.g., a target number of hours of sleep, a preferred bed time, a preferred wake time, a faster time to fall asleep, fewer awakenings during the sleeping period, more REM sleep, more deep sleep, and/or a higher sleep efficiency) or physical condition (e.g., weight loss, comfort, athletic recovery, hot flashes, bed sores, depression). In one example, the temperature settings for a temperature-conditioned mattress pad for a user with hot flashes are automatically determined by the simulation engine examining data obtained from other users with hot flashes and a temperature-conditioned mattress pad stored in databases on the remote server.

The stress reduction and sleep promotion system includes a virtual model of the stress reduction and sleep promotion system. The virtual model is initialized based on the program selected. The virtual model of the stress reduction and sleep promotion system is dynamic, changing to reflect the status of the stress reduction and sleep promotion system in real time or near-real time. The virtual model includes information from the body sensors and the environmental sensors. Based on the data from the body sensors and the environmental sensors, the virtual model generates predicted values for the stress reduction and sleep promotion system. A sleep stage (e.g., awake, Stage N1, Stage N2, Stage N3, REM sleep) for the user is determined from the data from the body sensors.

The stress reduction and sleep promotion system is monitored to determine if there is a change in status of the body sensors (e.g., change in body temperature), the environmental sensors (e.g., change in room temperature), the system components (e.g., change in temperature of mattress pad), or sleep stage of the user. If there is a change in status, the virtual model is updated to reflect the change in status. Predicted values are generated for the stress reduction and sleep promotion system. If a difference between the optimized values and the predicted values is greater than a threshold, a simulation is run on the simulation engine to optimize the stress reduction and sleep promotion system based on the real-time data. The simulation engine uses information including, but not limited to, global historical subjective data, global historical objective data, global historical environmental data, and/or global profile data to determine if a change in parameters is necessary to optimize the stress reduction and sleep promotion system. In one example, the temperature of the mattress pad is lowered to keep a user in Stage N3 sleep for a longer period of time.

Figure 34:
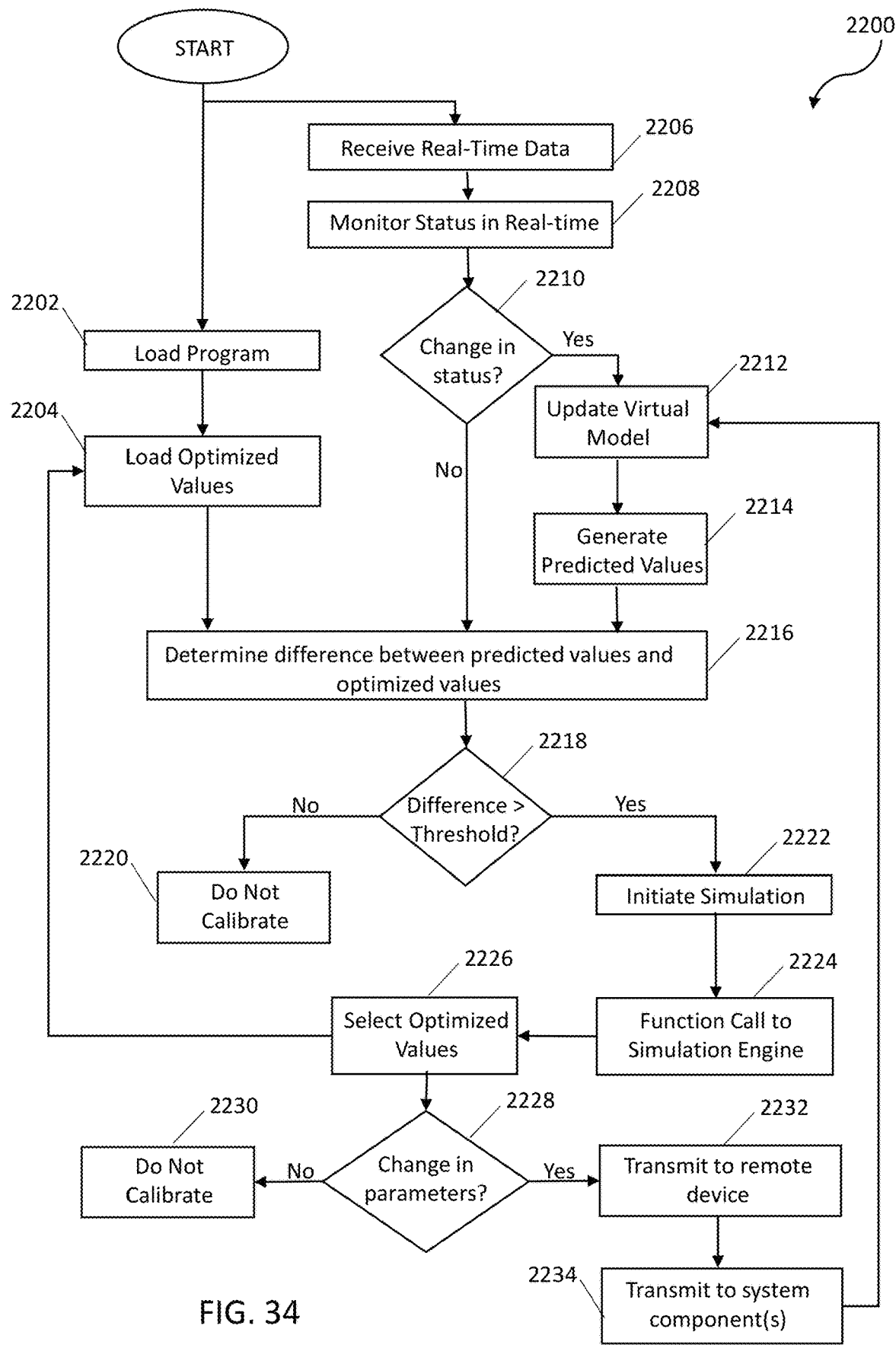
FIG. 34 is a diagram illustrating an example process for monitoring a stress reduction and sleep promotion system and updating a virtual model based on monitored data.

FIG. 34 is a diagram illustrating an example process for monitoring a stress reduction and sleep promotion system and updating a virtual model based on monitored data. First, in step 2202, a program to control the stress reduction and sleep promotion system is loaded onto a remote device. In a preferred embodiment, the program is a predefined program or customized program based on user preferences. Optimized values including, but not limited to, the sleep status, parameters for system components, and/or times for changes, from the program are loaded onto the global analytics engine in step 2204. Real-time data is received by the remote server via the remote device in step 2206. The real-time data is used to monitor the status of the stress reduction and sleep promotion system in step 2208. As described above, the stress reduction and sleep promotion system includes body sensors, environmental sensors, a remote device with local storage, a remote server, and system components. Accordingly, the status of the body sensors, the environmental sensors, and the system components are monitored in step 2208, as well as the sleep status of a user. In step 2210, a determination is made regarding whether there is a change in the status of the monitored devices and/or the sleep state. If there is a change, then the virtual model is updated in step 2212 by the calibration engine to reflect the status change, i.e., the corresponding virtual components data is updated to reflect the actual status of the various monitored devices.

In step 2214, predicted values for the monitored stress reduction and sleep promotion system are generated based on the current, real-time status of the monitored system. In one embodiment, the predicted values include, but are not limited to, sleep stage (e.g., awake, Stage N1, Stage N2, Stage N3, REM Sleep). In step 2216, the optimized values loaded in step 2204 are compared with the predicted values obtained in step 2214.

Accordingly, meaningful predicted values based on the actual condition of monitored stress reduction and sleep promotion system are generated in step 2214. These predicted values are then used to determine if further action should be taken based on the results of the comparison in step 2216. For example, if it is determined in step 2218 that the difference between the predicted values and the optimized values is less than or equal to a threshold, then a do not calibrate instruction is issued in step 2220. If the difference between the real-time data and the predicted values is greater than the threshold, as determined in step 2218, then an initiate simulation command is generated in step 2222.

In step 2224, a function call to the simulation engine is generated in response to the initiate simulation command. The simulation engine selects optimized values for the stress reduction and sleep promotion system in step 2226. These optimized values are updated on the global analytics engine in step 2204. Based on the output of the simulation engine, the global analytics engine determines if the optimized values require a change in parameters of the stress reduction and sleep promotion system (e.g., temperature of mattress pad, room temperature, lighting, mattress firmness, mattress elevation) in step 2228. In a preferred embodiment, the simulation engine uses the global historical subjective data, the global historical objective data, the global historical environmental data, and the global profile data to determine if the change in parameters is necessary. If a change in parameters is not necessary, a do not calibrate instruction is issued in step 2230. If a change in parameters is necessary, the new parameters are transmitted to the remote device in step 2232. The remote device transmits the new parameters to the system components in step 2234.

The calibration engine updates the virtual model in step 2212 based on the real-time data and the new parameters. Predicted values are then generated in step 2214. In this manner, the predicted values generated in step 2214 are not only updated to reflect the actual status of monitored stress reduction and sleep promotion system, but they are also updated to reflect natural changes in monitored system as the user moves through the sleep cycle. Accordingly, realistic predicted values can be generated in step 2214.

As previously mentioned, the least one remote device preferably has a user interface (e.g., a mobile application for a smartphone or tablet) that allows the stress reduction and sleep promotion system to adjust the parameters of the stress reduction and sleep promotion system. The parameters of the stress reduction and sleep promotion system (e.g., target temperatures of a mattress pad) can be manipulated through the sleeping period using a predefined program or a customized program based on user preferences to produce a deeper, more restful sleep.

Because the target temperatures may be set at any time, those target temperatures may be manipulated through the sleeping period in order to match user preferences or a program to correlate with user sleep cycles to produce a deeper, more restful sleep.

In one embodiment, the mobile application measures a time when a user began attempting to sleep (TATS), a TATS start time, a TATS end time, a time in bed (TIB), a TIB start time, and/or a TIB end time. The mobile application calculates a total TATS duration based on the TATS start time and the TATS end time. The mobile application also calculates a total TIB duration based on the TIB start time and the TIB end time. In one embodiment, the TATS start time, the TATS end time, the TIB start time, and/or the TIB end time are indicated by the user (e.g., by pressing a button in the mobile application). Alternatively, the TATS start time, the TATS end time, the TIB start time, and/or the TIB end time are determined by sensors. In one example, the TATS start time is determined by a user's eyes closing while in bed. In another example, the TATS end time is determined by increased motion as measured by a movement sensor and/or opening of the eyes. In yet another example, the TIB start time is determined by sensors indicating a user is horizontal and/or bed or room sensors indicating the user is in bed. In still another example, the TIB end time is determined by sensors indicating a user is not horizontal and/or bed or room sensors indicating the user is not in bed.

The mobile application is operable to determine whether a user is awake or asleep. The state of wakefulness (i.e., "awake") is characterized by cognitive awareness and/or consciousness, responsiveness to environmental cues, sustained movement detected by a movement sensor, beta and/or alpha waves as detected by EEG, increased heart rate, increased respiration, increased blood pressure, increased electrodermal activity, increased body temperature, open eyes, voluntary eye movements, and/or increased EMG on the chin. The state of sleep (i.e., "asleep") is characterized by loss of alertness and/or consciousness, lack of response to environmental cues, lack of movement, reduction in alpha waves as detected by EEG, increased theta and delta waves as detected by EEG, decreased heart rate, decreased respiration, decreased blood pressure, decreased body temperature, closed eyes, eye twitches, and/or decreased oxygen saturation.

In a preferred embodiment, the mobile application is operable to measure an initial sleep onset time and/or a final awakening time. The initial sleep onset time is a first occurrence of sleep after the TATS start time. The final awakening time is a time immediately after the last occurrence of sleep before the TATS end time. In one embodiment, the mobile application calculates a latency to sleep onset as the duration of a time interval between the TATS start time to the initial sleep onset time. In another embodiment, the mobile application calculates a latency to arising as the duration of a time interval between the final awakening time to the TATS end time. In a preferred embodiment, the mobile application is operable to calculate a sleep efficiency percentage. In one embodiment, the sleep efficiency percentage is defined as the total sleep time divided by the total TATS duration. In an alternative embodiment, the sleep efficiency percentage is defined as the total sleep time divided by the total TIB duration.

In one embodiment, the mobile application is operable to determine a total sleep period duration, a total sleep time, a sleep maintenance percentage, a total wakefulness duration, a wakefulness duration after initial sleep onset, a total number of awakenings, an awakening rate per hour, and/or a sleep fragmentation rate.

In another embodiment, the mobile application is operable to determine REM sleep, N1 sleep, N2 sleep, and/or N3 sleep. REM sleep is characterized by low-voltage, mixed-frequency EEG activity with less than 15 seconds of alpha activity, saw-tooth theta EEG activity, rapid eye movements, and/or decreased or absent EMG activity on the chin. N1 sleep is characterized by low-voltage, mixed-frequency EEG activity with less than 15 seconds of alpha activity in a 30-second epoch, no sleep spindles or K complexes, possible slow rolling eye movements, and/or diminished EMG activity on the chin. N2 sleep is characterized by sleep spindle and/or K complex activity, absence of eye movements, and/or diminished EMG activity on the chin. N3 sleep is characterized by high amplitude (e.g., greater than 750/peak-to-peak), slow wave (e.g., frequency of 4 Hz or less) EEG activity. In yet another embodiment, the mobile application is operable to calculate REM sleep duration, percentage, and latency from sleep onset; N1 sleep duration, percentage, and latency from sleep onset; N2 sleep duration, percentage, and latency from sleep onset; and/or N3 sleep duration, percentage, and latency from sleep onset.

Alternatively, the calculations and determining of sleep states described above are determined over the network on a remote server. In one embodiment, the calculations and determining of sleep states are then transmitted to at least one remote device.

Figure 35:
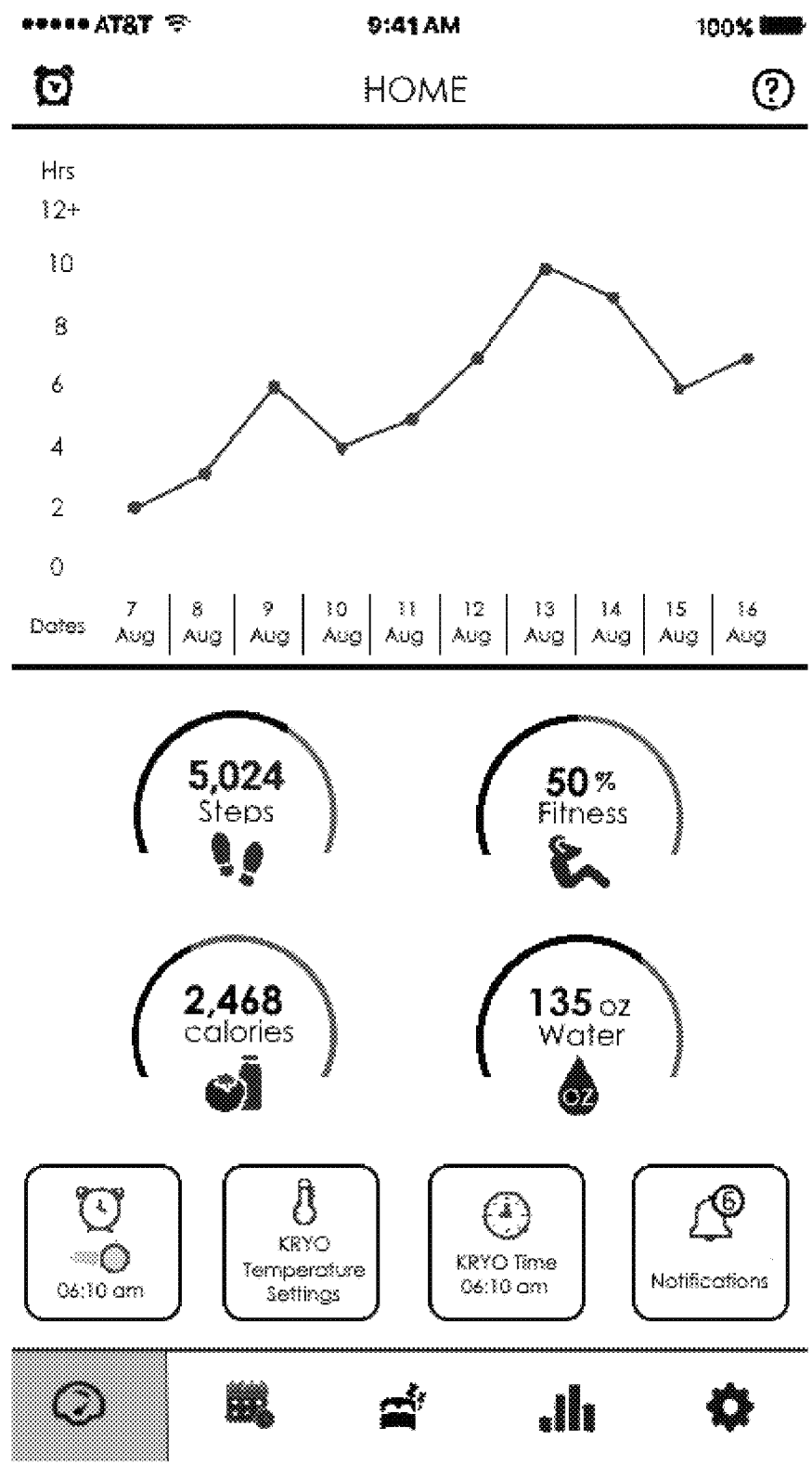
FIG. 35 illustrates a home screen of one embodiment of a graphical user interface (GUI) for a mobile application.

FIG. 35 illustrates a home screen of one embodiment of a graphical user interface (GUI) for a mobile application. A bottom navigation bar allows a user to rapidly switch between destinations within the mobile application. In FIG. 35, the bottom navigation bar includes (in order from left to right) icons for the home screen, a schedule screen, a sleep screen, a progress screen, and a goal settings screen.

The home screen includes a graph of the number of hours a user slept versus dates. In this example, the graph provides the number of hours a user slept for the previous 10 days. In one embodiment, the number of hours a user slept for a day is obtained from a wearable device (e.g., Fitbit®, Jawbone® UP, Misfit™, Apple Watch®, Nokia® Steel, Nokia® Go). Alternatively, the user manually enters a time the user went to sleep and a time the user woke up.

The home screen also provides a current snapshot of the user's daily health information. The user's daily health information includes, but is not limited to, the number of steps the user has taken, the percentage of fitness goals achieved, the number of calories consumed by the user, and the amount of water consumed by the user. This information is preferably updated in real time or near-real time by the mobile application. In one embodiment, this information is manually entered into the mobile application. Alternatively, this information is obtained from third-party applications (e.g., Fitbit®, Jawbone®, Misfit™, MyFitnessPal®, Apple® Health, Nokia® Health Mate).

The home screen allows the user to set a smart alarm (e.g., 6:10 AM). The smart alarm increases the surface temperature of the mattress pad sufficiently over a period of time to allow the user to emerge out of the last sleep cycle. The speed of awakening is based on the sleep cycle information. The speed of temperature increase is faster (e.g., 0.278° C./minute (0.5° F./minute)) if a new cycle is just beginning. The speed of temperature increase is slower (e.g., 0.056° C./minute (0.1° F./minute)) if the user is just coming out of the bottom of a sleep cycle. In one embodiment, the mobile application uses active data collection of the user's vital signs, including, but not limited to, heart rate, breath rate, blood oxygen level, brain waves, and/or skin temperature, to determine the speed of awakening.

Figure 36:
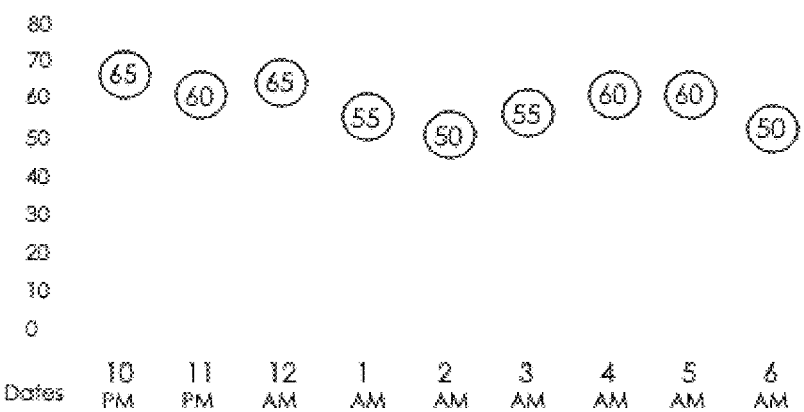
FIG. 36 illustrates a schedule screen of one embodiment of a GUI for a mobile application.

FIG. 36 illustrates a schedule screen of one embodiment of a GUI for a mobile application. The mobile application allows a user to select a temperature schedule. In FIG. 36, the temperature varies between 10-18.33° C. (50-65° F.) between 10 PM and 6 AM. The schedule screen displays a graph of temperature versus time.

Figure 37:
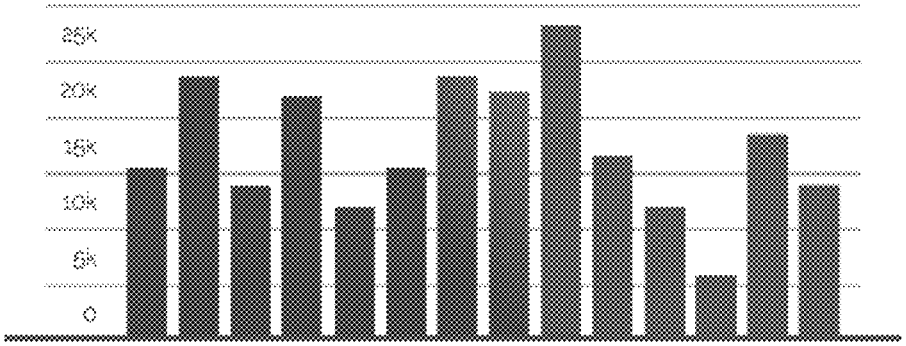
FIG. 37 illustrates another schedule screen of one embodiment of a GUI for a mobile application.

FIG. 37 illustrates another schedule screen of one embodiment of a GUI for a mobile application. The mobile application allows a user to select a sleep time and a wake time.

Figure 38:
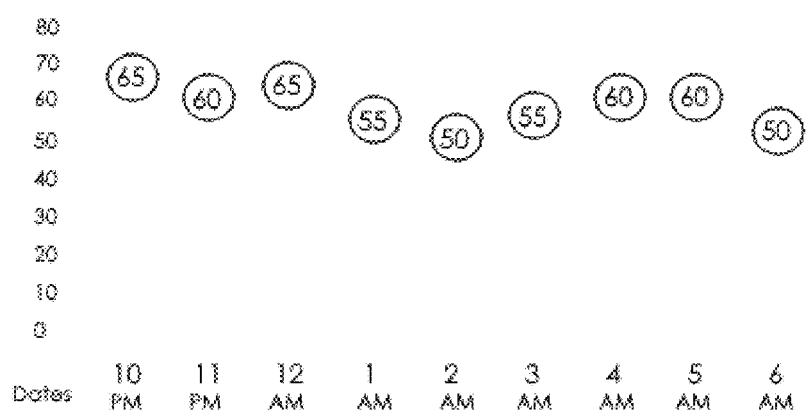
FIG. 38 illustrates a sleep screen of one embodiment of a GUI for a mobile application.

FIG. 38 illustrates a sleep screen of one embodiment of a GUI for a mobile application. The sleep screen displays a graph of time versus temperature for the previous day. The sleep screen displays a starting temperature and a wake time for the sleeping period. The user can select a "start sleep" button to manually track sleep cycles.

The sleep screen also has a button for a smart alarm. This allows the mobile application to adjust the settings of the mattress pad to wake the user at an optimal time within a sleep cycle. As previously described, gently awakening the user by increasing the temperature prevents sleep inertia. The sleep screen also has a button for tracking motion of the user. Further, the sleep screen also has a button for tracking sound of the user.

Figure 39:
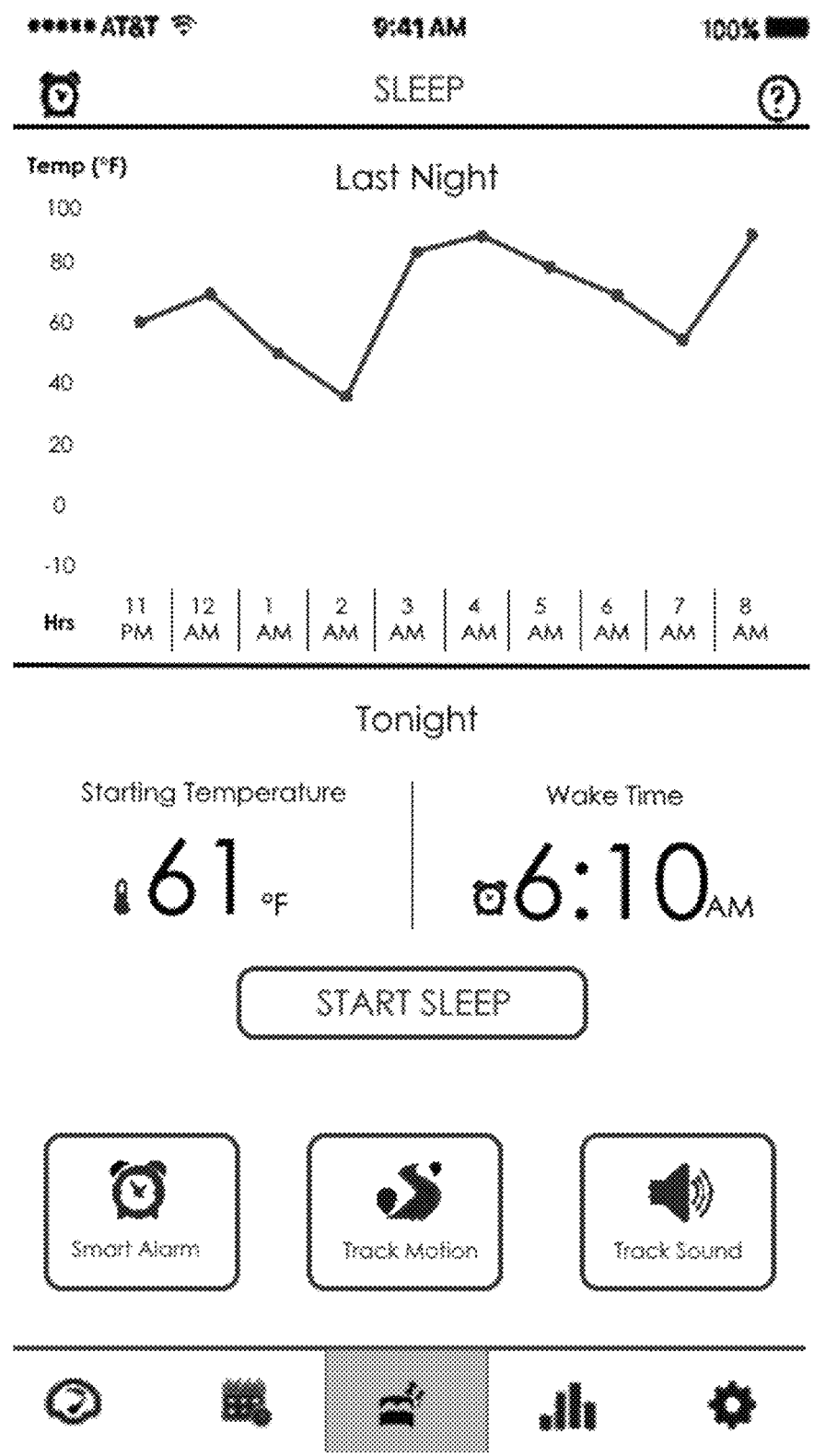
FIG. 39 illustrates a goal settings screen for one embodiment of a GUI for a mobile application.

FIG. 39 illustrates a goal settings screen for one embodiment of a GUI for a mobile application. The goal settings screen allows a user to turn a bed time reminder on or off and select a target number of hours of sleep (e.g., 8 hours). The goal settings screen also allows a user to select a preferred sleep time (e.g., 10:00 PM) and a preferred wake time (e.g., 6:00 AM). The goal settings screen also allows a user to set a goal weight, goal amount of water to consume, and goal number of calories to consume. Additional goals include, but are not limited to, a faster time to fall asleep, fewer awakenings during the sleeping period, more REM sleep, more deep sleep (e.g., N3 sleep), and/or a higher sleep efficiency.

Figure 40:
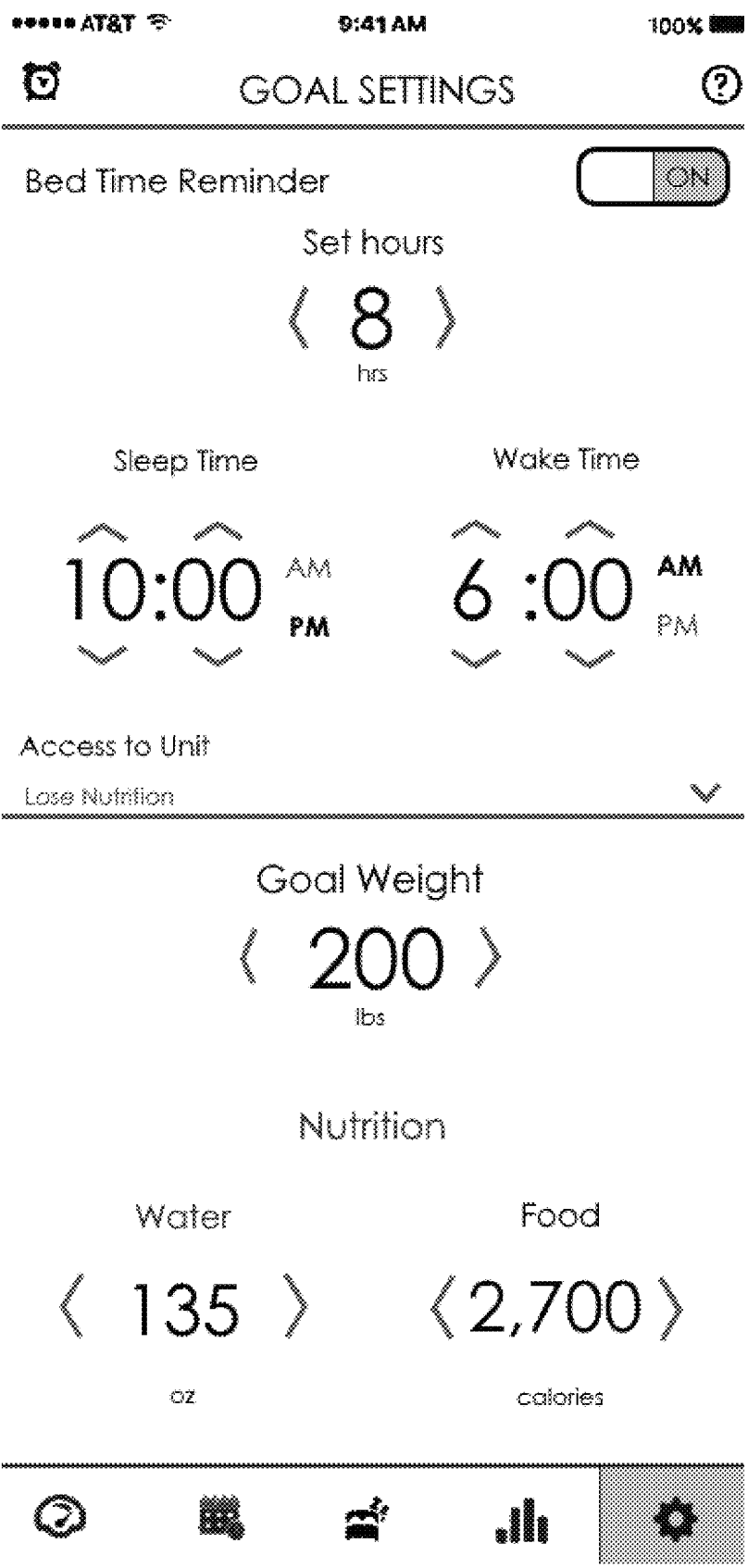
FIG. 40 illustrates a progress screen for one embodiment of a GUI for a mobile application.

FIG. 40 illustrates a progress screen for one embodiment of a GUI for a mobile application. The progress screen includes a graph of the number of hours a user slept versus dates. In this example, the graph provides the number of hours a user slept for the previous 10 days. The progress screen displays a current sleep efficiency (e.g., 80%). The progress screen lists the current date, a sleep time, a wake time, and number of hours of sleep. A "log manually" button allows the user to manually log sleep. The progress screen also includes a graph of the depth of sleep (e.g., light or deep) versus dates. In this example, the graph provides the depth of sleep for the previous 10 days. The progress screen displays a time spent in deep sleep (e.g., 5.30 hrs) and a time spent in light sleep (e.g., 3.15 hrs).

Figure 41:
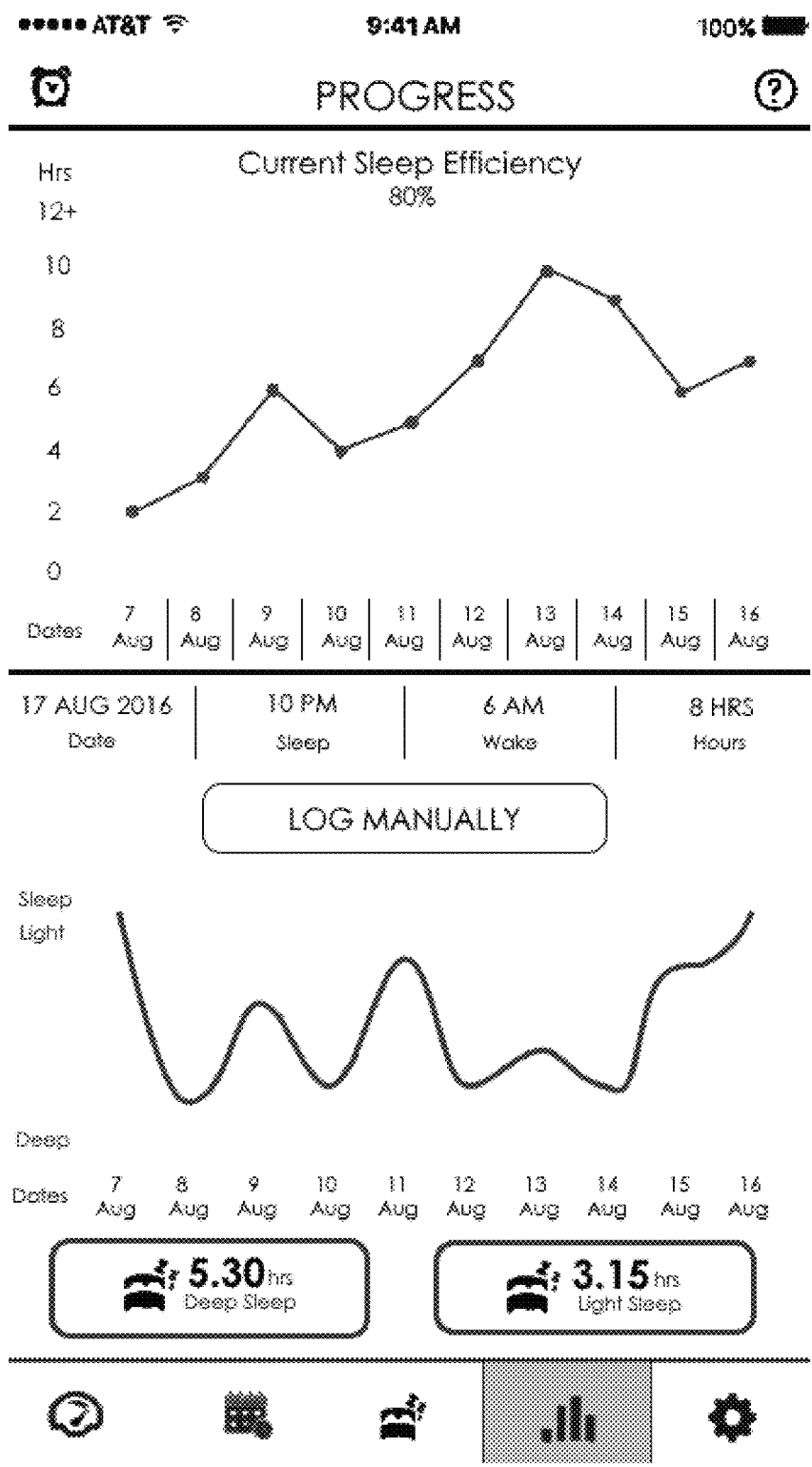
FIG. 41 illustrates a profile screen for one embodiment of a GUI for a mobile application.

FIG. 41 illustrates a profile screen for one embodiment of a GUI for a mobile application. In this embodiment, the mobile application includes a social component. The mobile application allows users to upload photos. The mobile application also allows users to follow other users. In this example, the user has 863 followers. A notification illustrates that the user has 4 new followers. Additionally, the mobile application allows users to like status updates and photos of other users. In this example, the user has posted 2471 photos and has 1593 likes. A notification illustrates that the user has 7 new likes. Further, the GUI displays statistics for the number of likes, followers, and photos over several months.

Figure 42:
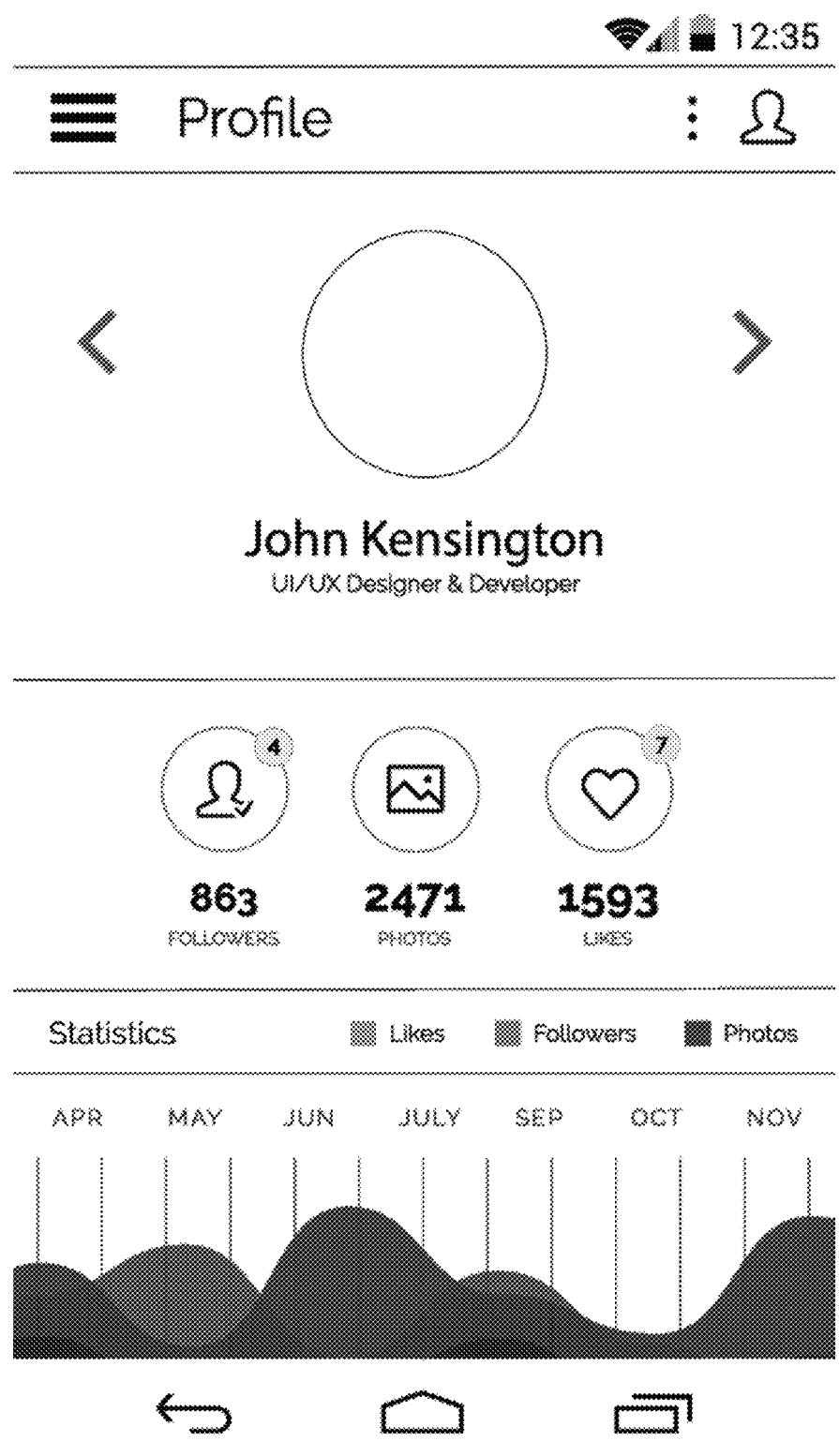
FIG. 42 illustrates another profile screen for one embodiment of a GUI for a mobile application.

FIG. 42 illustrates another profile screen for one embodiment of a GUI for a mobile application. In this example, the mobile application is operable to send messages between users.

Figure 43:
FIG. 43 illustrates yet another profile screen for one embodiment of a GUI for a mobile application.

FIG. 43 illustrates yet another profile screen for one embodiment of a GUI for a mobile application. In this example, the profile screen displays a weekday sleep time of 10 PM and a weekday wake up time of 6 AM. The profile screen also displays a weekend sleep time of 10 PM and a weekend wake up time of 6 AM. The profile screen includes a button to add sleep profile. A bottom navigation bar allows a user to rapidly switch between destinations within the mobile application. In FIG. 43, the bottom navigation bar includes (in order from left to right) icons for a temperature screen, a sleep screen, an alarm screen, a notification screen, and a settings screen.

Figure 44:
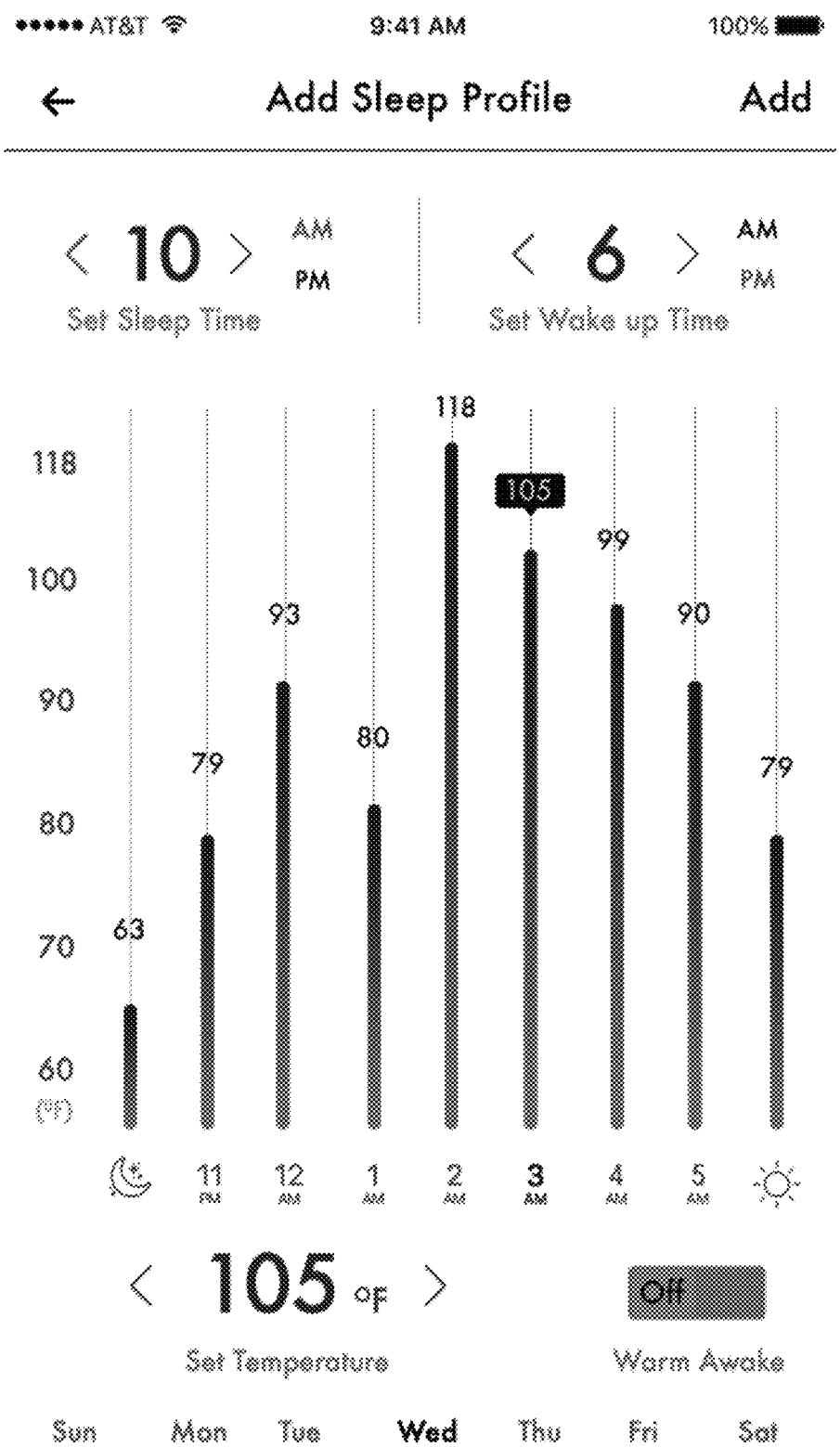
FIG. 44 illustrates an add sleep profile screen for one embodiment of a GUI for a mobile application.

FIG. 44 illustrates an add sleep profile screen for one embodiment of a GUI for a mobile application. The mobile application is operable to allow the user to set a sleep time and a wake up time. Further, the mobile application is operable to allow a user to select temperatures for a mattress pad over a sleep period. In this example, the temperature is set at 17.22° C. (63° F.) at 10 PM, 26.11° C. (79° F.) at 11 PM, 33.89° C. (93° F.) at 12 AM, 26.67° C. (80° F.) at 1 AM, 47.78° C. (118° F.) at 2 AM, 40.56° C. (105° F.) at 3 AM, 37.22° C. (99° F.) at 4 AM, 32.22° C. (90° F.) at 5 AM, and 26.11° C. (79° F.) at 6 AM. Further, the mobile application allows the user to select warm awake, which slowly (e.g., 0.278° C./minute (0.5° F./minute)) warms the user to awaken the user.

Figure 45:
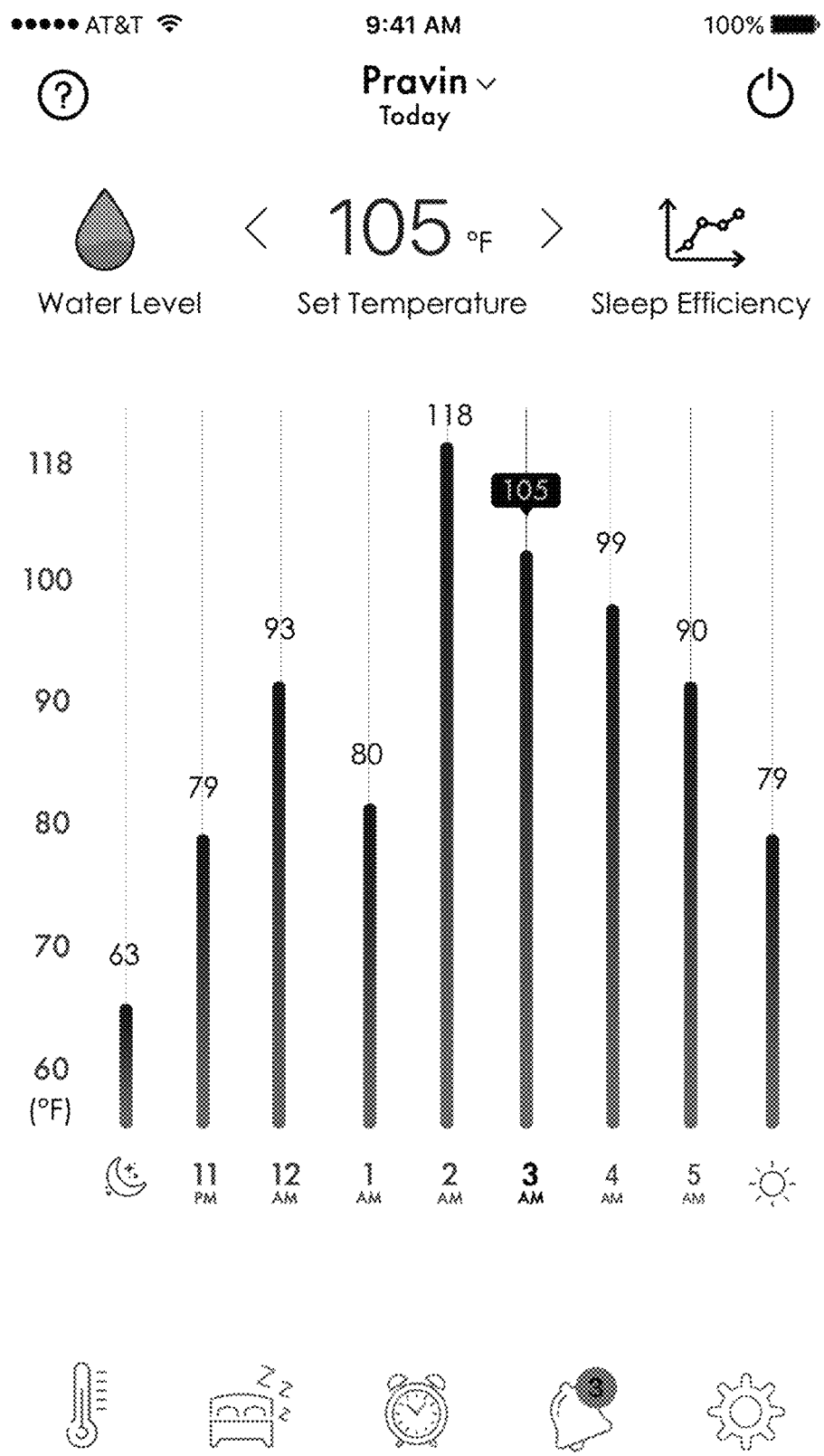
FIG. 45 illustrates a dashboard screen for one embodiment of a GUI for a mobile application.

FIG. 45 illustrates a dashboard screen for one embodiment of a GUI for a mobile application. In this embodiment, the mobile application is operable to allow the user to check the water level of the at least one reservoir in the control unit. In a preferred embodiment, the mobile application notifies the user when the water level is below a threshold. Further, the mobile application allows the user to display sleep efficiency.

In another embodiment, the mobile application notifies the user that water treatment or purification is required. In another embodiment, the mobile application automatically schedules water treatment or purification (e.g., automatically turning on the UV light for water treatment) at designated time intervals.

Most individuals adopt a monophasic sleep pattern (e.g., sleeping 6-8 hours at a time). Non-monophasic sleep occurs when an individual adopts a biphasic or polyphasic sleep pattern. A biphasic sleep pattern is when the individual sleeps twice per day. Typically, this consists of a shorter rest (e.g., "siesta") during the day and a longer sleep period during the night. A polyphasic sleep pattern (e.g., Everyman, Uberman, Dymaxion, Dual Core) consists of multiple sleeps throughout the day, generally ranging from 4 to 6 periods of sleep per day.

FIG. 46 illustrates a profile screen for one embodiment of a GUI for a mobile application allowing for biphasic sleep. In this example, the user sleeps from 1 PM to 3 PM and 11 PM to 5 AM on weekdays. The user also sleeps from 1 PM to 3 PM and 2 AM to 9 AM on weekends.

Although FIGS. 43 and 46 show weekday and weekend sleep schedules, the mobile application is operable to allow users to set specific sleep schedules for each day of the week. In one example, the mobile application allows the user to set different sleep schedules for Monday through Thursday (e.g., work days of a compressed work week), Friday, Saturday, and Sunday.

In a preferred embodiment, the mobile application is operable to provide reminders to the user. In one example, the mobile application reminds the user to get additional sleep (e.g., due to physical activity). In another example, the mobile application alerts the user to go to sleep. In one embodiment, the mobile application is operable to provide suggestions for treatments based on the user profile. In one example, the mobile application provides a guided meditation to relieve stress. In another example, the mobile application suggests a treatment with a TENS device to relieve pain.

In another embodiment, the mobile application is operable to analyze trends over time. In one example, the mobile application determines that the user's heart rate has increased by 15 beats per minute over a time period of a year. The mobile application suggests that the user contact a health care provider because this may be a symptom of heart disease. In another example, the mobile application determines that the user's blood oxygen level as measured by a pulse oximeter decreases at night. The mobile application suggests that the user contact a health care provider because this may be a symptom of sleep apnea.

The mobile application preferably allows the user to download their information (e.g., in a comma-separated value (CSV) file). Additionally or alternatively, the mobile application allows the user to share their information with a health care provider and/or a caregiver.

Figure 47:
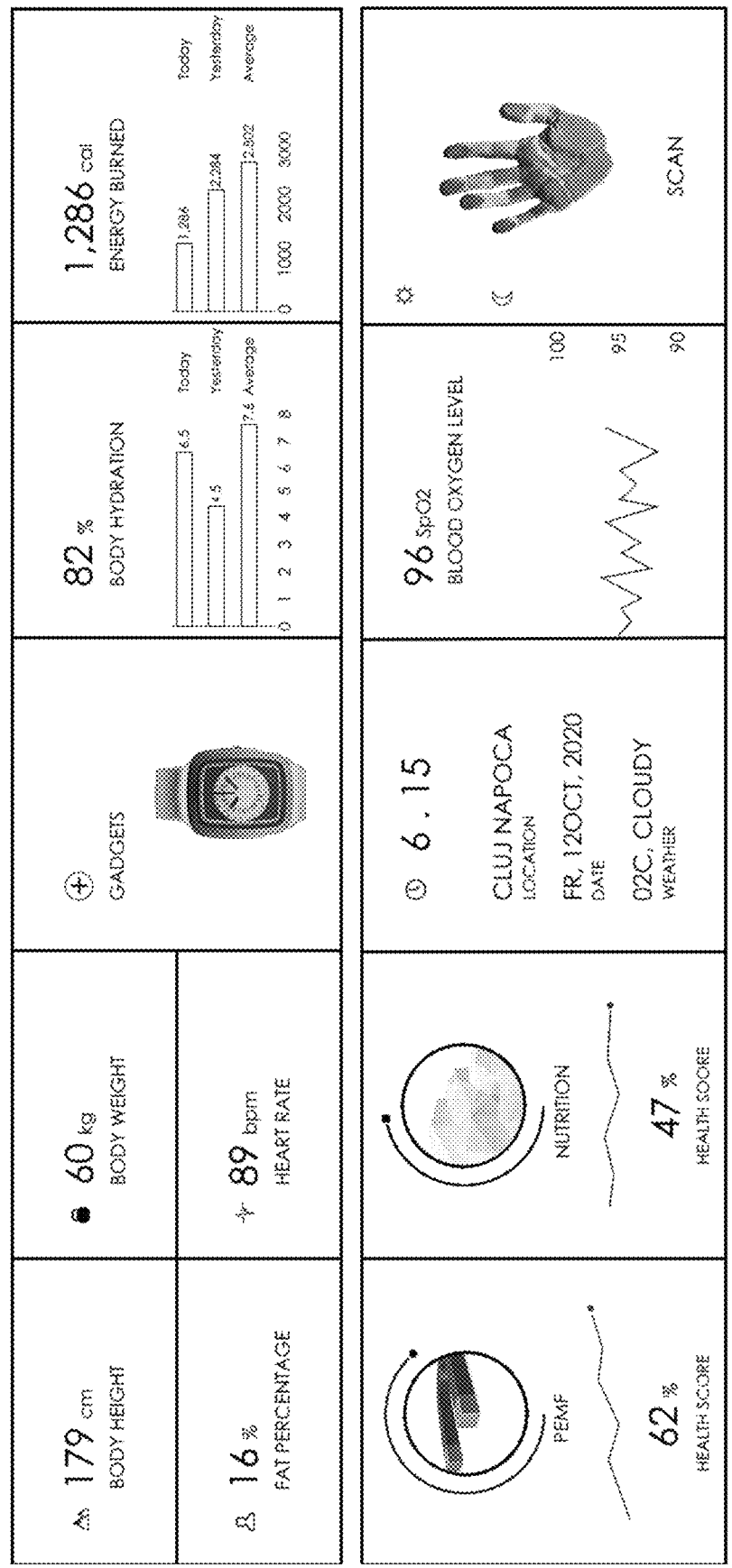
FIG. 47 illustrates a dashboard screen for another embodiment of a GUI for a mobile application.

FIG. 47 illustrates a dashboard screen for another embodiment of a GUI for a mobile application. In this embodiment, the dashboard screen displays a personal health score for a user. In a preferred embodiment, the personal health score is calculated using a sleep quality score and a sleep quantity score. In one embodiment, the personal health score is calculated by weighing the sleep quality score higher than the sleep quantity score. In one example, a ratio of 9:7 of sleep quality score to sleep quantity score is used to calculate the personal health score.

A body height and a body weight for the user are displayed on the dashboard screen. Although the body height and the body weight are displayed in metric units (cm and kg, respectively), the mobile application is operable to display alternative units (e.g., feet, pounds). In one embodiment, the body weight is obtained from a smart scale (e.g., Fitbit® Aria®, Nokia® Body+™ Garmin® Index™, Under Armour® Scale, Pivotal Living® Smart Scale, iHealth® Core) and/or through a third-party application. Alternatively, the body height and/or the body weight are entered manually by the user. A fat percentage for the user is displayed on the dashboard screen. In one embodiment, the fat percentage is obtained from a smart scale using bioelectrical impedance and/or through a third-party application. In another embodiment, the fat percentage is entered manually by the user. Alternatively, the dashboard displays a body mass index for the user. The body mass index is calculated using the body weight and the body height of the user. A heart rate for the user is displayed on the dashboard screen. The heart rate is preferably obtained from the heart rate sensor.

The dashboard screen allows the user to link gadgets (e.g., Fitbit®, Jawbone® UP, Misfit™, Apple Watch®, Nokia® Steel, Nokia® Go, smart scales) to the mobile application. A body hydration level is displayed for the user on the dashboard screen. In one embodiment, the body hydration level is expressed as a percentage. In one embodiment, the body hydration level is calculated based on a number of glasses of water a day. In one example, a user has consumed 4 glasses of water in a day with a target of 8 glasses of water in a day, resulting in a body hydration level of 50%. Alternatively, the body hydration level is calculated based on a number of ounces of water. In one example, a user has consumed 1.5 L of water in a day with a target of 3 L of water in a day, resulting in a body hydration level of 50%. In a preferred embodiment, the screen displays a body hydration level for today, yesterday, and/or an overall average.

An energy burned for the user is displayed on the dashboard screen. The energy burned is preferably displayed as the number of calories burned. In a preferred embodiment, the energy burned is obtained from a wearable device (e.g., Fitbit®, Jawbone® UP, Misfit™, Apple Watch®, Nokia® Steel, Nokia® Go). In another embodiment, the energy burned is obtained from a smartphone or a third-party application. Alternatively, the energy burned is manually entered by the user. In a preferred embodiment, the screen displays an energy burned level for today, yesterday, and/or an overall average.

The dashboard screen also displays a PEMF health score. The PEMF health score is preferably displayed as a percentage. In a preferred embodiment, the PEMF health score is based on user input. In one example, the PEMF health score is based on answers to survey questions. The survey questions ask the user to rate pain one hour after treatment, during physical activity, 24 hours after treatment, two days after treatment, five days after treatment, and/or one week after treatment. The survey questions ask the user to rate flexibility and/or mobility one hour after treatment, during physical activity, 24 hours after treatment, two days after treatment, five days after treatment, and/or one week after treatment. The answers to the survey questions determine the level of treatment needed and the PEMF health score. In one example, an acute issue is given a PEMF health score between about 0% and about 35%, an ongoing issue is given a PEMF health score between about 35% and about 65%, and a managed issue requiring booster treatments (e.g., a monthly booster treatment) is given a PEMF health score between about 65% and about 95%.

A nutrition health score is displayed for the user on the dashboard screen. The nutrition health score is preferably displayed as a percentage. In a preferred embodiment, the nutrition health score is based on user input. In one embodiment, the nutrition health score is based on a target number of calories. In one example, a user has consumed 1000 calories in a day with a target of 2000 calories in a day, resulting in a nutrition health score of 50%. In another embodiment, the nutrition health score is based on a target percentage of fat, a target percentage of carbohydrates, and/or a target percentage of protein. Alternatively, the nutrition health score is based on a target total amount of fat, a target total amount of carbohydrates, and/or a target total amount of protein. In one example, a user has consumed 50 grams of protein with a target of 100 grams of protein in a day, resulting in a nutrition health score of 50%. In yet another embodiment, the nutrition health score includes nutritional supplements (e.g., vitamins, minerals, herbals, botanicals, amino acids, enzymes, probiotics, prebiotics) consumed by the user.

The dashboard screen also displays a time of day (e.g., 6:15), a location, a date, and/or a weather forecast for the location. In one embodiment, the weather forecast for the location includes a temperature and/or a condition (e.g., cloudy, sunny).

A blood oxygen level for the user is displayed on the dashboard screen. The blood oxygen level for the user is obtained from the pulse oximeter sensor. The dashboard screen includes a button to prompt a scan with an energy field sensor. In a preferred embodiment, the energy field sensor is a GDV device. In one embodiment, the GDV device scans at least one hand and/or at least one finger of a user to measure an energy field of the user.

FIG. 48 illustrates a treatment summary screen for one embodiment of a GUI for a mobile application. The treatment summary screen displays a number of minutes for treatments within a month for a user. In this embodiment, the treatment summary screen displays the number of minutes the user was treated using infrared, TENS, and PEMF during the month. In a preferred embodiment, the number of minutes the user was treated within the month is displayed as a bar graph, with each of the treatments (e.g., infrared, TENS, PEMF) displayed in different colors. A date of the month (e.g., 1, 3, 6, 9, 12, 15, 18, 21, 24, 27) is preferably displayed under the number of minutes the user was treated.

Figure 49:
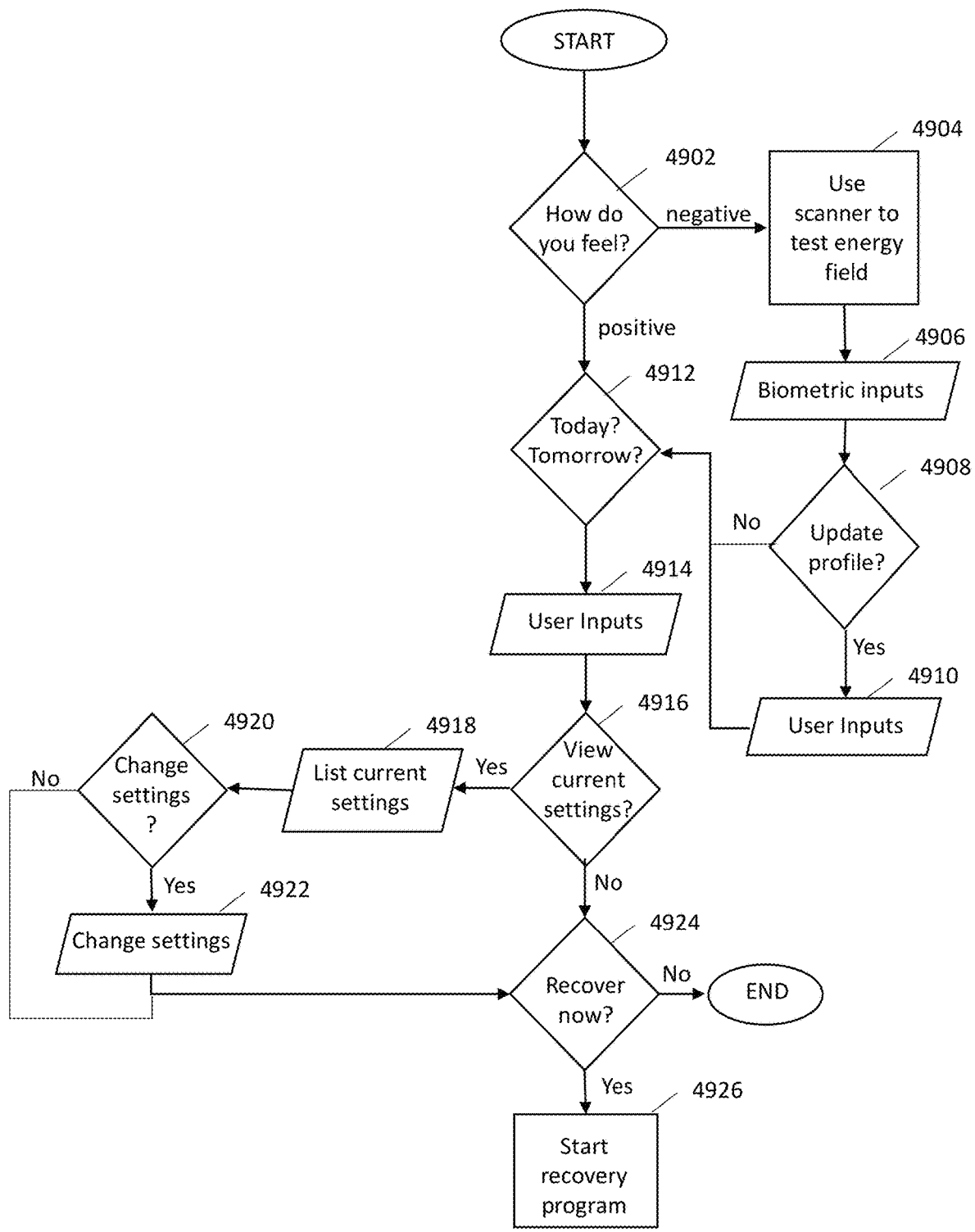
FIG. 49 is a diagram illustrating an example process of a user interacting with the mobile application before a sleeping period.

FIG. 49 is a diagram illustrating an example process of a user interacting with the mobile application before a sleeping period. First, in step 4902, the mobile application asks the user how they feel. In one embodiment, the mobile application asks the user to provide a numerical score (e.g., 1-10) rating how they feel. In one example, a numerical score corresponding to 1-7 is considered negative and a numerical score corresponding to 8-10 is considered positive. Alternatively, the mobile application provides descriptions (e.g., need help, not good, just OK, could be better, great) for the user to select regarding how they feel. In one example, need help, not good, just OK, and could be better is considered negative and great is considered positive. In another embodiment, the mobile application asks the user to rate health issues (e.g., shoulder pain rated 5, knee pain rated 7, back pain rated 8). If the user feels positive, the mobile application proceeds to step 4912. If the user feels negative, the mobile application prompts the user to scan their energy field in step 4904 with the energy field sensor. The mobile application obtains biometric inputs in step 4906. The biometric inputs are from the body sensors and/or third-party applications (e.g., Fitbit®, Jawbone®, Misfit™, MyFitness-Pal®, Apple® Health, Nokia® Health Mate). In step 4908, the mobile application asks if the user wants to update their profile. In one example, the mobile application questions if the user wants to update their profile due to pain or other symptoms and/or if the user has any changes to their medical history (e.g., under doctor's treatment, newly diagnosed condition such as diabetes). If the user wants to update their profile, the user supplies inputs in step 4910 and the mobile application proceeds to step 4912. If the user does not want to update their profile, the mobile application proceeds to step 4912.

The mobile application asks the user about today and/or tomorrow in step 4912. In one example, the mobile application asks the user about physical activity, nutrition, hydration, stress, sleep (e.g., nap), and/or bedtime for today. Alternatively, the mobile application acquires the information from a third-party application and/or the body sensors.

In another example, the mobile application asks the user about plans for tomorrow (e.g., cognitive tasks such as a test or important meeting, physical activity such as a marathon, stress or emotional issues such as a family member with health issues). The user provides inputs in step 4914.

The mobile application asks if the user wants to view current settings for the stress reduction and sleep promotion system in step 4916. If the user does not want to view the current settings, the mobile application proceeds to step 4924. If the user does want to view the current settings, the mobile application lists the current settings in step 4918. The mobile application asks the user if they want to change the settings for the stress reduction and sleep promotion system in step 4920. If the user does not want to change the settings, the mobile application proceeds to step 4924. If the user does want to change the settings, the settings are updated in step 4922 and the mobile application proceeds to step 4924. The mobile application asks the user if they would like to recover now (i.e., start treatment) in step 4924. The treatment utilizes the system components (e.g., temperature-regulating mattress pad, PEMF device, TENS device, red and/or near-infrared lighting device) to reduce stress and promote sleep.

Figure 50:
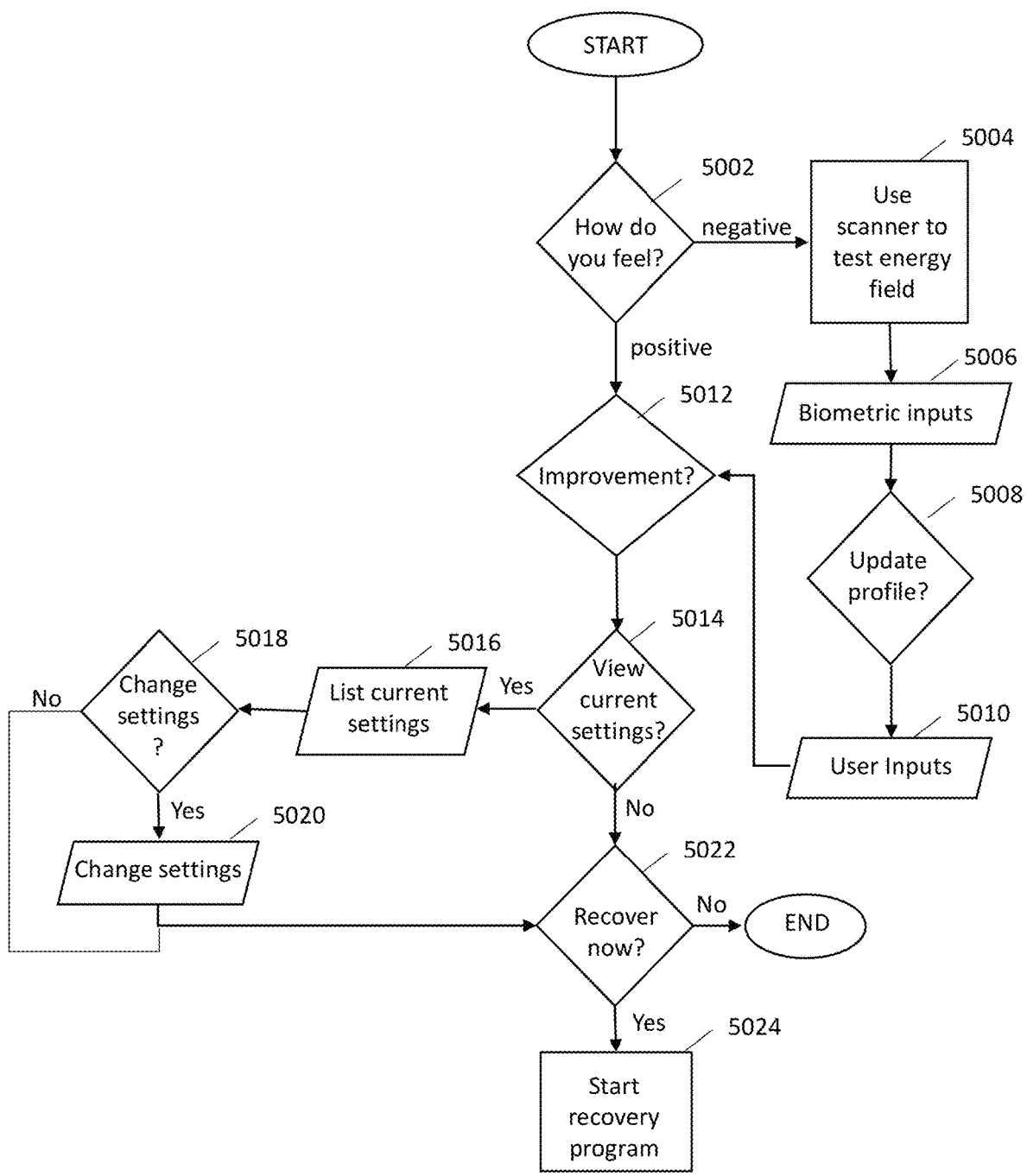
FIG. 50 is a diagram illustrating an example process of a user interacting with the mobile application after a sleeping period.

FIG. 50 is a diagram illustrating an example process of a user interacting with the mobile application after a sleeping period. First, in step 5002, the mobile application asks the user how they feel. In one embodiment, the mobile application asks the user to provide a numerical score (e.g., 1-10) rating how they feel. In one example, a numerical score corresponding to 1-7 is considered negative and a numerical score corresponding to 8-10 is considered positive. Alternatively, the mobile application provides descriptions (e.g., need help, not good, just OK, could be better, great) for the user to select regarding how they feel. In one example, need help, not good, just OK, and could be better is considered negative and great is considered positive. In another embodiment, the mobile application asks the user to rate health issues (e.g., shoulder pain rated 5, knee pain rated 7, back pain rated 8). If the user feels positive, the mobile application proceeds to step 5012. If the user feels negative, the mobile application prompts the user to scan their energy field in step 5004 with the energy field sensor. The mobile application obtains biometric inputs in step 5006. The biometric inputs are from the body sensors and/or third-party applications (e.g., Fitbit®, Jawbone®, Misfit™, MyFitnessPal®, Apple® Health, Nokia® Health Mate). In step 5008, the mobile application asks if the user wants to update their profile. In one example, the mobile application questions if the user wants to update their profile due to pain or other symptoms and/or if the user has any changes to their medical history (e.g., under doctor's treatment, newly diagnosed condition such as diabetes). If the user wants to update their profile, the user supplies inputs in step 5010 and the mobile application proceeds to step 5012. If the user does not want to update their profile, the mobile application proceeds to step 5012.

The mobile application asks the user whether there was an improvement in their condition in step 5012. Alternatively, the mobile application determines whether there was an improvement in their condition based on condition ratings before the sleeping period. In one example, shoulder pain was rated 5 before the sleeping period and rated 3 after the sleeping period, representing improvement in the shoulder condition.

The mobile application asks if the user wants to view current settings for the stress reduction and sleep promotion system in step 5014. If the user does not want to view the current settings, the mobile application proceeds to step 5022. If the user does want to view the current settings, the mobile application lists the current settings in step 5016. The mobile application asks the user if they want to change the settings for the stress reduction and sleep promotion system in step 5018. If the user does not want to change the settings, the mobile application proceeds to step 5022. If the user does want to change the settings, the settings are updated in step 5020 and the mobile application proceeds to step 5022. The mobile application asks the user if they would like to recover now (i.e., start treatment) in step 5022. The treatment utilizes the system components (e.g., temperature-regulating mattress pad, PEMF device, TENS device, red and/or near-infrared lighting device) to reduce stress and promote sleep. If the user wants to start treatment, the recovery program begins in step 5024. The mobile application selects an appropriate recovery program based on the time of day and/or user preferences. In one example, the user wants to start treatment after a sleeping period and the mobile application selects a treatment with the PEMF device to reduce stress.

In another embodiment, the mobile application uses at least one photographic affect meter (PAM) to determine a mood of a user. The mobile application displays a plurality of photographs and the user selects a photograph that best corresponds to the mood of the user. One example of a PAM is described in Pollak, J. P., Adams, P., Gay, G. (2011) PAM: A photographic affect meter for frequent, in situ measurement of affect. in the Proceedings of the ACM Conference on Human Factors in Computing Systems (CHI 2011) Vancouver, BC, Canada, May 5-12, pp. 725-734, which is incorporated herein by reference in its entirety.

In one embodiment, the system is a decentralized platform utilizing blockchain technology. The decentralized platform is operable to store information regarding the user's health, sleep, and stress levels. In one embodiment, the data blocks within the chain are encrypted using cryptography. Individual users can grant access to their data by providing another individual (e.g., healthcare provider) with a private password or key. The blockchain-based decentralized platform provides security for peer-to-peer sharing of medical information by preventing unauthorized access to the user's private medical information.

Figure 51:
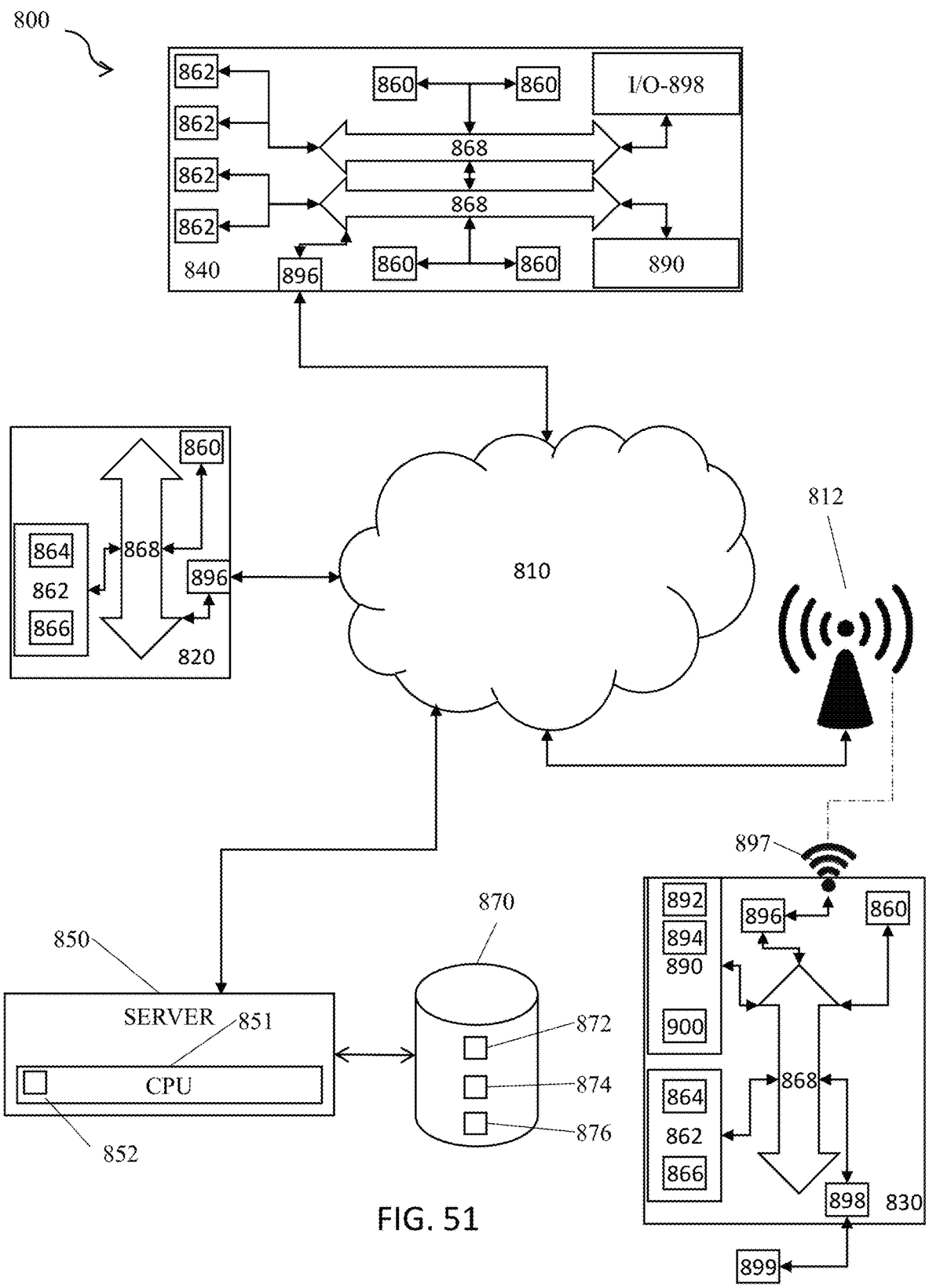
FIG. 51 shows a schematic diagram illustrating general components of a cloud-based computer system.

FIG. 51 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 51, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 51, may include other components that are not explicitly shown in FIG. 51, or may utilize an architecture completely different than that shown in FIG. 51. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By way of example, the temperature regulating article can be a mattress pad, a sleeping bag, a cushion, or a blanket. The above-mentioned examples are just some of the many configurations that the mentioned components can take on. All modifications and improvements have been deleted herein for the sake of conciseness and readability but are properly within the scope of the present invention.

The invention claimed is:

1. A stress reduction and sleep promotion system comprising:
    at least one body sensor;
    at least one remote device;
    at least one remote server; and
    an article for adjusting a temperature of a surface, wherein the article further comprises:
        a first layer, wherein the first layer has an exterior surface and an interior surface;
        a second layer, wherein the second layer has an exterior surface and an interior surface, and wherein the second layer is permanently affixed to the first layer along a periphery of the article;
        at least one interior chamber defined between the interior surface of the first layer and the interior surface of the second layer;
        at least one flexible fluid supply line for delivering a fluid to the at least one interior chamber;
        at least one flexible fluid return line for removing the fluid from the at least one interior chamber; and
        at least one control unit attached to the at least one flexible fluid supply line and the at least one flexible fluid return line, wherein the at least one control unit is operable to selectively cool or heat the fluid, and wherein the at least one control unit has at least one antenna and at least one processor;
    wherein the at least one remote device and the at least one control unit are in real-time or near-real-time two-way communication;
    wherein the at least one remote server further includes a calibration engine and a global analytics engine;
    wherein the global analytics engine generates predicted values for the article based on data generated by the at least one body sensor in real-time;
    wherein the calibration engine generates a virtual model of the article based on optimized parameters for the article;
    wherein the calibration engine automatically updates the virtual model of the article in real time based on a difference between the predicted values for the article generated by the global analytics engine and the optimized parameters for the article;
    wherein the at least one interior chamber is constructed and configured to retain the fluid without leaking; and
    wherein the interior surface of the first layer and the interior surface of the second layer are comprised of at least one layer of a waterproof material.

2. The stress reduction and sleep promotion system of claim 1, further comprising at least one remote server in real-time or near-real-time two-way communication with the at least one remote device.

3. The stress reduction and sleep promotion system of claim 1, wherein the at least one body sensor is a respiration sensor, an electrooculography sensor, a heart rate sensor, a movement sensor, an electromyography sensor, a brain wave sensor, an analyte sensor, a pulse oximeter sensor, a blood pressure sensor, and/or an electrodermal activity sensor.

4. The stress reduction and sleep promotion system of claim 1, further comprising at least one environmental sensor, wherein the environmental sensor is a temperature sensor, a humidity sensor, a noise sensor, an air quality sensor, a light sensor, a motion sensor, and/or a barometric sensor.

5. The stress reduction and sleep promotion system of claim 1, wherein the at least one control unit is operable to receive parameters from the at least one remote device to modify the temperature of the surface.

6. The stress reduction and sleep promotion system of claim 5, wherein the at least one remote device wirelessly transmits the parameters via a wireless personal area network (WPAN) and/or a wireless local area network (WLAN).

7. The stress reduction and sleep promotion system of claim 1, wherein:
    the first layer has a plurality of openings;
    the second layer has a corresponding plurality of openings; and
    the second layer is permanently affixed to the first layer along a periphery of each of the plurality of openings.

8. The stress reduction and sleep promotion system of claim 1, further comprising a mattress with adjustable firmness and/or elevation, an alarm clock, a humidifier, a dehumidifier, a pulsed electromagnetic field device, a transcutaneous electrical nerve stimulation device, a sound generator, an air purifier, a scent generator, red and/or near-infrared lighting, a sunrise simulator, and/or a sunset simulator.

9. The stress reduction and sleep promotion system of claim 1, further comprising a home automation system, wherein the at least one remote device is operable to transmit commands to the home automation system to adjust environmental conditions.

10. The stress reduction and sleep promotion system of claim 1, wherein the fluid is water.

11. A stress reduction and sleep promotion system comprising:
    a plurality of body sensors;
    at least one remote device;
    at least one remote server; and
    an article for adjusting a temperature of a surface, wherein the article further comprises:
        a first layer, wherein the first layer has an exterior surface and an interior surface;
        a second layer, wherein the second layer has an exterior surface and an interior surface, and wherein the second layer is permanently affixed to the first layer along a periphery of the article;
        at least one interior chamber defined between the interior surface of the first layer and the interior surface of the second layer;
        at least one flexible fluid supply line for delivering a fluid to the at least one interior chamber;
        at least one flexible fluid return line for removing the fluid from the at least one interior chamber; and
        at least one control unit attached to the at least one flexible fluid supply line and the at least one flexible fluid return line, wherein the at least one control unit is operable to selectively cool or heat the fluid, and wherein the at least one control unit has at least one antenna and at least one processor;
    wherein the article for adjusting a temperature of a surface includes a plurality of sections, and wherein the temperature of each of the plurality of sections is independently controllable;
    wherein the at least one remote server and the at least one remote device are in real-time or near-real-time two-way communication;
    wherein the at least one remote device and the at least one control unit are in real-time or near-real-time two-way communication;
    wherein the at least one remote server is operable to determine optimized parameters for a sleep cycle based on data from the plurality of body sensors;

wherein the at least one remote server is operable to transmit the optimized parameters for the sleep cycle to the at least one remote device;
wherein the at least one remote device is operable to transmit the optimized parameters for the sleep cycle to the at least one control unit;
wherein the at least one remote server further includes a calibration engine and a global analytics engine;
wherein the global analytics engine generates predicted values for the article based on data generated by the plurality of body sensors in real-time;
wherein the calibration engine generates a virtual model of the article based on the optimized parameters for the sleep cycle;
wherein the calibration engine automatically updates the virtual model of the article in real time based on a difference between the predicted values for the article generated by the global analytics engine and the optimized parameters for the sleep cycle;
wherein the at least one interior chamber is constructed and configured to retain the fluid without leaking; and
wherein the interior surface of the first layer and the interior surface of the second layer are comprised of at least one layer of a waterproof material.

12. The stress reduction and sleep promotion system of claim 11, wherein the plurality of body sensors includes at least one respiration sensor, at least one electrooculography sensor, at least one heart rate sensor, at least one movement sensor, at least one electromyography sensor, at least one brain wave sensor, at least one analyte sensor, at least one pulse oximeter sensor, at least one blood pressure sensor, and/or at least one electrodermal activity sensor.

13. The stress reduction and sleep promotion system of claim 11, wherein the at least one control unit is operable to receive parameters from the at least one remote device to modify the temperature of the surface.

14. The stress reduction and sleep promotion system of claim 11, wherein the at least one remote device wirelessly transmits the parameters via a wireless personal area network (WPAN) and/or a wireless local area network (WLAN).

15. The stress reduction and sleep promotion system of claim 11, wherein:
the first layer has a plurality of openings;
the second layer has a corresponding plurality of openings; and
the second layer is permanently affixed to the first layer along a periphery of each of the plurality of openings.

16. The stress reduction and sleep promotion system of claim 11, further comprising a mattress with adjustable firmness and/or elevation, an alarm clock, a humidifier, a dehumidifier, a pulsed electromagnetic field device, a transcutaneous electrical nerve stimulation device, a sound generator, an air purifier, a scent generator, red and/or near-infrared lighting, a sunrise simulator, and/or a sunset simulator.

17. The stress reduction and sleep promotion system of claim 11, further comprising at least one environmental sensor, wherein the environmental sensor is a temperature sensor, a humidity sensor, a noise sensor, an air quality sensor, a light sensor, a motion sensor, and/or a barometric sensor.

18. The stress reduction and sleep promotion system of claim 11, further comprising a home automation system, wherein the at least one remote device is operable to transmit commands to the home automation system to adjust environmental conditions.

19. The stress reduction and sleep promotion system of claim 11, wherein the plurality of body sensors and the at least one remote device are in real-time or near-real-time two-way communication.

20. A stress reduction and sleep promotion system comprising:
a plurality of body sensors;
at least one remote device;
at least one remote server; and
an article for adjusting a temperature of a surface, wherein the article further comprises:
a first layer, wherein the first layer has an exterior surface and an interior surface;
a second layer, wherein the second layer has an exterior surface and an interior surface, and wherein the second layer is permanently affixed to the first layer along a periphery of the article;
at least one interior chamber defined between the interior surface of the first layer and the interior surface of the second layer;
at least one flexible fluid supply line for delivering a fluid to the at least one interior chamber;
at least one flexible fluid return line for removing the fluid from the at least one interior chamber; and
at least one control unit attached to the at least one flexible fluid supply line and the at least one flexible fluid return line, wherein the at least one control unit is operable to selectively cool or heat the fluid, and wherein the at least one control unit has at least one antenna and at least one processor;
wherein the article for adjusting a temperature of a surface includes a plurality of sections, and wherein the temperature of each of the plurality of sections is independently controllable;
wherein the at least one remote server and the at least one remote device are in real-time or near-real-time two-way communication;
wherein the at least one remote device and the at least one control unit are in real-time or near-real-time two-way communication;
wherein the at least one remote server is operable to determine optimized parameters for a sleep cycle based on data from the plurality of body sensors;
wherein the at least one remote server is operable to transmit the optimized parameters for the sleep cycle to the at least one remote device;
wherein the at least one remote device is operable to transmit the optimized parameters for the sleep cycle to the at least one control unit;
wherein the at least one control unit is operable to control the article to adjust the temperature of the surface based on the optimized parameters for the sleep cycle;
wherein the at least one remote server further includes a calibration engine and a global analytics engine;
wherein the global analytics engine generates predicted values for the article based on data generated by the plurality of body sensors in real-time;
wherein the calibration engine generates a virtual model of the article based on the optimized parameters for the sleep cycle;
wherein the calibration engine automatically updates the virtual model of the article in real time based on a difference between the predicted values for the article generated by the global analytics engine and the optimized parameters for the sleep cycle;
wherein the at least one interior chamber is constructed and configured to retain the fluid without leaking;

wherein the interior surface of the first layer and the interior surface of the second layer are comprised of at least one layer of a waterproof material;

wherein the at least one control unit includes at least one thermoelectric module used to selectively cool the fluid; and wherein the plurality of body sensors includes at least one respiration sensor, at least one electrooculography sensor, at least one heart rate sensor, at least one movement sensor, at least one electromyography sensor, at least one brain wave sensor, at least one analyte sensor, at least one pulse oximeter sensor, at least one blood pressure sensor, and/or at least one electrodermal activity sensor.

* * * * *